(12) United States Patent
Moon

(10) Patent No.: US 10,547,010 B2
(45) Date of Patent: Jan. 28, 2020

(54) ORGANIC ELECTROLUMINESCENT COMPOUNDS AND ORGANIC ELECTROLUMINESCENT DEVICE COMPRISING THE SAME

(71) Applicant: Rohm and Haas Electronic Materials Korea Ltd., Cheonan (KR)

(72) Inventor: Doo-Hyeon Moon, Hwaseong (KR)

(73) Assignee: Rohm and Haas Electronic Materials Korea Ltd., Cheonan (KR)

( * ) Notice: Subject to any disclaimer, the term of this patent is extended or adjusted under 35 U.S.C. 154(b) by 0 days.

(21) Appl. No.: 15/777,747

(22) PCT Filed: Dec. 1, 2016

(86) PCT No.: PCT/KR2016/014013
§ 371 (c)(1),
(2) Date: May 21, 2018

(87) PCT Pub. No.: WO2017/095156
PCT Pub. Date: Jun. 8, 2017

(65) Prior Publication Data
US 2018/0337340 A1    Nov. 22, 2018

(30) Foreign Application Priority Data

Dec. 4, 2015 (KR) .......... 10-2015-0172324
Nov. 25, 2016 (KR) .......... 10-2016-0158003

(51) Int. Cl.
*C07D 487/16* (2006.01)
*C09K 11/06* (2006.01)
*H01L 51/00* (2006.01)
*H01L 51/56* (2006.01)
*H01L 51/50* (2006.01)

(52) U.S. Cl.
CPC ........ *H01L 51/0067* (2013.01); *C07D 487/16* (2013.01); *C09K 11/06* (2013.01); *H01L 51/0072* (2013.01); *C09K 2211/1018* (2013.01); *H01L 51/001* (2013.01); *H01L 51/5016* (2013.01); *H01L 51/5064* (2013.01); *H01L 51/5072* (2013.01); *H01L 51/5088* (2013.01); *H01L 51/56* (2013.01); *H01L 2251/558* (2013.01)

(58) Field of Classification Search
CPC ... C07D 487/16; C09K 11/06; H01L 51/0067; H01L 51/0072; H01L 51/56
See application file for complete search history.

(56) References Cited

U.S. PATENT DOCUMENTS 9,502,667 B2   11/2016  Saito et al.
2017/0047527 A1  2/2017  Lee et al.

FOREIGN PATENT DOCUMENTS

KR   10-2014-0076522 A   6/2014
KR   10-2015-0077220 A   7/2015

*Primary Examiner* — Brenda L Coleman
(74) *Attorney, Agent, or Firm* — S. Matthew Cains

(57) ABSTRACT

The present disclosure relates to an organic electroluminescent compound and an organic electroluminescent device comprising the same. The organic electroluminescent compound of the present disclosure provides an organic electroluminescent device having a remarkably improved lifespan.

9 Claims, No Drawings

ORGANIC ELECTROLUMINESCENT COMPOUNDS AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak, by using small aromatic diamine molecules and aluminum complexes as materials to form a light-emitting layer [Appl. Phys. Lett. 51, 913, 1987].

The most important factor determining luminous efficiency in the organic EL device is light-emitting materials. Until now, fluorescent materials have been widely used as light-emitting material. However, in view of electroluminescent mechanisms, since phosphorescent materials theoretically enhance luminous efficiency by four (4) times compared to fluorescent materials, phosphorescent light-emitting materials have been widely researched. Iridium(III) complexes have been widely known as phosphorescent materials, including bis(2-(2'-benzothienyl)-pyridinato-N,C-3')iridium(acetylacetonate) ((acac)Ir(btp)$_2$), tris(2-phenylpyridine)iridium (Ir(ppy)$_3$) and bis(4,6-difluorophenylpyridinato-N,C2)picolinate iridium (Firpic) as red-, green- and blue-emitting materials, respectively.

At present, 4,4'-N,N'-dicarbazol-biphenyl (CBP) is the most widely known host material for phosphorescent materials. Recently, Pioneer (Japan) et al., developed a high performance organic EL device using bathocuproine (BCP) and aluminum(III) bis(2-methyl-8-quinolinate)(4-phenylphenolate) (BAlq) etc., as host materials, which were known as hole blocking materials.

Although these materials provide good light-emitting characteristics, they have the following disadvantages: (1) Due to their low glass transition temperature and poor thermal stability, their degradation may occur during a high-temperature deposition process in a vacuum, which results in poor lifespan. (2) The power efficiency of the organic EL device is given by [(π/voltage)×current efficiency], and the power efficiency is inversely proportional to the voltage. Although the organic EL device comprising phosphorescent host materials provides higher current efficiency (cd/A) than one comprising fluorescent materials, a significantly high driving voltage is necessary. Thus, there is no merit in terms of power efficiency (lm/W). (3) Furthermore, the operational lifespan of the organic EL device is short, and luminous efficiency is still required to be improved. Accordingly, in order to embody the advantageous properties of the organic EL device, it is important to suitably select the materials that are comprised in the organic layer of the organic EL device, especially the host or dopant materials that are comprised in the light-emitting materials.

Japanese Patent Application Laying-Open No. 2014-160813 discloses an organic electroluminescent device comprising a nitrogen-containing heteroaryl compound formed by condensing a pyrrole ring, an aromatic aryl ring, and a 7-membered aryl ring, as host/dopant materials. However, it does not specifically disclose a compound in which a carbazole and an indole are fused with a 7-membered ring.

Korean Patent Application Laying-Open No. 10-2015-077220 discloses a compound in which an amine radical is fused with dibenzo residue including a carbazole, fluorene, or 5-membered hetero ring to form a ring. However, it does not specifically disclose a compound wherein a parent nucleus formed by a fusion of a carbazole, an indole, and a 7-membered ring, is connected, directly or via a linker of arylene or heteroarylene, to a 10-membered nitrogen-containing heteroaryl.

DISCLOSURE OF THE INVENTION

Problems to be Solved

The objective of the present disclosure is to provide an organic electroluminescent compound, which is effective in preparing an organic electroluminescent device having a remarkably improved lifespan, and an organic electroluminescent device comprising the organic electroluminescent compound.

Solution to Problems

As a result of an earnest study for solving the above-described problems, the present inventor found that the above objective can be achieved by an organic electroluminescent compound represented by the following formula 1 and has come to complete the present disclosure:

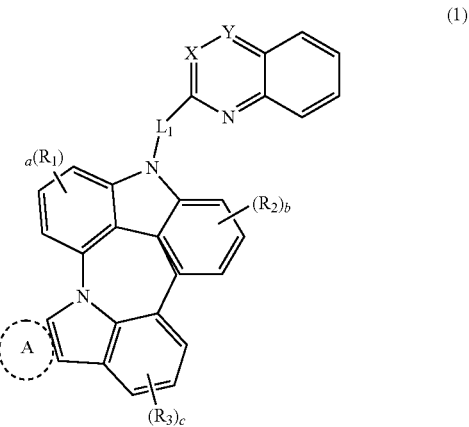

wherein

X and Y, each independently, represent CR$_4$ or N;

L$_1$ represents a single bond, a substituted or unsubstituted (C6-C30)arylene, or a substituted or unsubstituted (3- to 30-membered) heteroarylene;

A represents hydrogen, a substituted or unsubstituted (C6-C30)aryl, or a substituted or unsubstituted (3- to 30-membered) heteroaryl;

R$_1$ to R$_3$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to an adjacent substituent(s) to form a substituted or unsubstituted (3 to 30-membered), mono- or polycyclic, alicyclic or aromatic ring, or a fused ring of the alicyclic ring and the aromatic ring, whose carbon atom(s) may be replaced with at least one heteroatom selected from the group consisting of nitrogen, oxygen, and sulfur;

$R_4$ represents hydrogen, deuterium, a halogen, a cyano, a substituted or unsubstituted (C1-C30)alkyl, a substituted or unsubstituted (C6-C30)aryl, a substituted or unsubstituted (3-to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

wherein the heteroaryl(ene) contains one or more heteroatoms selected from the group consisting of B, N, O, S, Si, and P;

a, b, and c, each independently, represent an integer of 1 to 3, and when a, b, or c is an integer of 2 or more, each of $R_1$, $R_2$ or $R_3$ may be the same or different.

Effects of the Invention

The present disclosure provides an organic electroluminescent device that has a remarkably improved lifespan.

EMBODIMENTS OF THE INVENTION

Hereinafter, the present disclosure will be described in detail. However, the following description is intended to explain the invention, and is not meant in any way to restrict the scope of the invention.

The compound of formula 1 is more specifically described below.

Herein, "an organic electroluminescent compound" indicates a compound that may be used for an organic electroluminescent device. The compound may be comprised in any layer of the organic electroluminescent device, as necessary.

In formula 1, X and Y, each independently, may represent $CR_4$ or N. Preferably, any one of X and Y is $CR_4$, and the other one is N.

In formula 1, $L_1$ may represent a single bond or a substituted or unsubstituted (C6-C30)arylene, or a substituted or unsubstituted (3- to 30-membered) heteroarylene, preferably a single bond, a substituted or unsubstituted (C6-C25)arylene, or a substituted or unsubstituted (5- to 25-membered)heteroarylene, and more preferably a single bond, a substituted or unsubstituted (C6-C18)arylene, or an unsubstituted (5- to 18-membered)heteroarylene, such as a single bond, an unsubstituted phenyl, an unsubstituted naphthyl, fluorenyl substituted with dimethyl, or an unsubstituted pyridyl.

In formula 1, A may represent hydrogen, a substituted or unsubstituted (C6-C30)aryl, or a substituted or unsubstituted (3- to 30-membered) heteroaryl, preferably hydrogen, or a substituted or unsubstituted (C6-C25)aryl, and more preferably hydrogen, or an unsubstituted (C6-C18)aryl, such as hydrogen, an unsubstituted phenyl, an unsubstituted naphthyl, or an unsubstituted phenanthrenyl.

In formula 1, $R_1$ to $R_3$, each independently, may represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; may be linked to an adjacent substituent(s) to form a substituted or unsubstituted (3 to 30-membered), mono- or polycyclic, alicyclic or aromatic ring, or a fused ring of the alicyclic ring and the aromatic ring, whose carbon atom(s) may be replaced with at least one heteroatom selected from the group consisting of nitrogen, oxygen, and sulfur; preferably $R_1$ to $R_3$, each independently, may represent hydrogen, or $R_1$ to $R_3$, each independently, may be linked to an adjacent substituent(s) to form a substituted or unsubstituted (C3-C25) mono- or polycyclic aromatic ring, whose carbon atom(s) may be replaced with at least one heteroatom selected from the group consisting of nitrogen, oxygen, and sulfur; more preferably $R_1$ to $R_3$, each independently, may represent hydrogen, or $R_1$ to $R_3$, each independently, may be linked to an adjacent substituent(s) to form a substituted or unsubstituted (C5-C18) mono- or polycyclic aromatic ring, whose carbon atom(s) may be replaced with at least one heteroatom selected from the group consisting of nitrogen, oxygen, and sulfur; for example, $R_1$ to $R_3$, each independently, may represent hydrogen, or $R_1$ to $R_3$, each independently, may be linked to an adjacent substituent(s) to form a substituted or unsubstituted benzene ring, a substituted or unsubstituted naphthalene ring, a substituted or unsubstituted indole ring, a substituted or unsubstituted benzofuran ring, a substituted or unsubstituted benzothiophene ring, or a substituted or unsubstituted indene ring; and specifically, an unsubstituted benzene ring, an unsubstituted naphthalene ring, an indole ring substituted with phenyl, an unsubstituted benzofuran ring, an unsubstituted benzothiophene ring, or an indene ring substituted with dimethyl.

In formula 1, $R_4$ may represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably a substituted or unsubstituted (C6-C25) aryl, or a substituted or unsubstituted (5- to 25-membered) heteroaryl; more preferably a substituted or unsubstituted (C6-C18)aryl, or a substituted or unsubstituted (5- to 18-membered)heteroaryl, such as phenyl substituted or unsubstituted with benzofuran, an unsubstituted biphenyl, fluorenyl substituted with dimethyl or diphenyl, benzofluorenyl substituted with dimethyl, an unsubstituted benzofuranyl, an unsubstituted benzothiophenyl, carbazolyl substituted with phenyl, pyridyl substituted with phenyl, pyrimidinyl substituted with phenyl, or triazinyl substituted with phenyl.

In formula 1, heteroaryl(ene) contains one or more heteroatoms selected from the group consisting of B, N, O, S, Si, and P; and preferably, one or more heteroatoms selected from the group consisting of N, O, and S.

In formula 1, a, b or c, each independently, may represent an integer of 1 to 3; preferably an integer of 1 or 2; and when a, b or c represents an integer of 2 or more, each of $R_1$, $R_2$ or $R_3$ may be the same or different.

The compound of formula 1 of the present disclosure may be represented by any one of the following formulae 2 to 9:

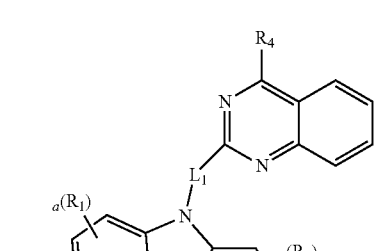

(2)

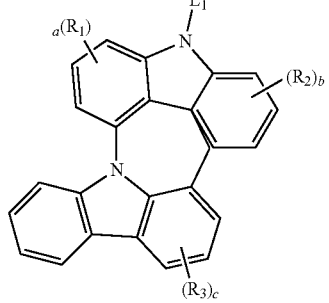

(3)

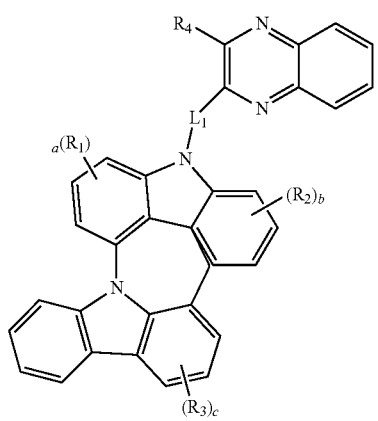

(4)

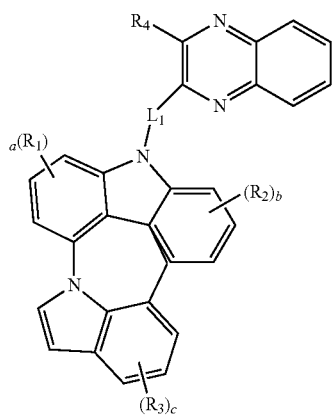

(5)

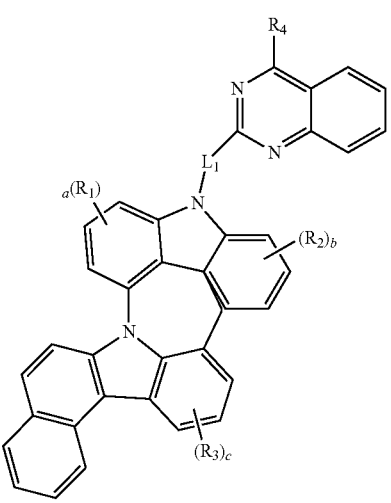

(6)

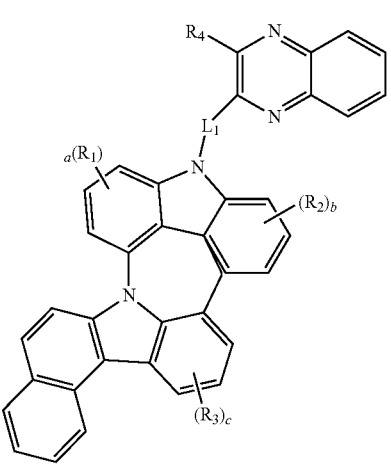

(7)

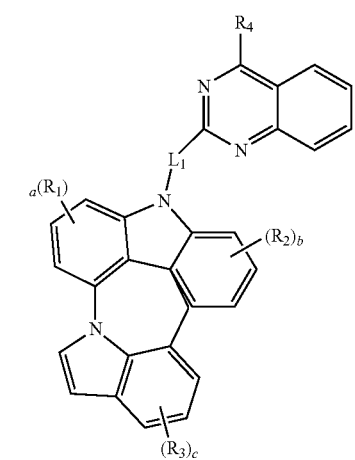

(8)

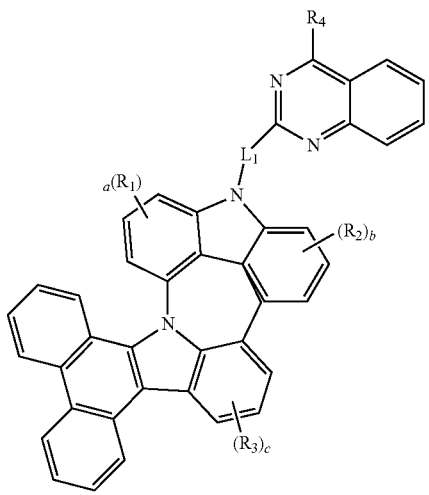

(9)

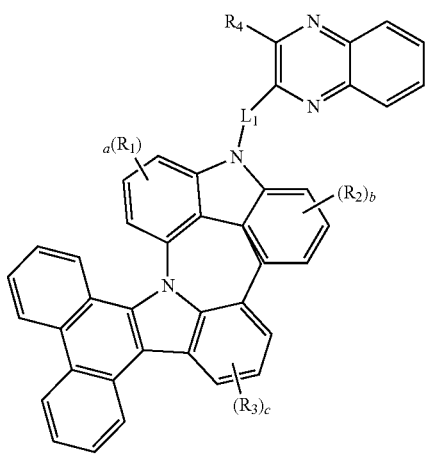

In formulae 2 to 9, $L_1$, $R_1$ to $R_4$, and, a, b, and c are as defined in formula 1 above.

Furthermore, the organic electroluminescent compound of formula 1 may be represented by the following formula 10:

(10)

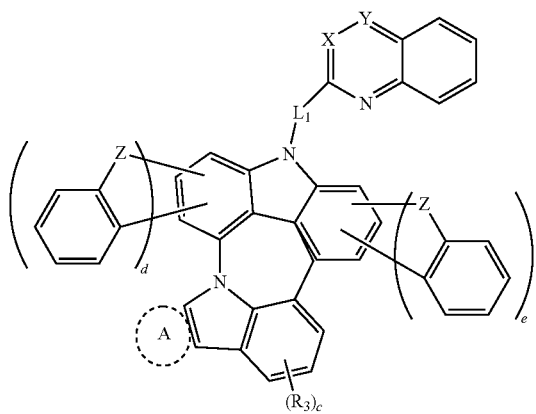

wherein, X, Y, $L_1$, A, $R_3$, and c are as defined in formula 1 above.

In formula 10, Z represents O, S, $CR_5R_6$, or $NR_7$, wherein $R_5$ to $R_7$, each independently, are the same as the definition of $R_4$ in formula 1. Specifically, $R_5$ to $R_7$, each independently, may represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably a substituted or unsubstituted (C1-C20)alkyl, or a substituted or unsubstituted (C6-C25)aryl; and more preferably an unsubstituted (C1-C10)alkyl, or an unsubstituted (C6-C18) aryl. For example, $R_5$ and $R_6$, each independently, may represent an unsubstituted methyl, and $R_7$ may represent an unsubstituted phenyl.

In formula 10, d and e, each independently, represent 0 or 1.

Herein, "(C1-C30)alkyl" indicates a linear or branched alkyl having 1 to 30, preferably 1 to 20, and more preferably 1 to 10 carbon atoms, and includes methyl, ethyl, n-propyl, isopropyl, n-butyl, isobutyl, tert-butyl, etc. "(C2-C30) alkenyl" indicates a linear or branched alkenyl having 2 to 30, preferably 2 to 20, and more preferably 2 to 10 carbon atoms and includes vinyl, 1-propenyl, 2-propenyl, 1-butenyl, 2-butenyl, 3-butenyl, 2-methylbut-2-enyl, etc. "(C2-C30) alkynyl" indicates a linear or branched alkynyl having 2 to 30, preferably 2 to 20, and more preferably 2 to 10 carbon atoms and includes ethynyl, 1-propynyl, 2-propynyl, 1-butynyl, 2-butynyl, 3-butynyl, 1-methylpent-2-ynyl, etc. Herein, "(C3-C30)cycloalkyl" indicates a mono- or polycyclic hydrocarbon having 3 to 30, preferably 3 to 20, more preferably 3 to 7 ring backbone carbon atoms. The cycloalkyl includes cyclopropyl, cyclobutyl, cyclopentyl, cyclohexyl, etc. Herein, "(3 to 7-membered)heterocycloalkyl" indicates a cycloalkyl having 3 to 7, preferably 5 to 7 ring backbone atoms including at least one hetero atom selected from B, N, O, S, Si, and P, preferably O, S, and N, and includes tetrahydrofuran, pyrrolidine, thiolan, tetrahydropyran, etc. Herein, "(C6-C30)aryl(ene)" indicates a monocyclic ring-type or fused ring-type radical derived from aromatic hydrocarbon having 6 to 30, preferably 6 to 20, more preferably 6 to 15 ring backbone carbon atoms. The aryl may have a spiro structure. The aryl includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. Herein, "(3 to 30-membered) heteroaryl(ene)" indicates an aryl group having 3 to 30 ring backbone atoms including at least one, preferably 1 to 4, heteroatoms selected from the group consisting of B, N, O, S, Si, and P; may be a monocyclic ring, or a fused ring condensed with at least one benzene ring; may be partially saturated; may be one formed by linking at least one heteroaryl or aryl group to a heteroaryl group via a single bond(s); and may have a spiro structure. The heteroaryl includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenothiazinyl, phenanthridinyl, benzodioxolyl, dihydroacridinyl, etc. Further, "halogen" includes F, Cl, Br, and I.

Furthermore, herein, "substituted" in the expression, "substituted or unsubstituted," means that a hydrogen atom in a certain functional group is replaced with another atom or group, i.e. a substituent. In $L_1$, A, and $R_1$ to $R_4$, the substituent of the substituted aryl(ene), the substituted heteroaryl(ene), the substituted alkyl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic or aromatic ring, or a fused ring of the alicyclic ring and the aromatic ring, each independently, is at least one selected from the group consisting of deuterium; a halogen; a cyano; a carboxy; a nitro; a hydroxy; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3 to 7-membered) heterocycloalkyl; a (C6-C30)aryloxy; a (C6-C30)arylthio; a (3 to 30-membered) heteroaryl substituted or unsubstituted with a (C1-C30)alkyl or a (C6-C30)aryl; a (C6-C30)aryl substituted or unsubstituted with a (3 to 30-membered) heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. Preferably, the substituent, each independently, is at least one selected from the group consisting of a (C1-C20)alkyl, an unsubstituted (C6-C25)aryl, and an unsubstituted (5- to 25-membered)heteroaryl. More preferably, the substituent, each independently, is at least one selected from the group consisting of a (C1-C10)alkyl, an unsubstituted (C6-C18)aryl, and an unsubstituted (5- to 18-membered)heteroaryl. For example, the substituent, each independently, may be at least one selected from the group consisting of methyl, an unsubstituted phenyl, and an unsubstituted benzofuranyl.

The organic electroluminescent compound of formula 1 includes the following, but is not limited thereto:

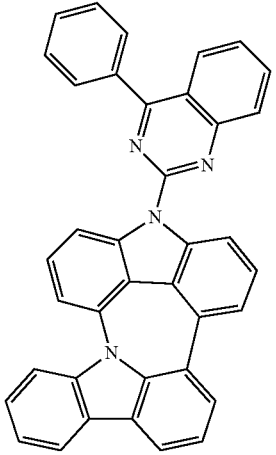

C-1

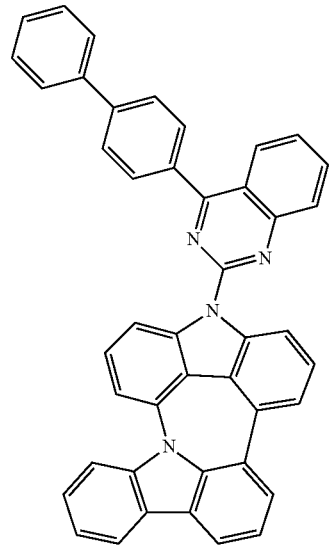

C-2

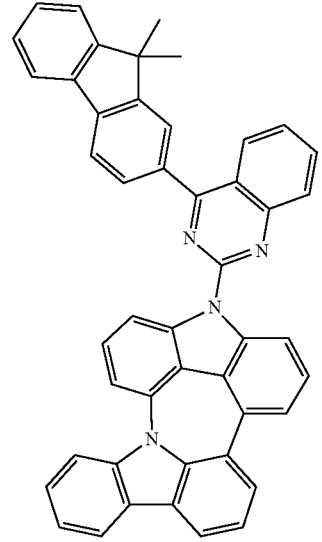

C-3

-continued
C-4
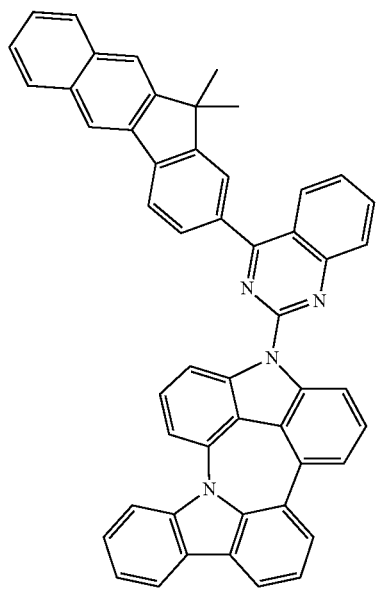
C-5
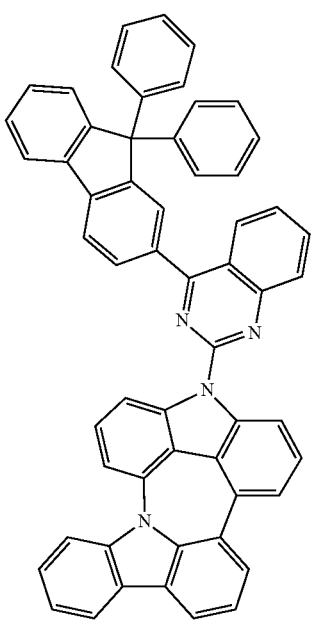
C-6
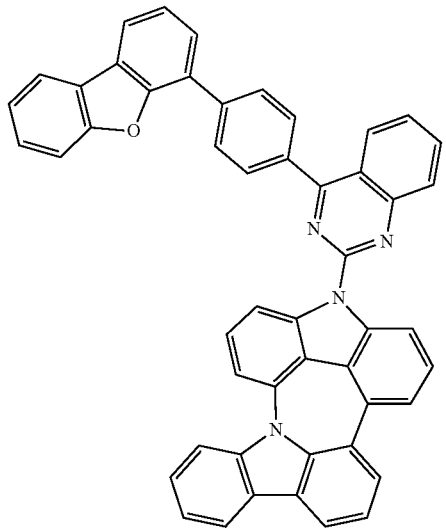
C-7
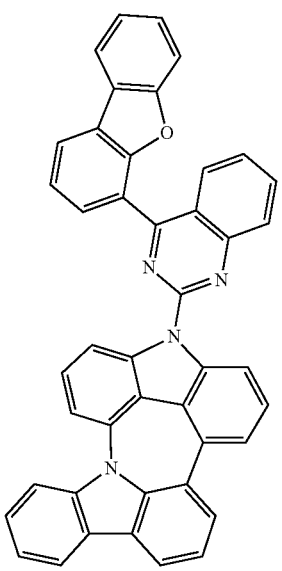
C-8
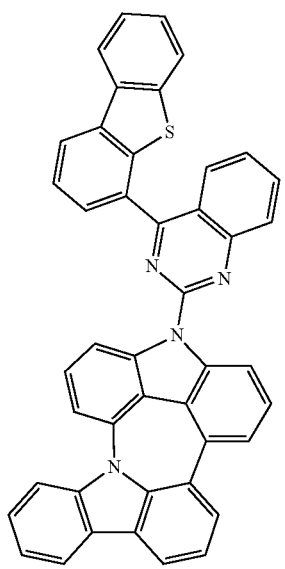

C-9
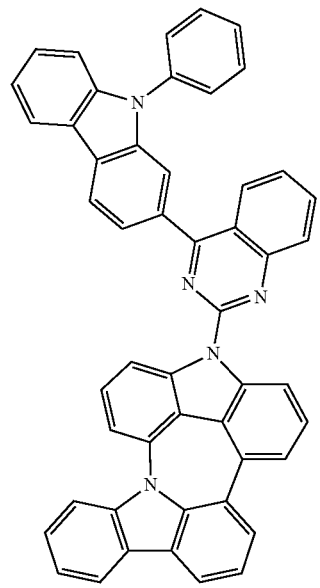
C-10
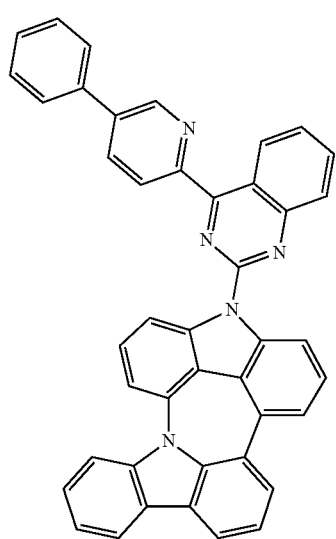
C-11
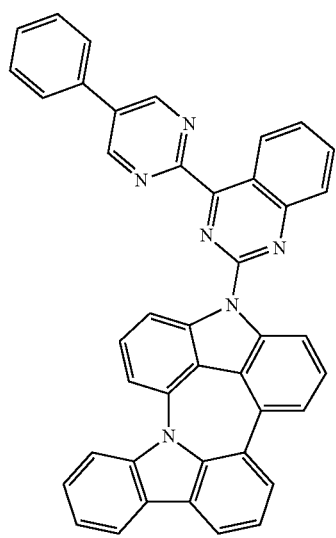
C-12
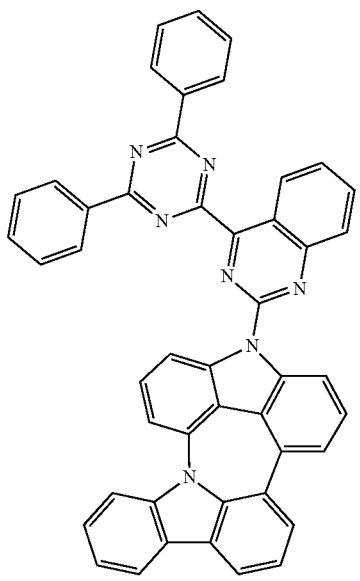
C-13
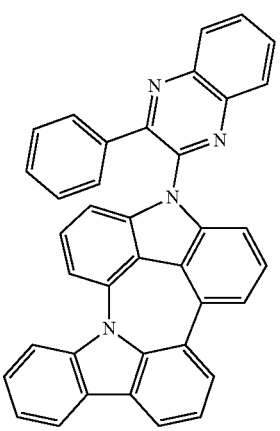
C-14
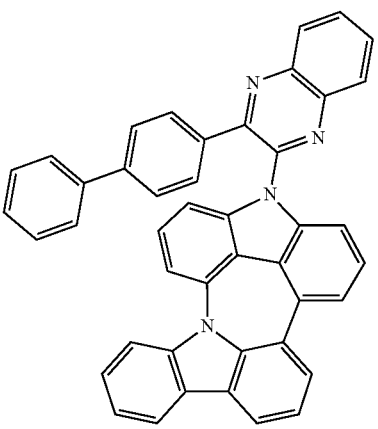

-continued
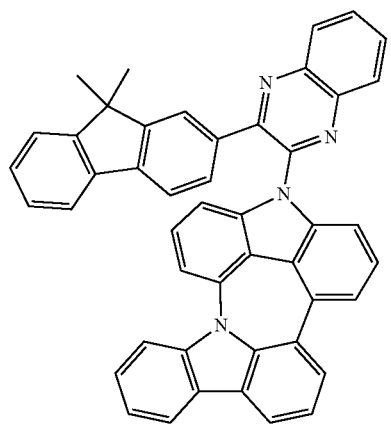
C-15
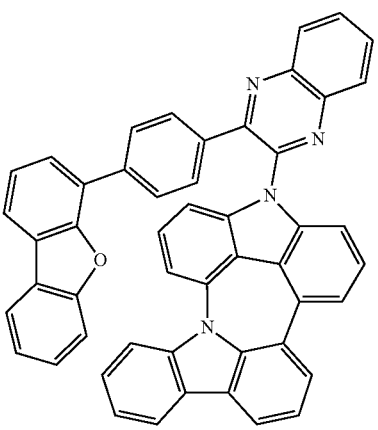
C-18
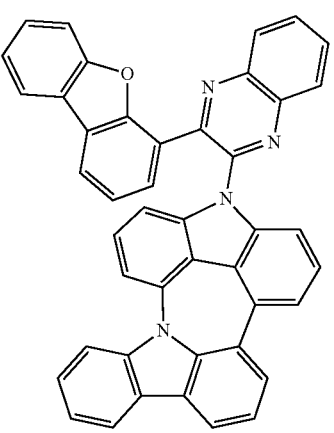
C-19
C-16
C-17
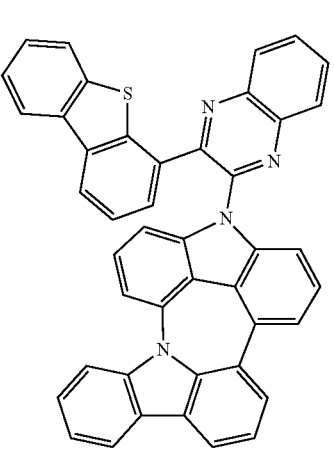
C-20

C-21
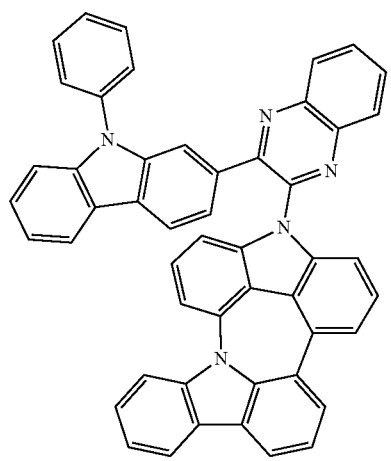
C-22
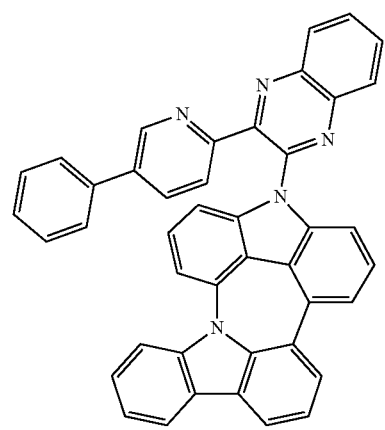
C-23
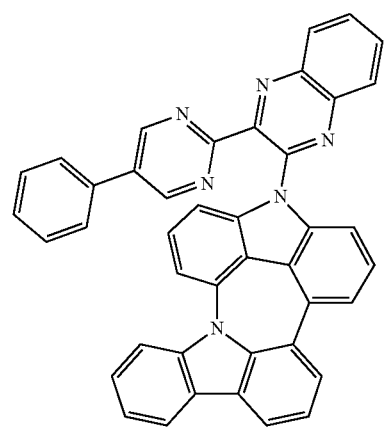
C-24
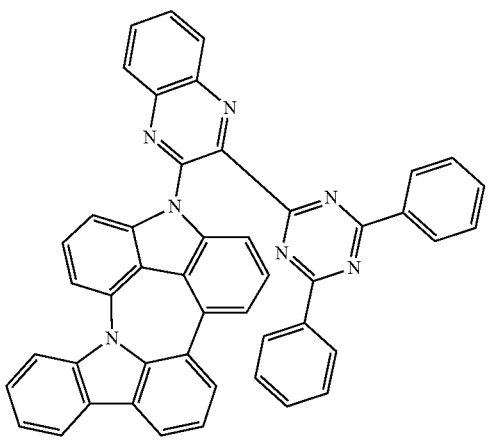
C-25
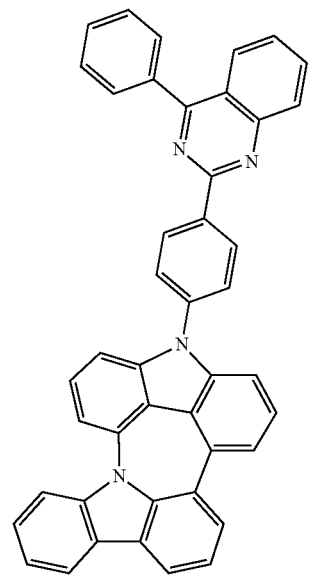
C-26
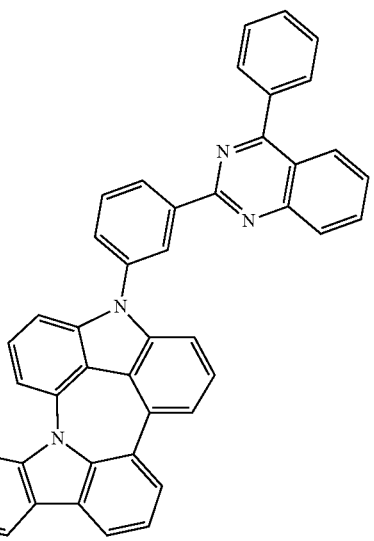

-continued
C-27
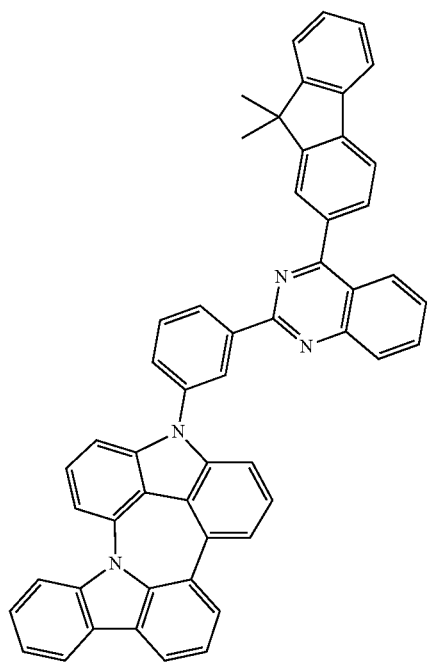
C-29
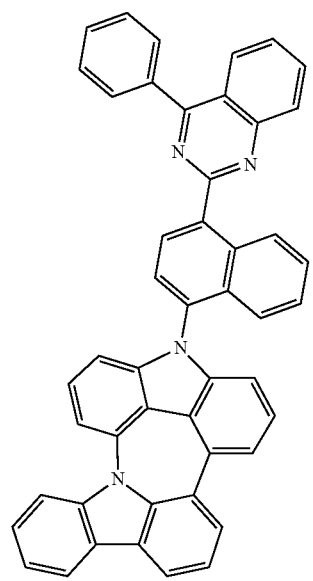
C-28
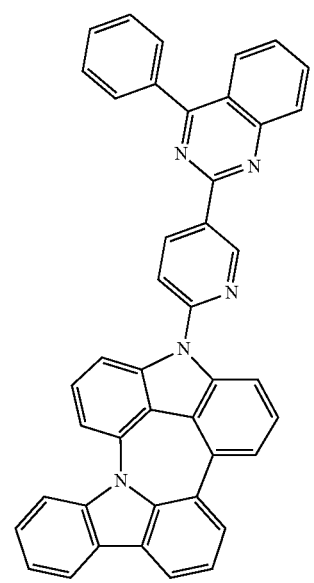
C-30
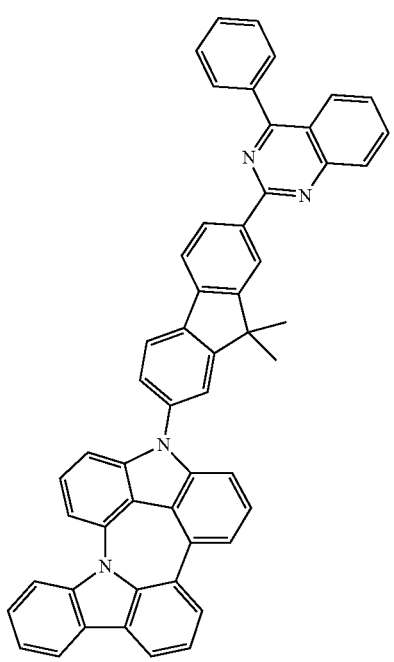

-continued
C-31
C-32
C-33
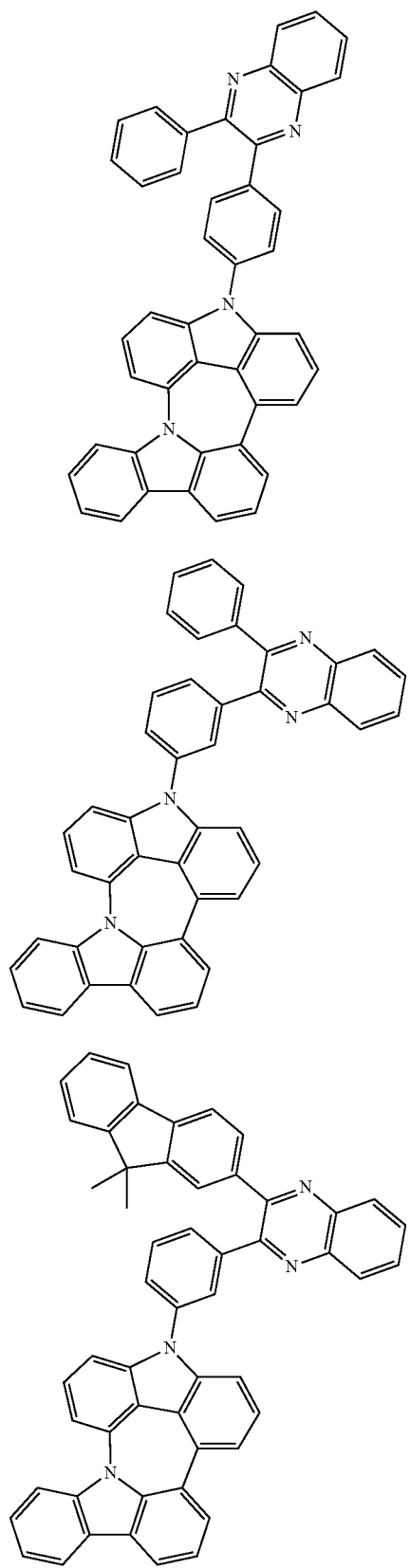
C-34
C-35

C-36
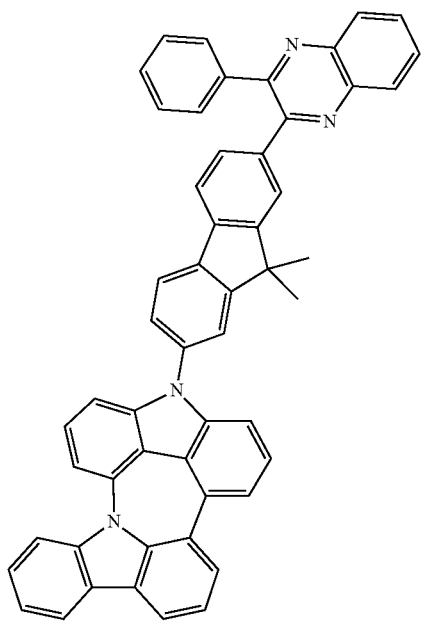
C-37
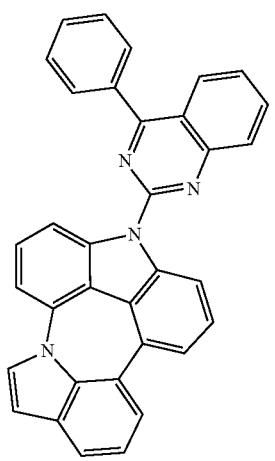
C-38
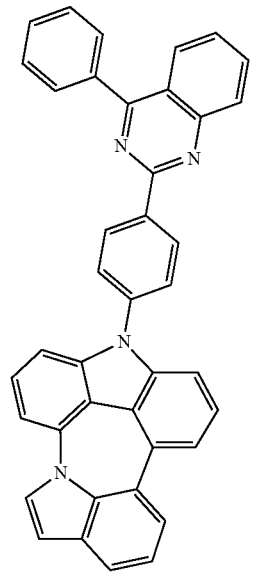
C-39
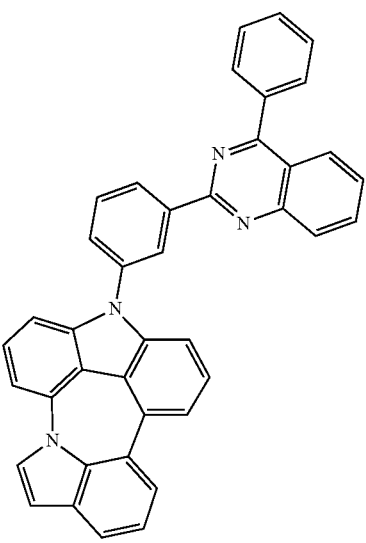
C-40
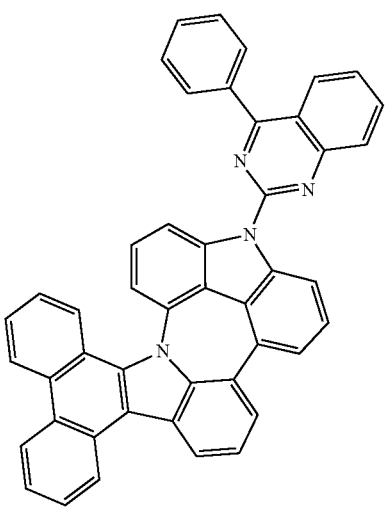

-continued
C-41
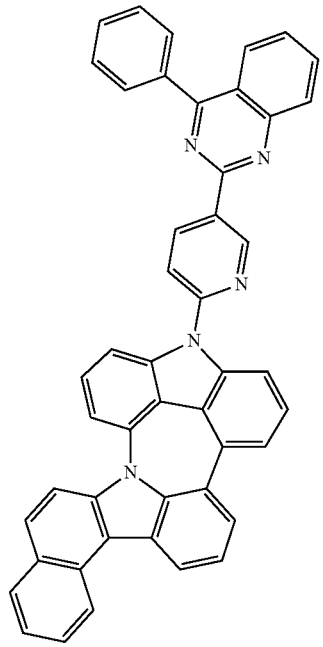
C-42
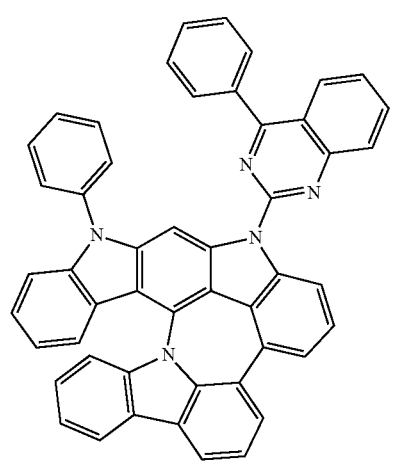
C-43
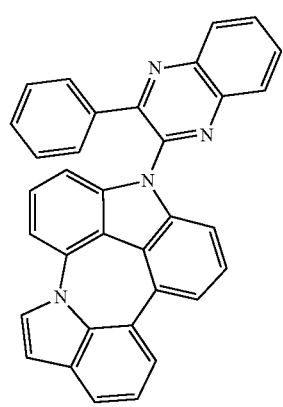
C-44
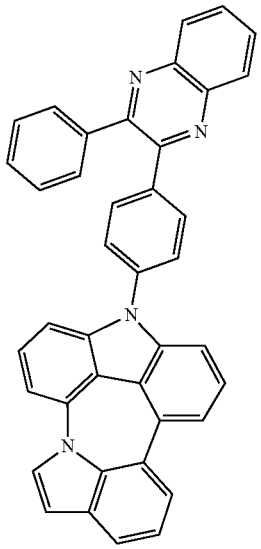
C-45
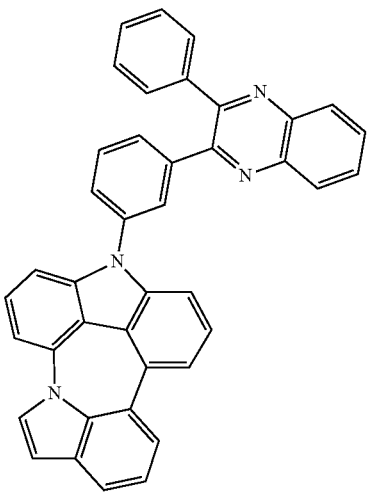
C-46
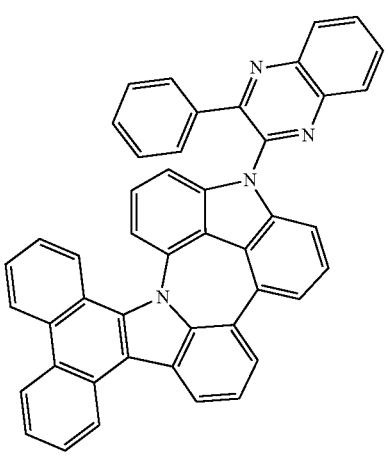

-continued
C-47
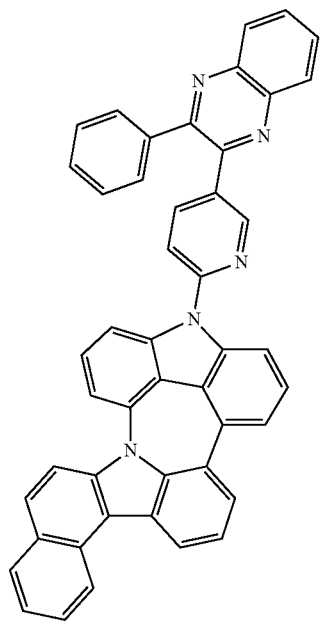
C-48
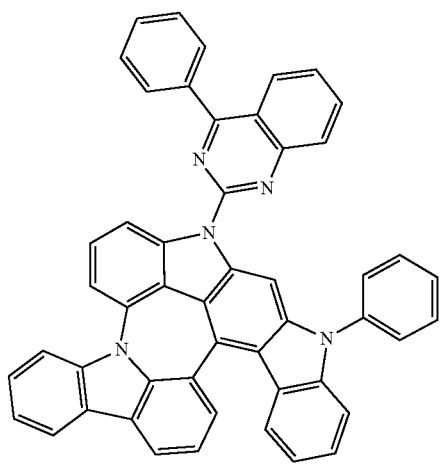
C-49
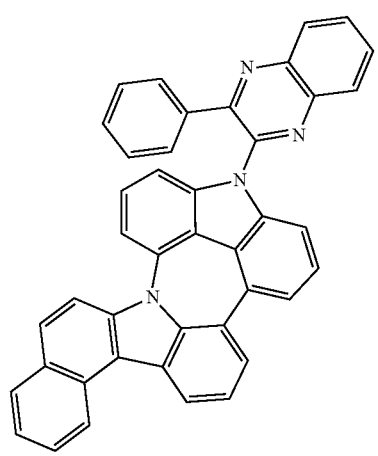
-continued
C-50
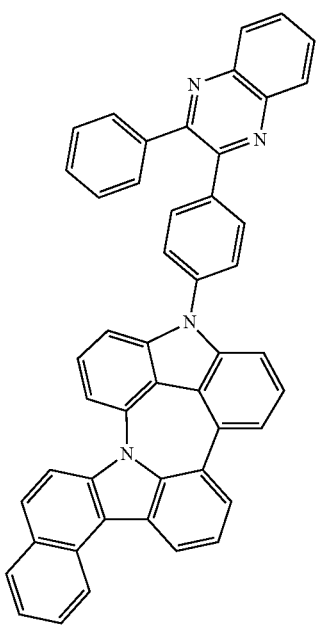
C-51
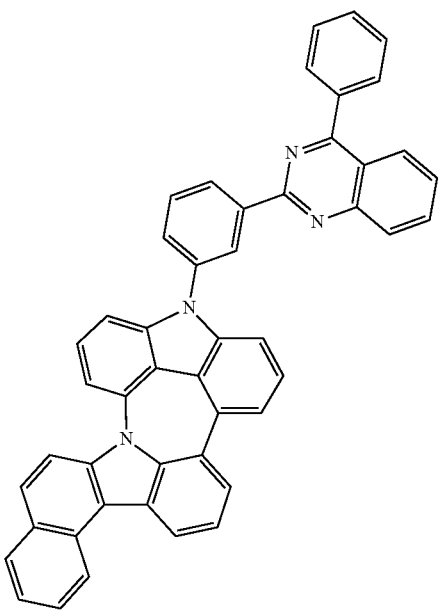

C-52
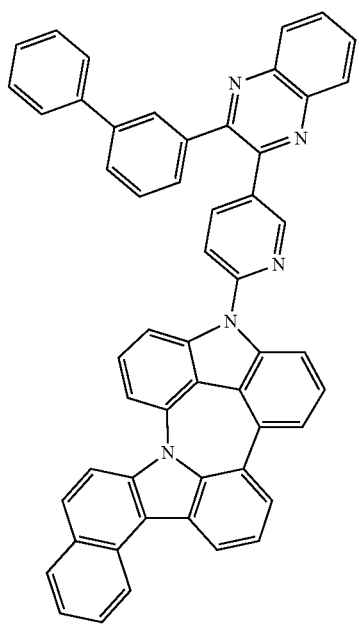
C-53
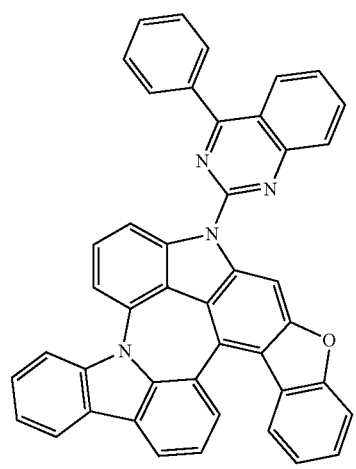
C-54
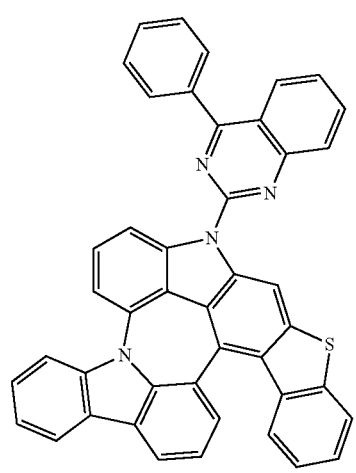
C-55
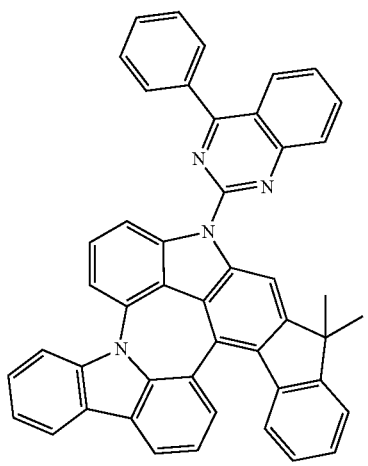
C-56
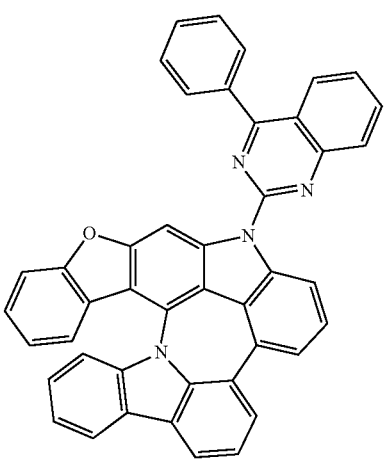
C-57
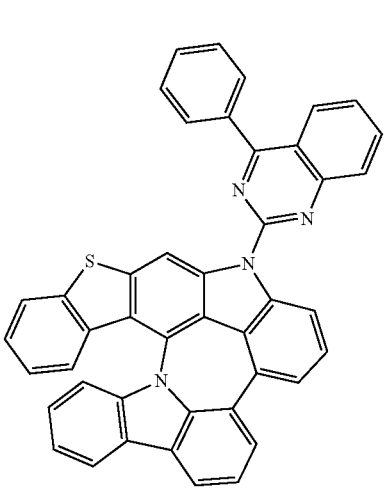

-continued
C-58
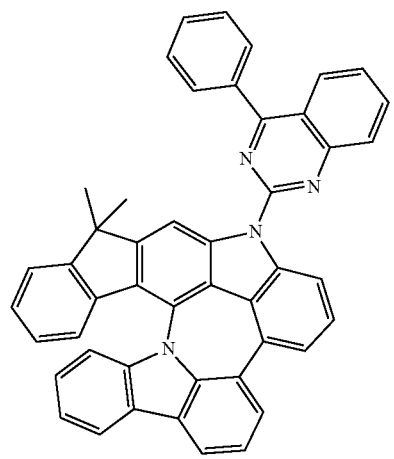
C-59
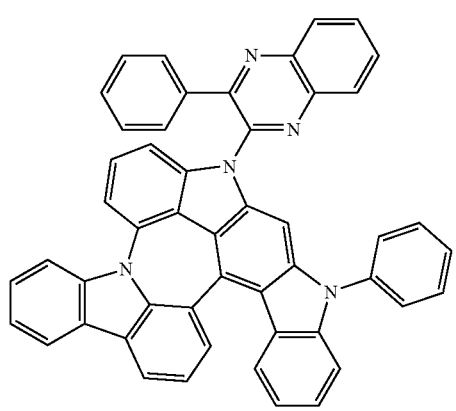
C-60
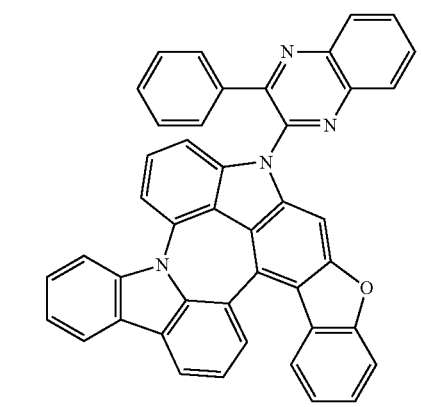
-continued
C-61
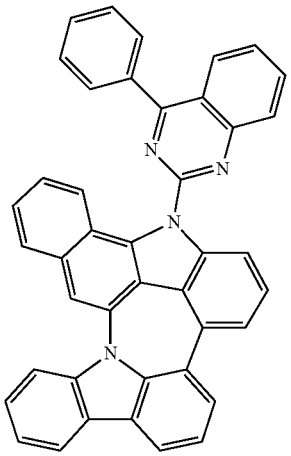
C-62
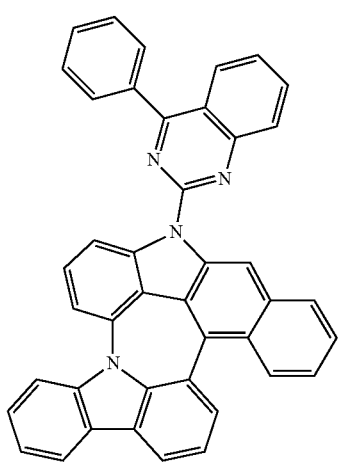
C-63
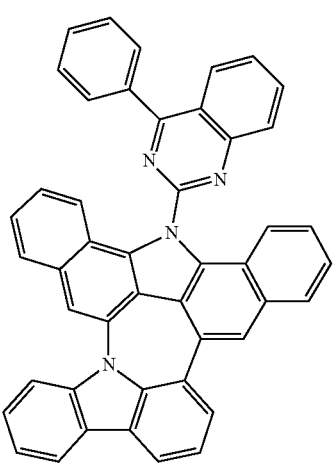

33
-continued
C-64
C-65
C-66
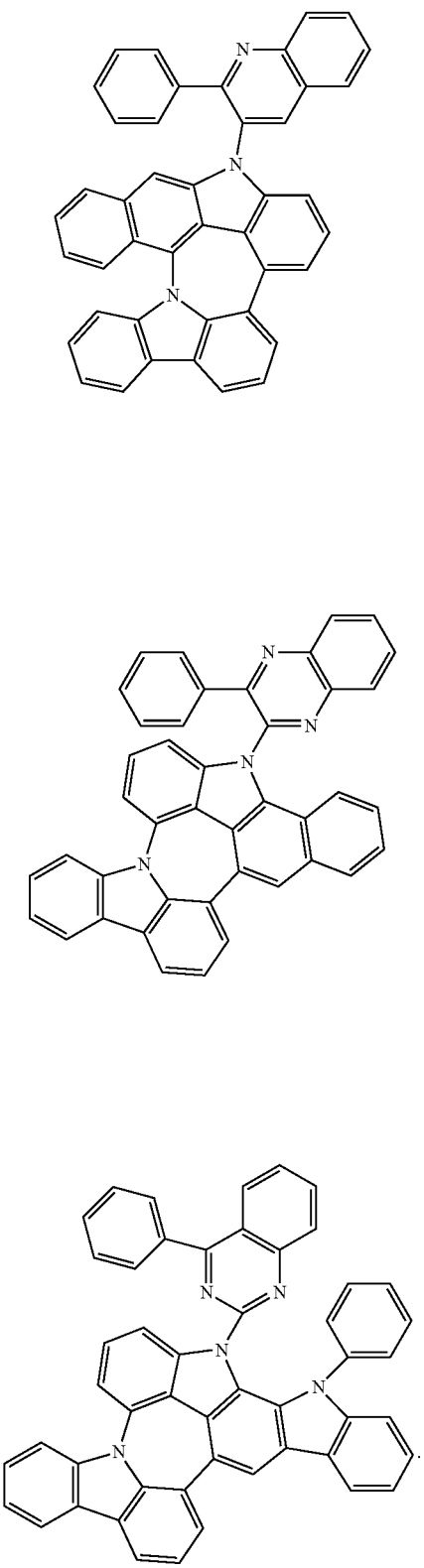
The organic electroluminescent compound of the present disclosure can be prepared by a synthetic method known to one skilled in the art. For example, it can be prepared according to the following reaction scheme 1.
[Reaction Scheme 1]
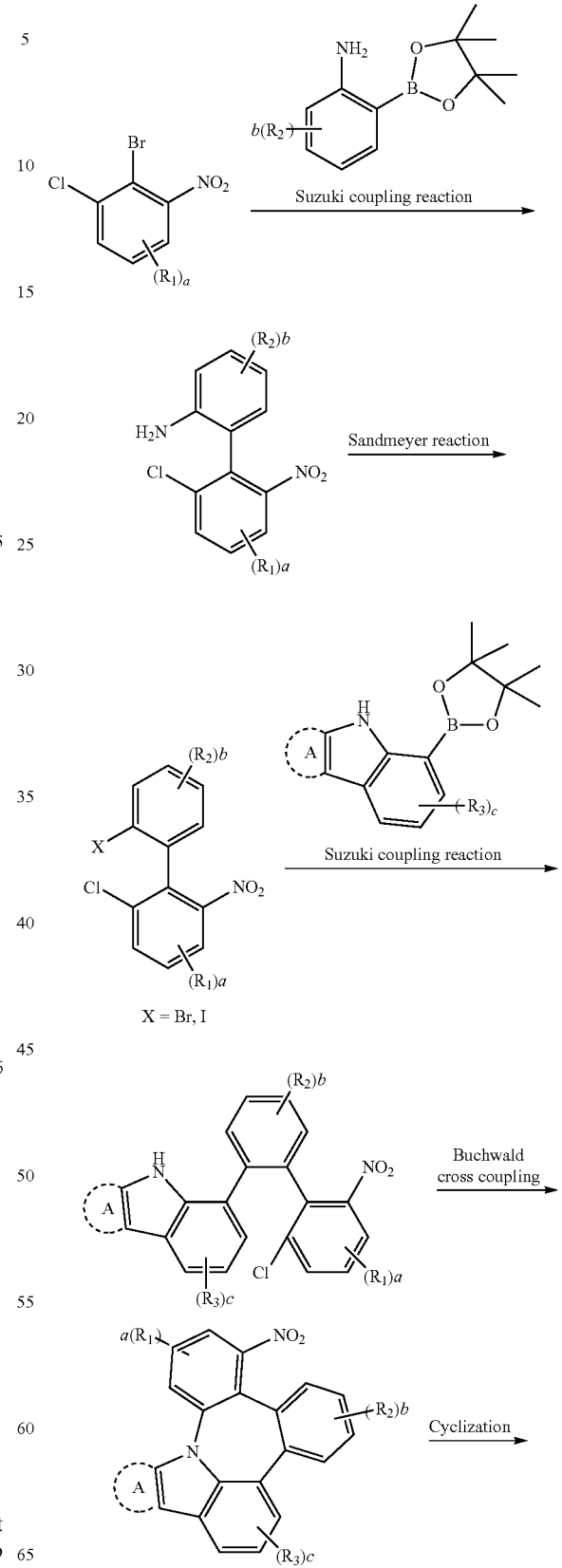

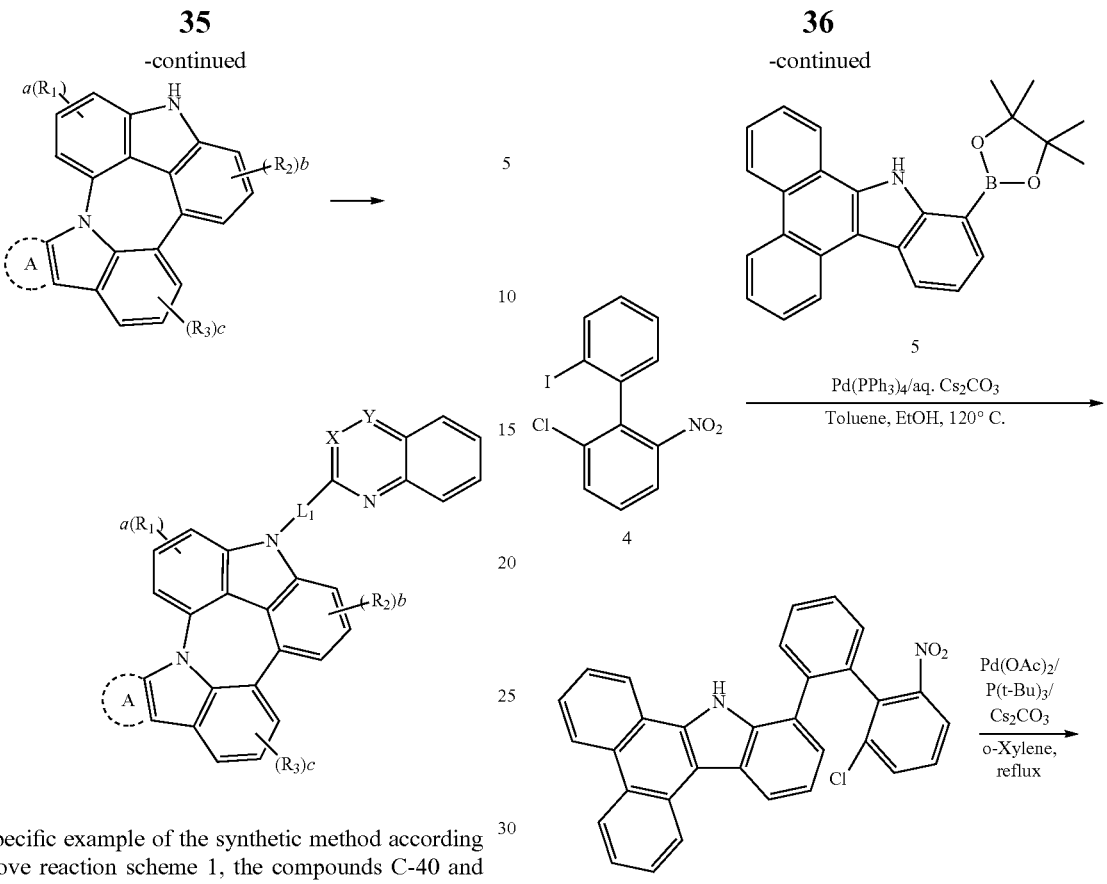
As a specific example of the synthetic method according to the above reaction scheme 1, the compounds C-40 and C-66 of the present disclosure can be prepared according to the following reaction schemes 2 and 3.
[Reaction Scheme 2]
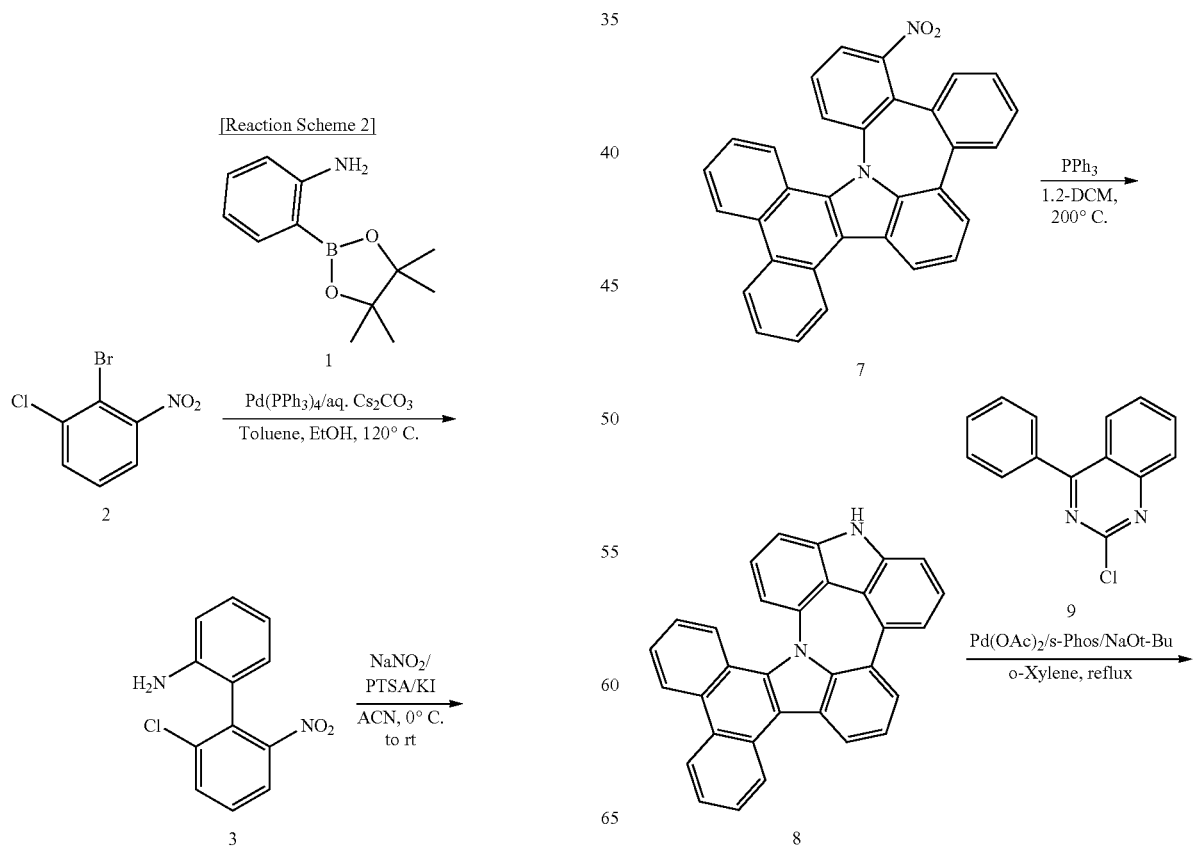

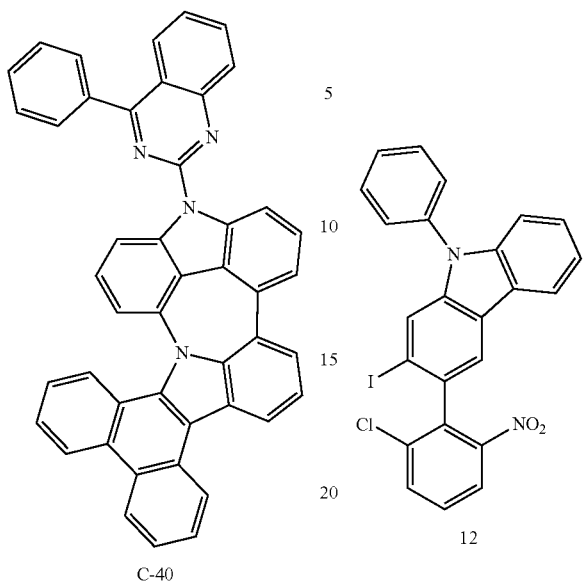
C-40
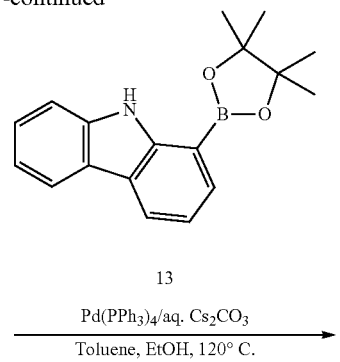
[Reaction Scheme 3]
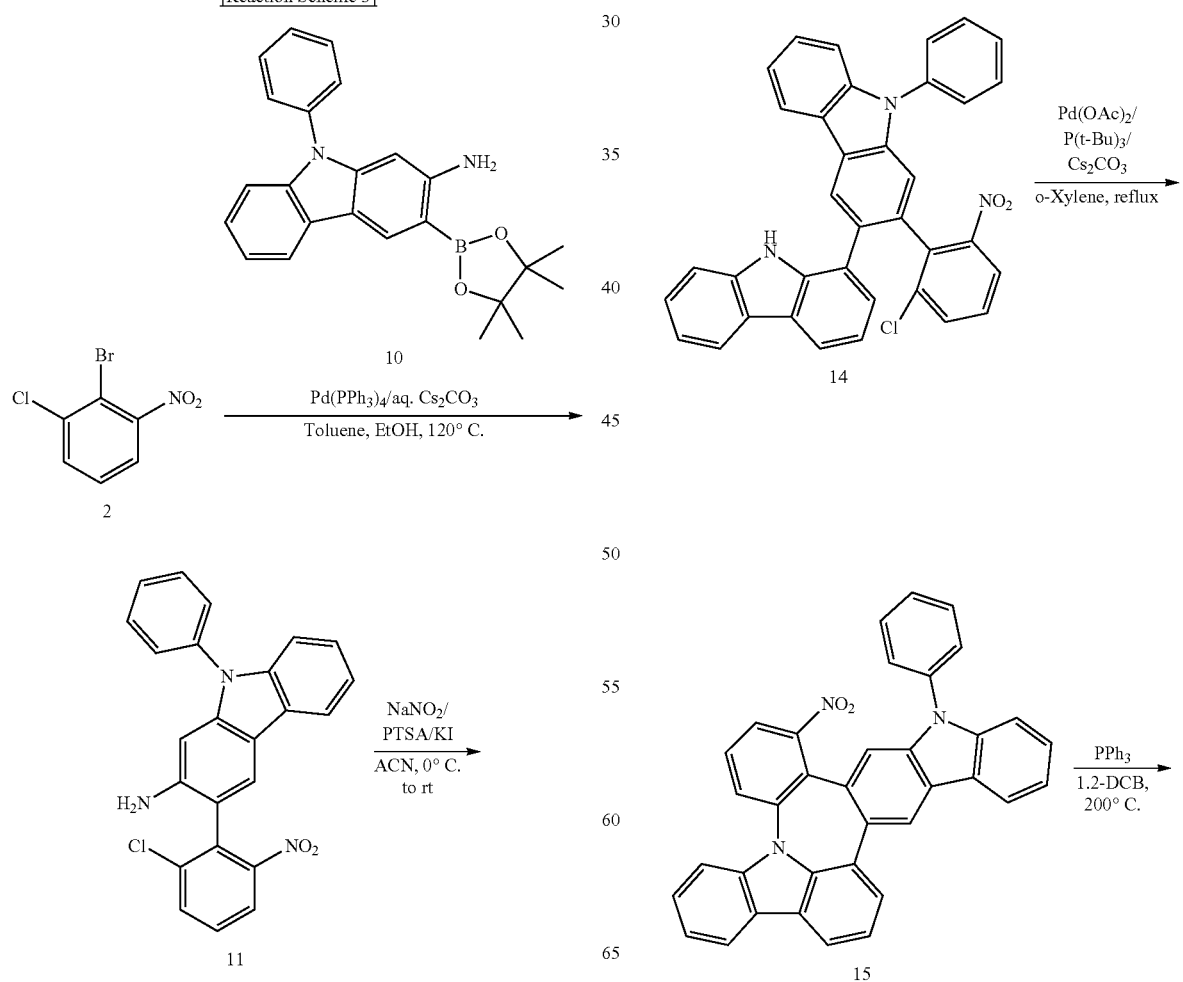

-continued

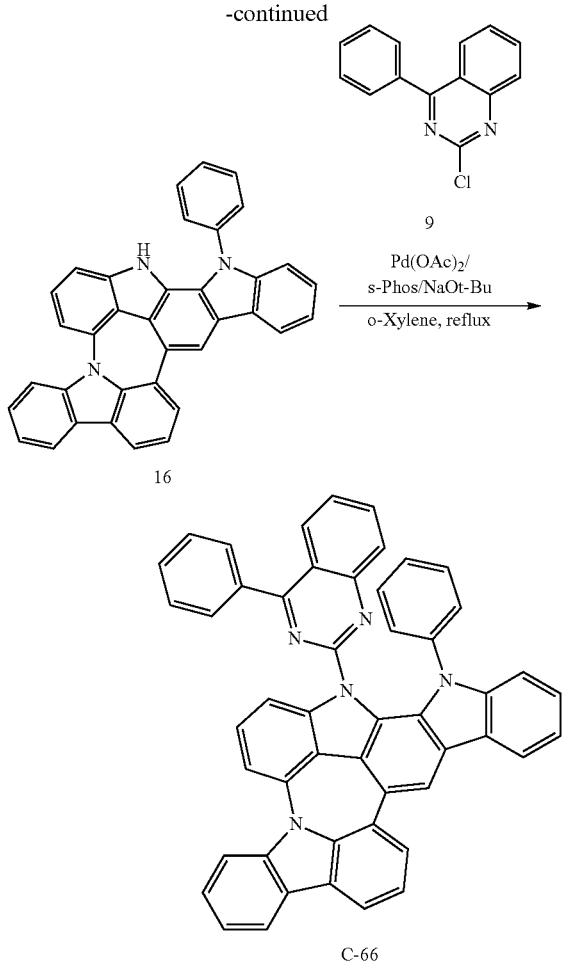

In the above reaction scheme 1, X, Y, L$_1$, A, R$_1$ to R$_3$, and a, b, and c are as defined in formula 1 above.

Furthermore, the present disclosure provides an organic electroluminescent material comprising the organic electroluminescent compound of formula 1, and an organic electroluminescent device comprising the material.

The material may consist of the organic electroluminescent compound of the present disclosure. Otherwise, the material may further comprise a conventional compound(s) which has been comprised for an organic electroluminescent material, in addition to the compound of the present disclosure.

The organic electroluminescent device may comprise a first electrode, a second electrode, and at least one organic layer disposed between the first and second electrodes. The organic layer may comprise at least one compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, an auxiliary light-emitting layer, an electron transport layer, an electron injection layer, an interlayer, a hole blocking layer, an electron blocking layer, and an electron buffering layer, wherein the auxiliary light-emitting layer is disposed between the anode and the light-emitting layer or between the cathode and the light-emitting layer; the auxiliary light-emitting layer may be used to facilitate injection and/or transport of holes or to block overflow of electrons when it is disposed between the anode and the light-emitting layer, or the auxiliary light-emitting layer may be used to facilitate injection and/or transport of electrons or to block overflow of holes when it is disposed between the cathode and the light-emitting layer. In addition, the hole auxiliary layer is disposed between the hole transport layer (or the hole injection layer) and the light-emitting layer and shows the effect to increase the hole transport speed (or the hole injection speed) or to block holes, and thereby, may control charge balance. Furthermore, an electron blocking layer is disposed between the hole transport layer (or the hole injection layer) and the light-emitting layer and blocks electron overflow from the light-emitting layer to trap excitons within the light-emitting layer, and thereby, to prevent light leakage. When two or more hole transport layers are included, the additional hole transport layer may be used as the hole auxiliary layer or the electron blocking layer. The hole auxiliary layer and the electron blocking layer have the effects to provide improvement in efficiency and lifespan of the organic electroluminescent device.

The organic electroluminescent compound of formula 1 of the present disclosure may be comprised in the light-emitting layer. When used in the light-emitting layer, the organic electroluminescent compound of formula 1 of the present disclosure may be comprised as a host material. Preferably, the light-emitting layer may further comprise at least one dopant. If needed, it may comprise a compound other than the organic electroluminescent compound of formula 1 of the present disclosure as a second host material. The weight ratio between the first host material and the second host material is in the range of 1:99 to 99:1.

The second host material may be from any of the known phosphorescent host materials. Specifically, the compound selected from the group consisting of the compounds of formulae 11 to 16 below is preferable as the second host material in view of luminous efficiency:

(11)

(12)

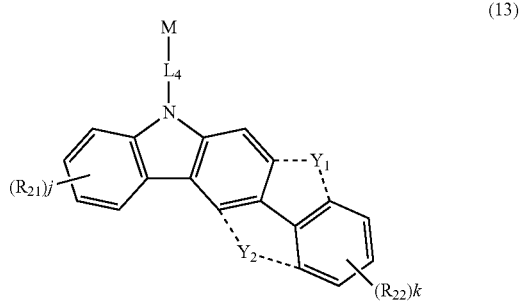

(13)

(14)

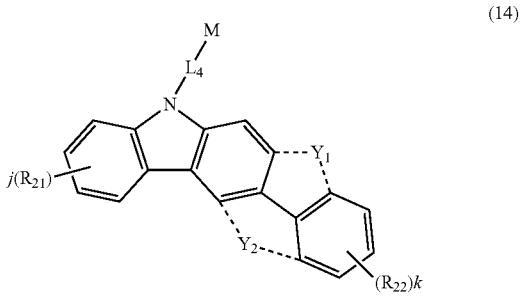

-continued

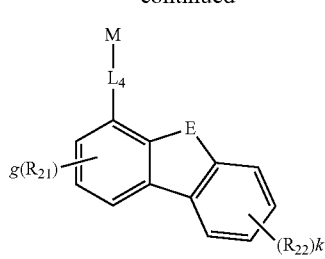
(15)

Wherein, Cz represents the following structure:

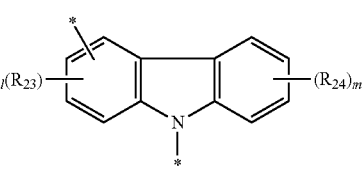

E represents —O— or —S—;
$R_{21}$ to $R_{24}$ each independently, represent hydrogen, deuterium, a halogen, a substituted or unsubstituted (C1-C30) alkyl, a substituted or unsubstituted (C6-C30)aryl, a substituted or unsubstituted (5 to 30-membered) heteroaryl or —$SiR_{25}R_{26}R_{27}$; $R_{25}$ to $R_{27}$, each independently, represent a substituted or unsubstituted (C1-C30)alkyl, or a substituted or unsubstituted (C6-C30)aryl; La represents a single bond, a substituted or unsubstituted (C6-C30)arylene, or a substituted or unsubstituted (5 to 30-membered) heteroarylene; M represents a substituted or unsubstituted (C6-C30)aryl, or a substituted or unsubstituted (5 to 30-membered) heteroaryl; $Y_1$ and $Y_2$ each independently, represent —O—, —S—, —$N(R_{31})$— or —$C(R_{32})(R_{33})$—, and $Y_1$ and $Y_2$ do not occur concurrently; $R_{31}$ to $R_{33}$, each independently, represent a substituted or unsubstituted (C1-C30)alky, a substituted or unsubstituted (C6-C30)aryl, or a substituted or unsubstituted (5 to 30-membered) heteroaryl, $R_{32}$ and $R_{33}$ may be the same or different; h and i, each independently, represent an integer of 1 to 3; g represents an integer of 0 to 3; j, k, l, and m, each independently, represent an integer of 0 to 4; when g, h, i, j, k, l, or m is an integer of 2 or more, each of (Cz-$L_4$), each of (Cz), each of $R_{21}$, each of $R_{22}$, each of $R_{23}$ or each of $R_{24}$ may be the same or different;

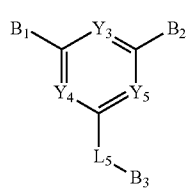
(16)

wherein
$Y_3$ to $Y_5$, each independently, represent $CR_{34}$ or N;
$R_{34}$, each independently, represent hydrogen, a substituted or unsubstituted (C1-C30)alkyl, a substituted or unsubstituted (C6-C30)aryl, or a substituted or unsubstituted (5 to 30-membered)heteroaryl;
$B_1$ and $B_2$, each independently, represent hydrogen, a substituted or unsubstituted (C6-C30)aryl, or a substituted or unsubstituted (5 to 30-membered)heteroaryl;

$B_3$ represents a substituted or unsubstituted (C6-C30)aryl, or a substituted or unsubstituted (5 to 30-membered)heteroaryl; and
$L_5$ represents a single bond or a substituted or unsubstituted (C6-C30)arylene, or a substituted or unsubstituted (5 to 30-membered)heteroarylene.

Specifically, the second host material includes the following:

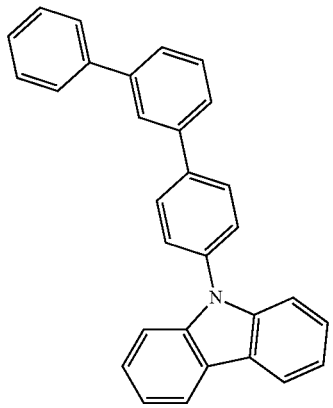
B-1

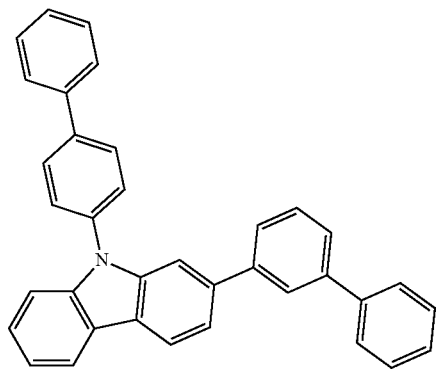
B-2

B-3

B-4
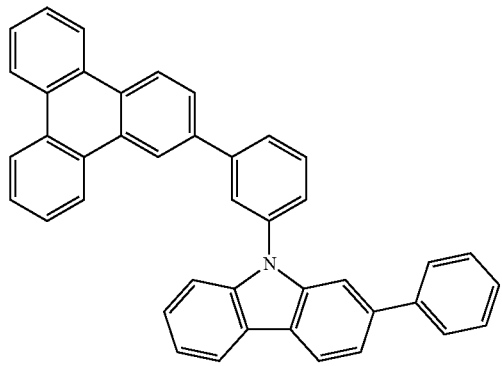
B-5
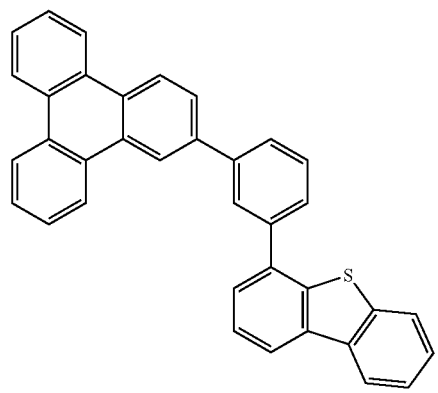
B-6
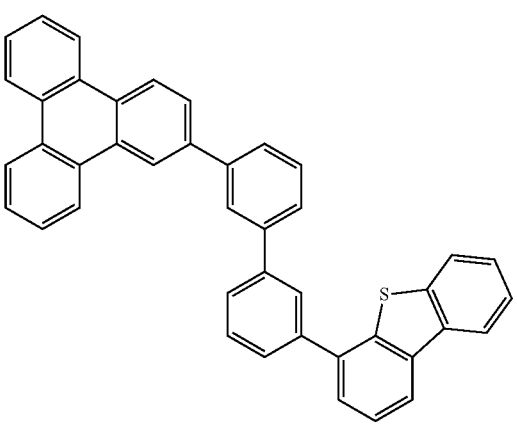
B-7
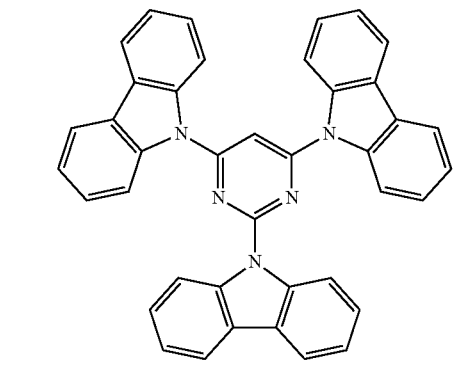
B-8
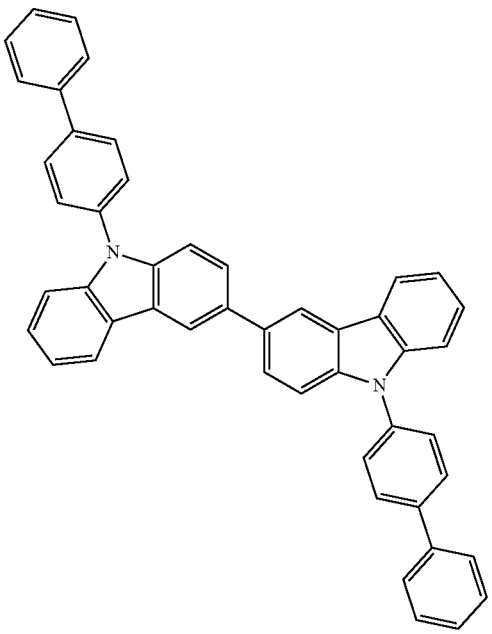
B-9
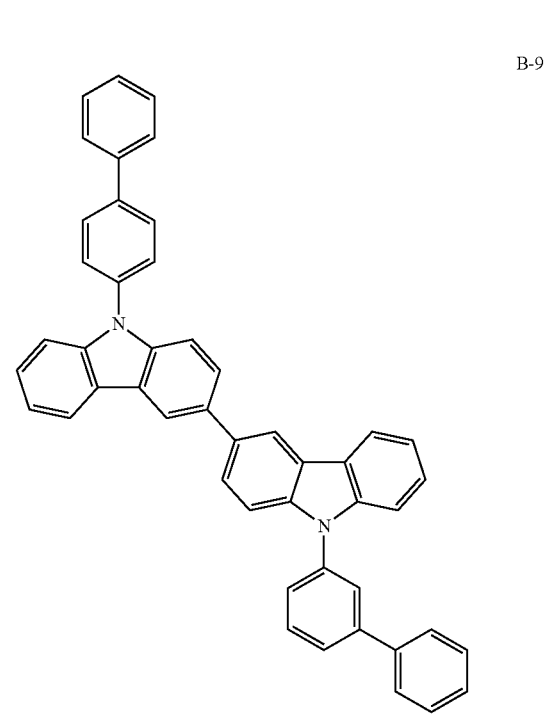

B-10
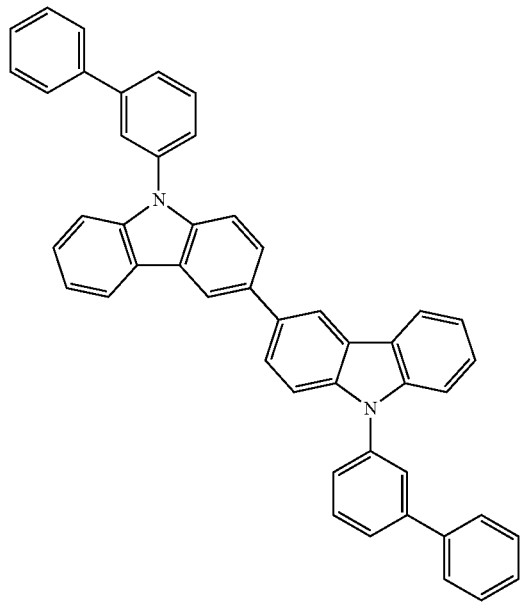
B-11
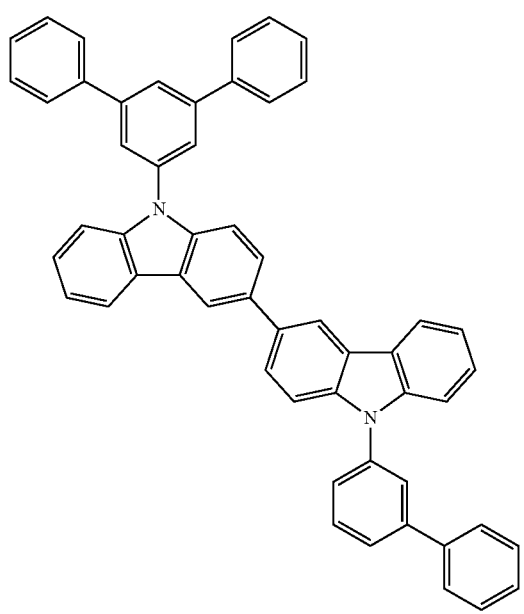
B-12
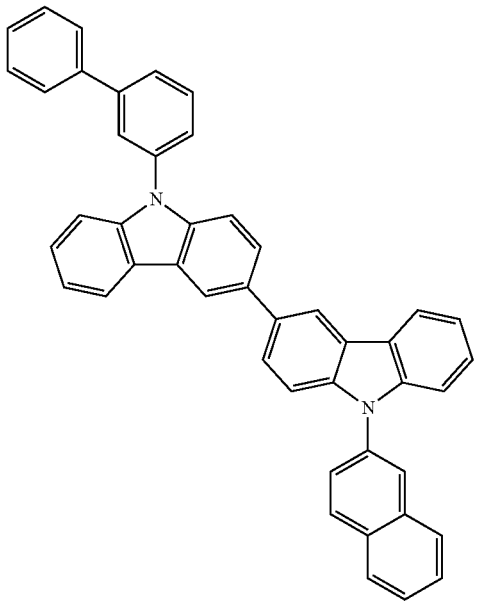
B-13
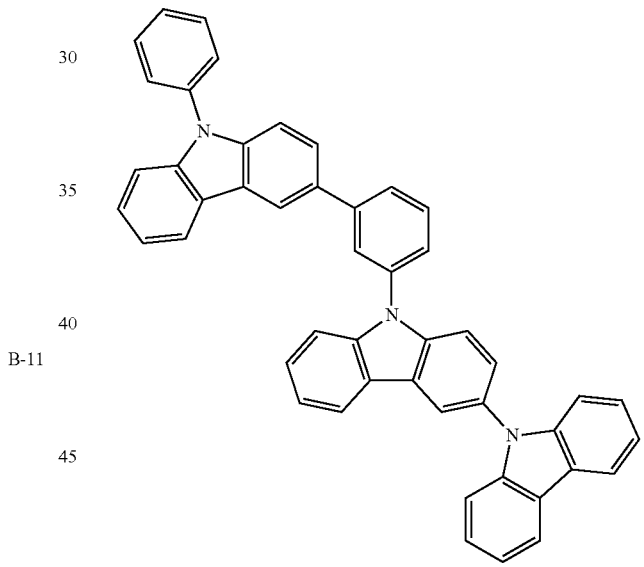
B-14
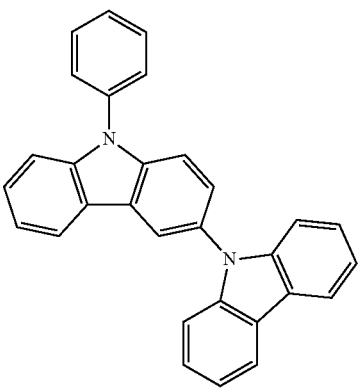

B-15
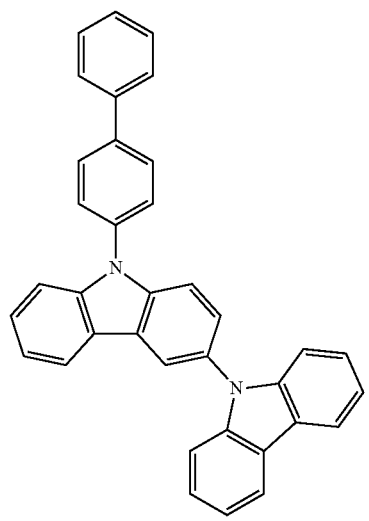
B-18
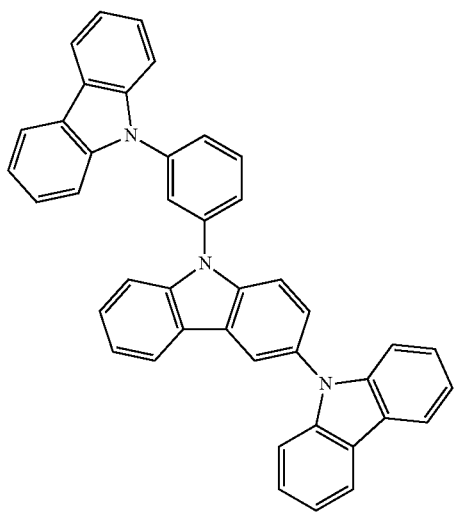
B-16
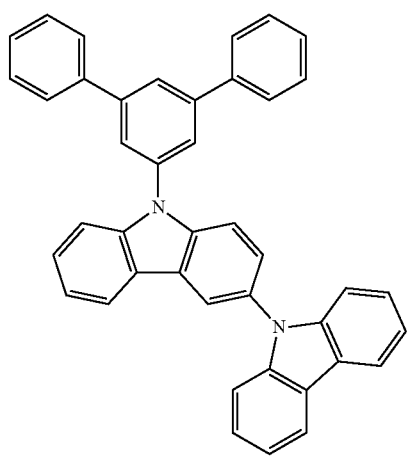
B-19
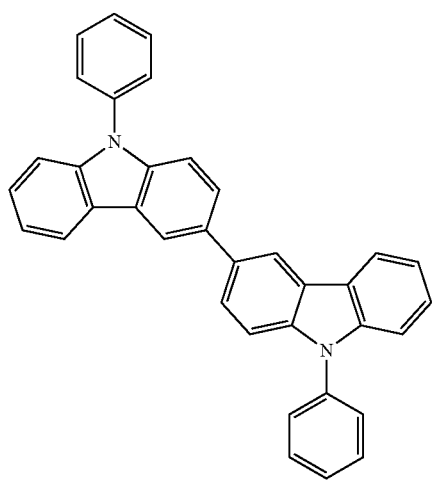
B-17
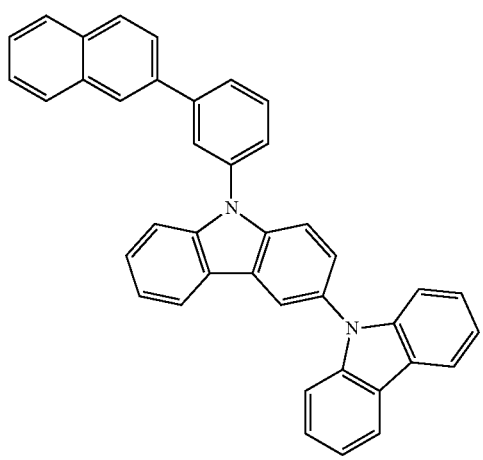
B-20
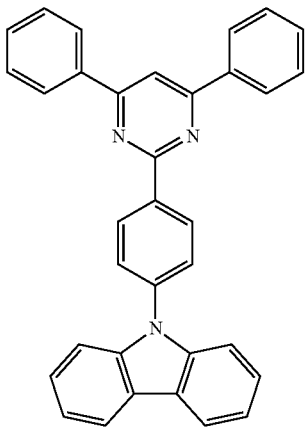

B-21
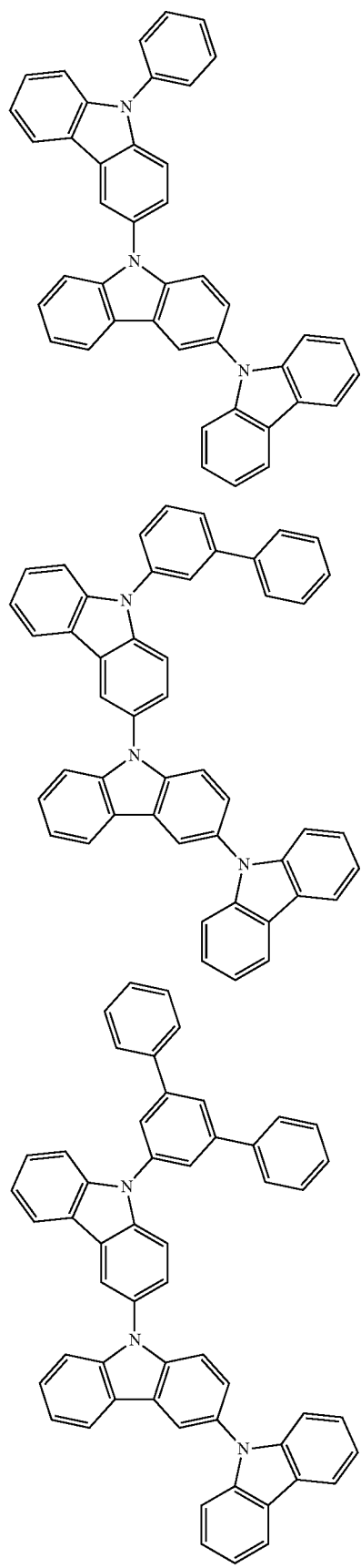
B-22
B-23
B-24
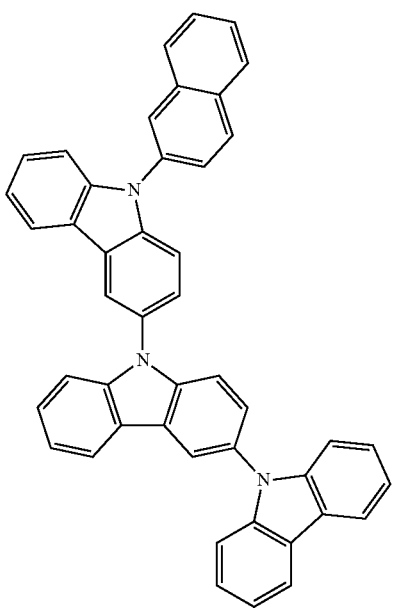
B-25
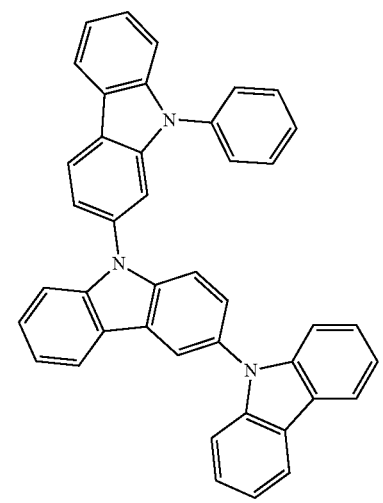
B-26
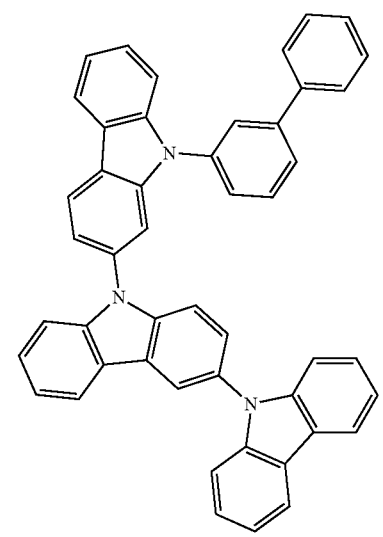

B-27
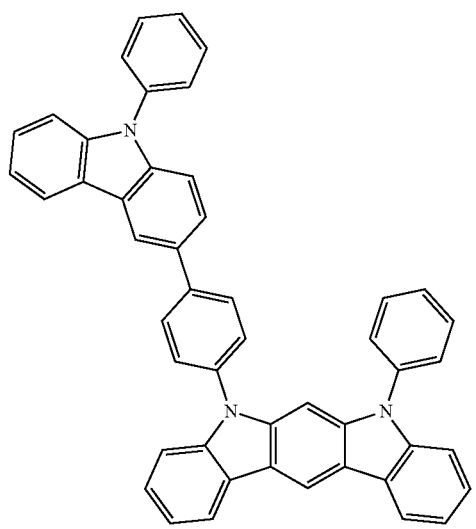
B-28
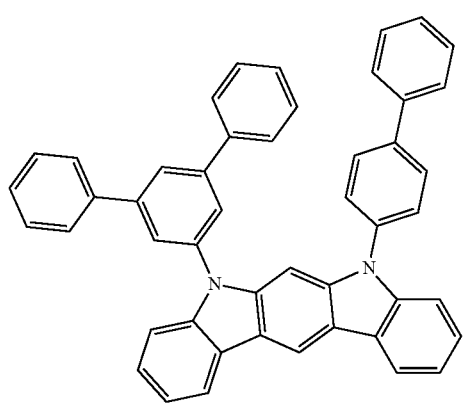
B-29
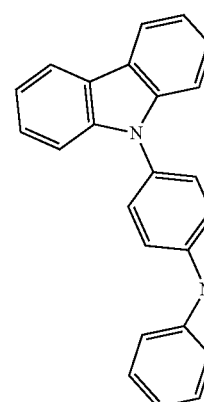
B-30
B-31
B-32
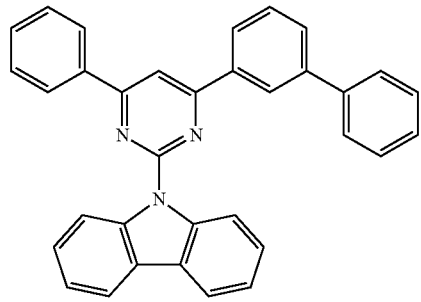
B-33
B-34
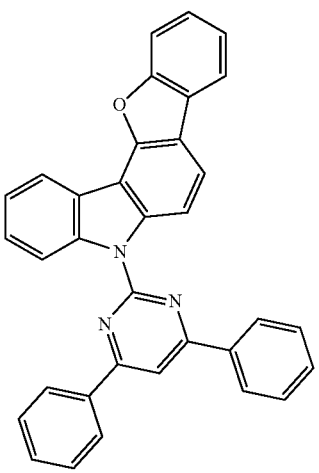

B-35
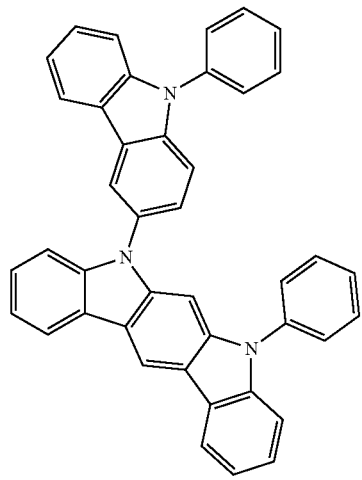
B-36
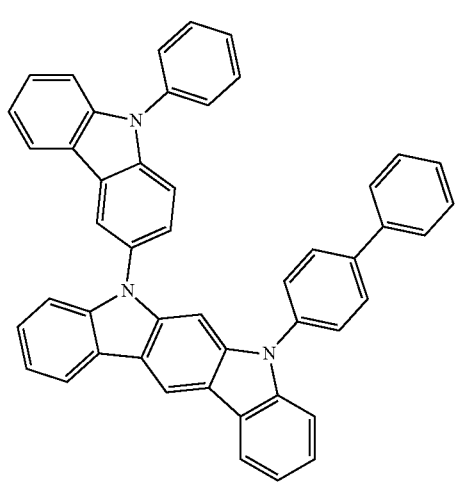
B-37
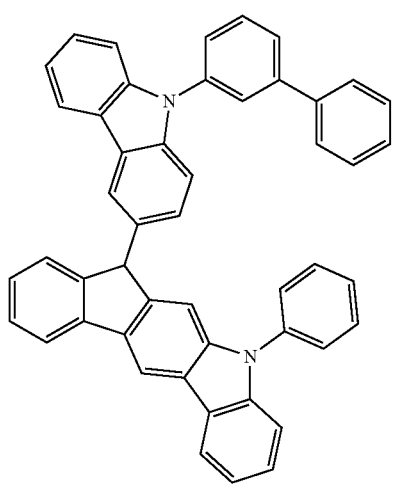
B-38
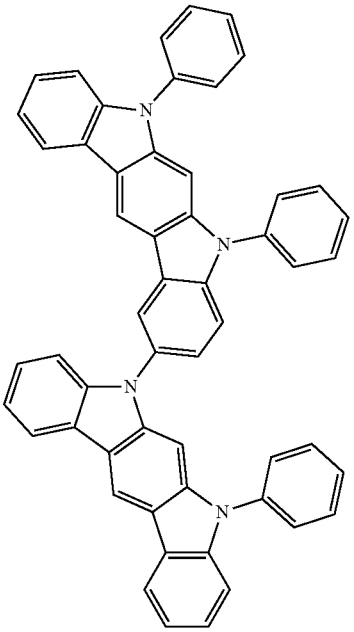
B-39
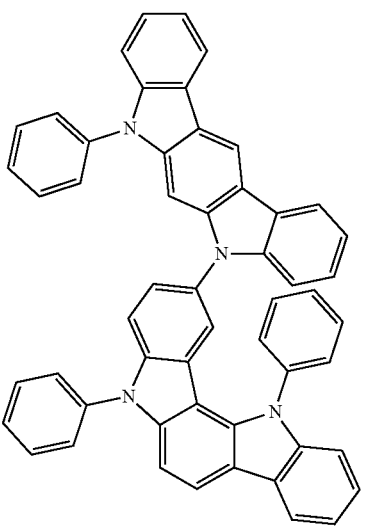
B-40
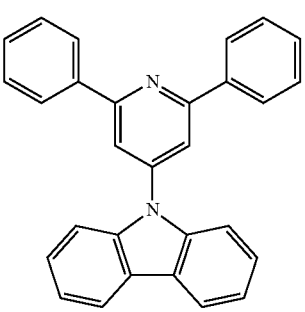

B-41
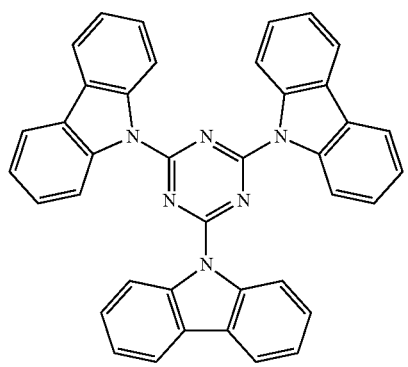
B-42
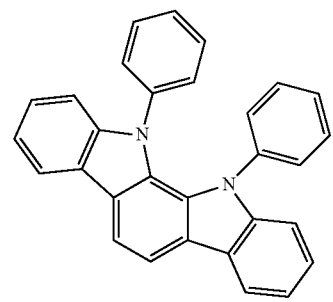
B-43
B-44
B-45
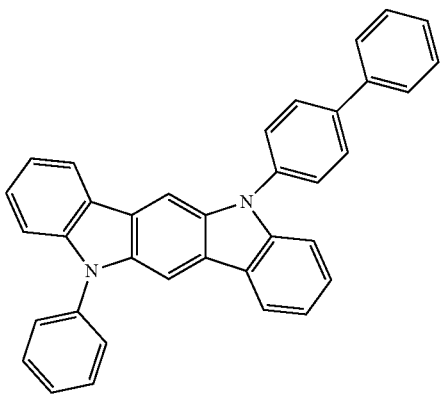
B-46
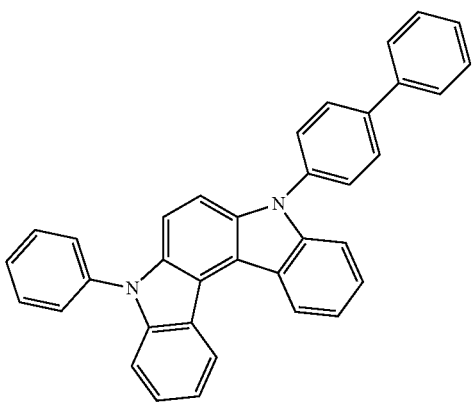
B-47
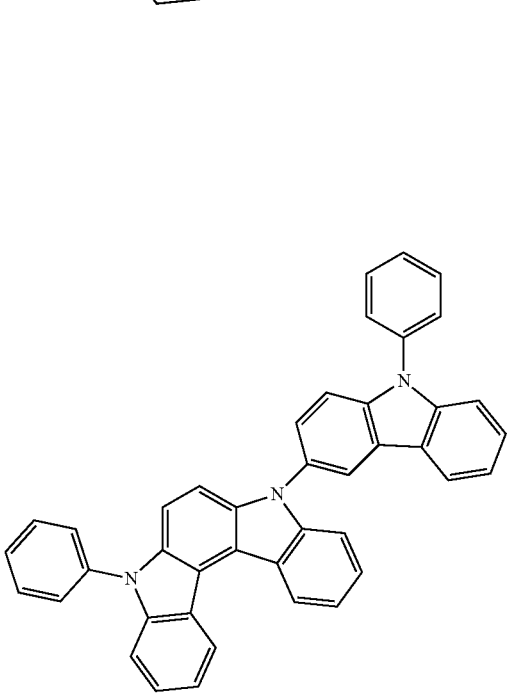

B-48
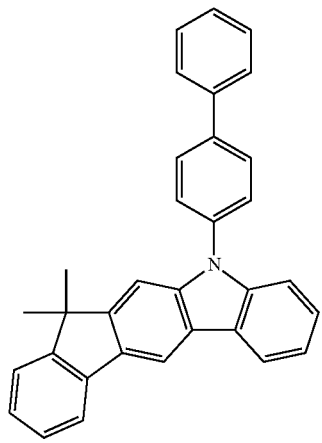
B-49
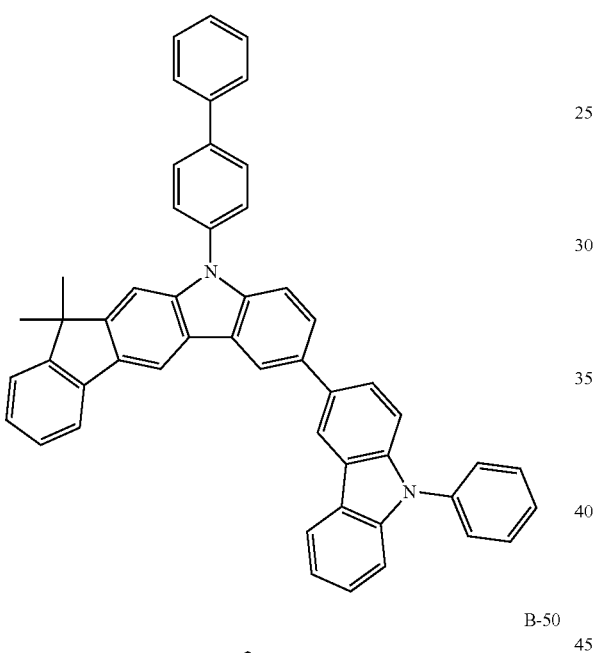
B-50
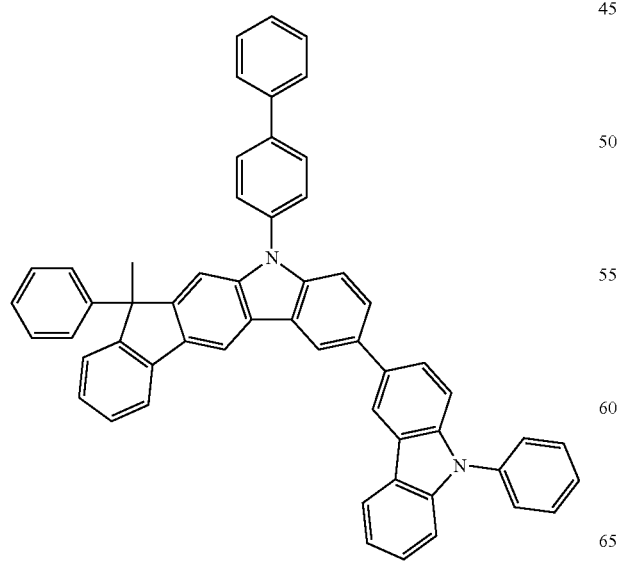
B-51
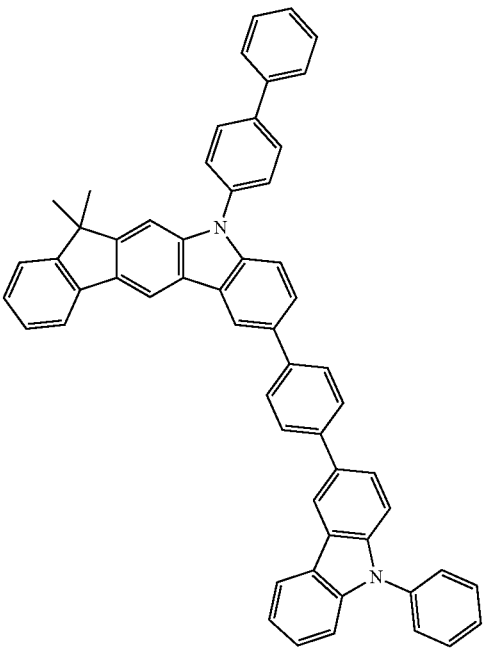
B-52
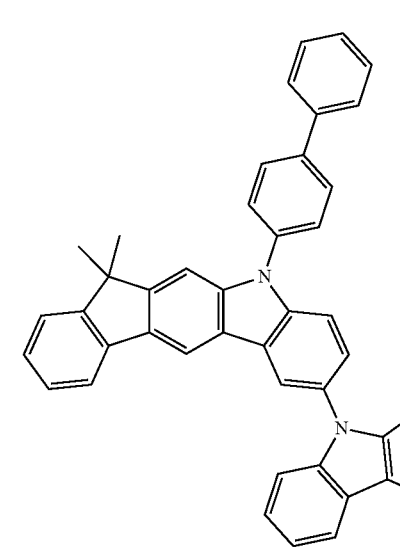

B-53
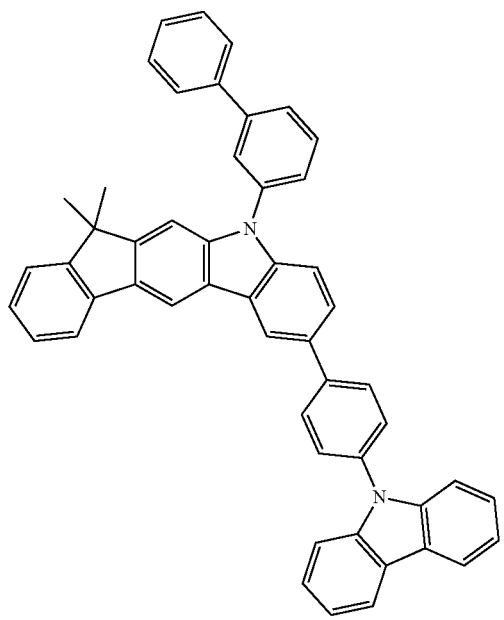
B-54
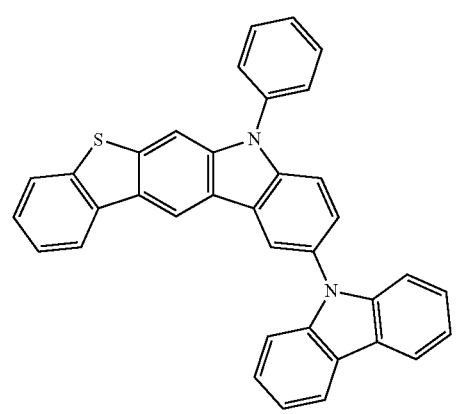
B-55
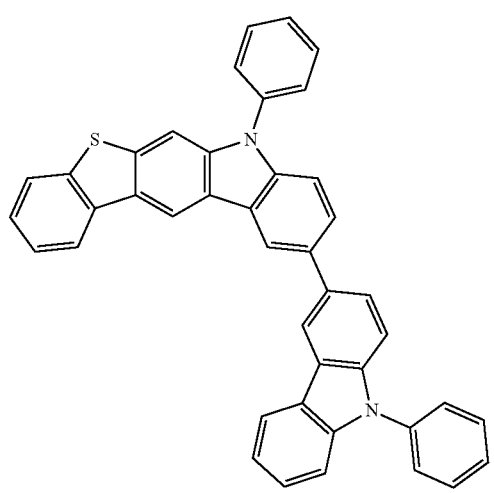
B-56
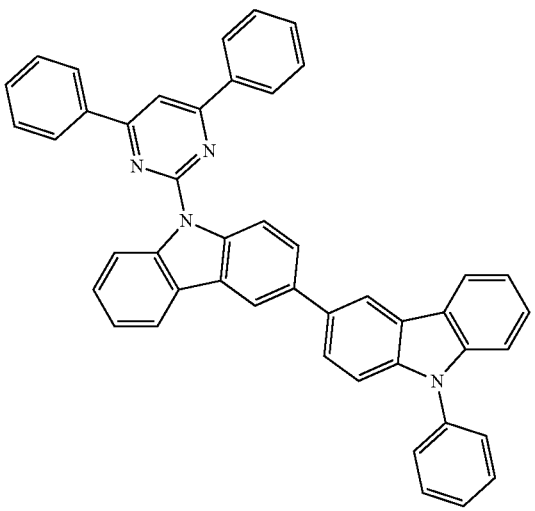
B-57
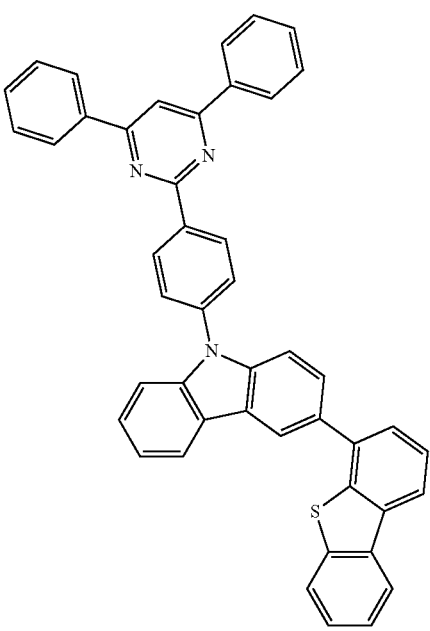
B-58
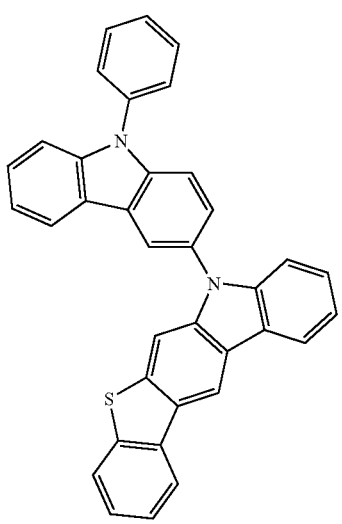

B-59
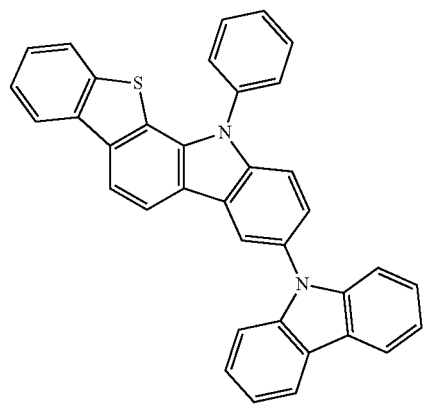
B-60
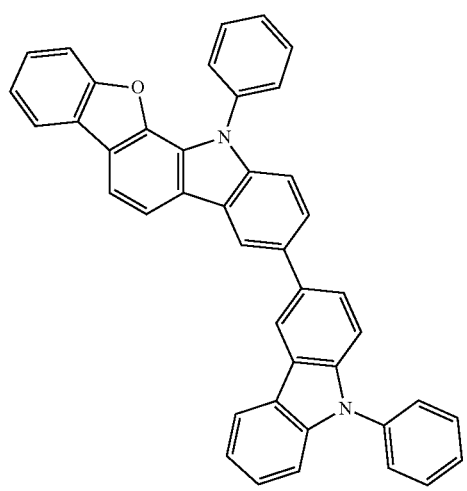
B-61
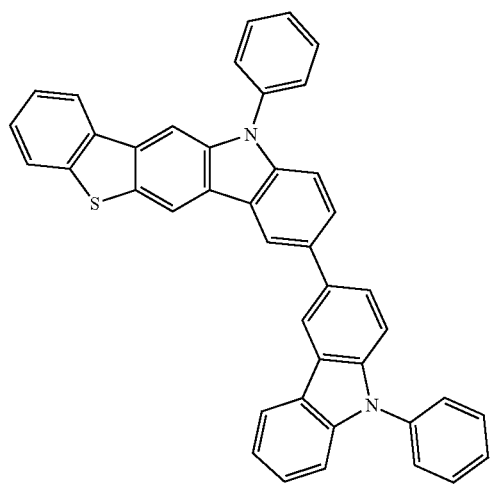
B-62
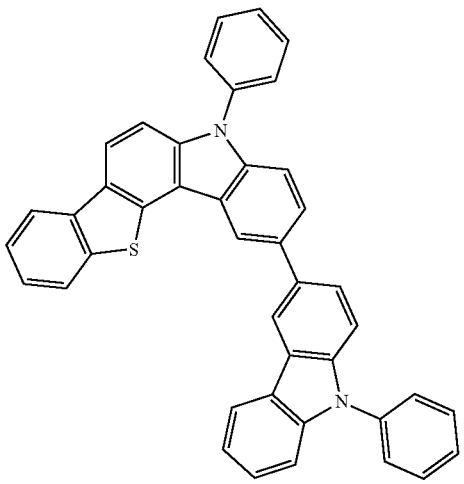
B-63
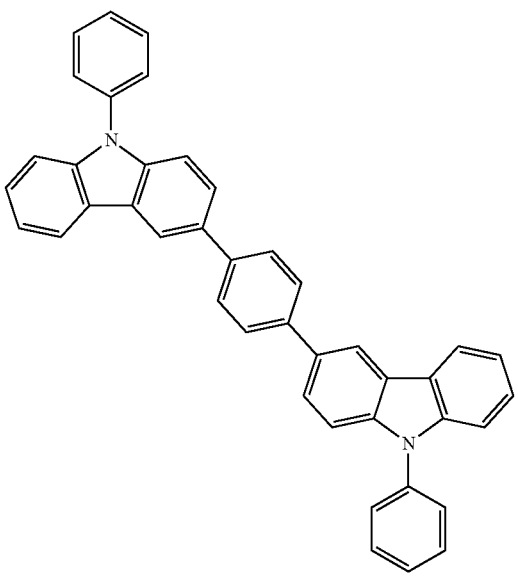

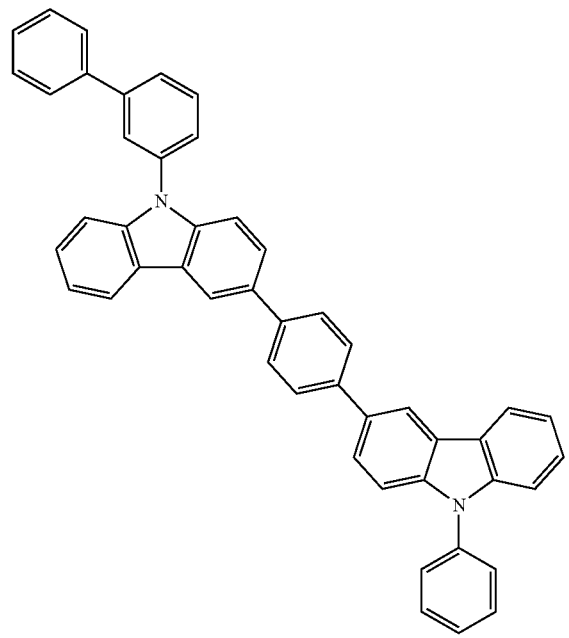
B-64
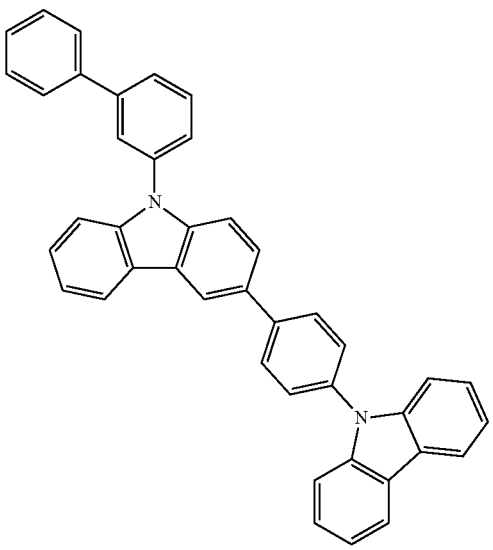
B-66
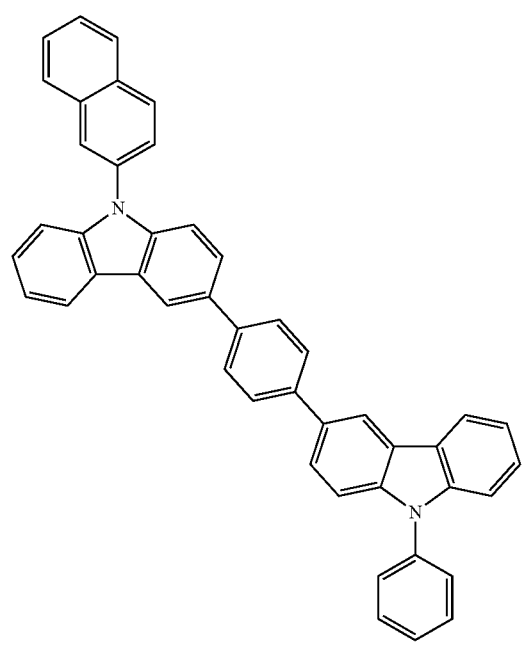
B-65
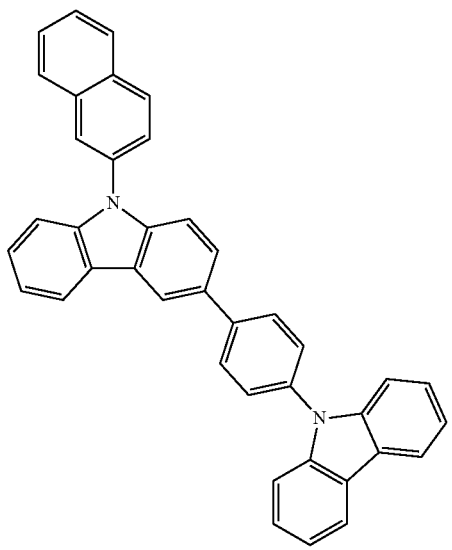
B-67

B-68
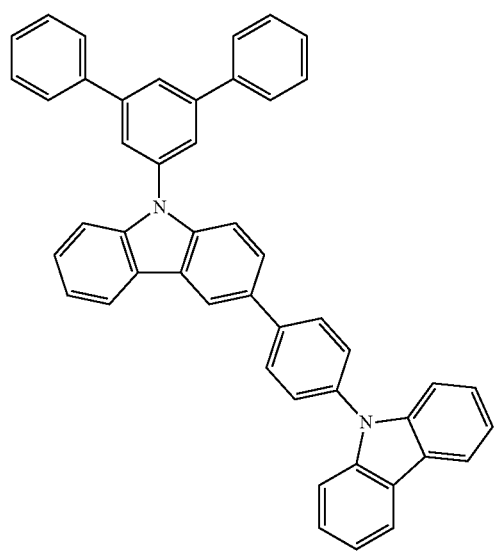
B-69
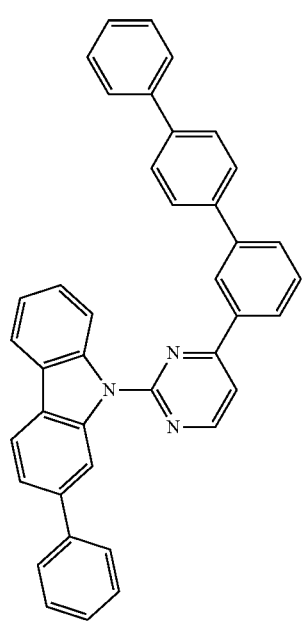
B-70
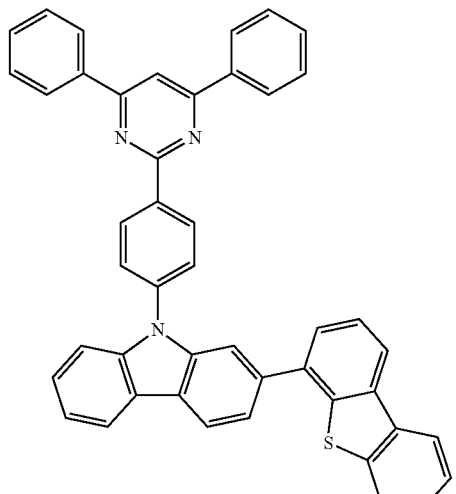
B-71
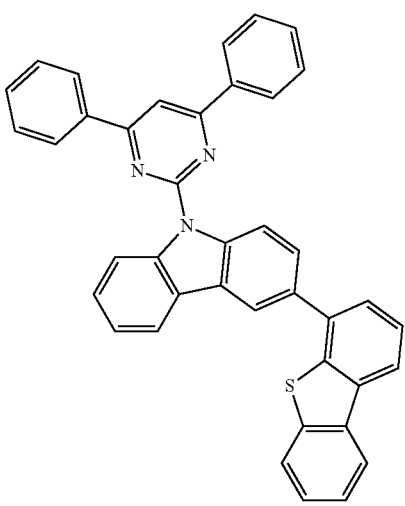
B-72
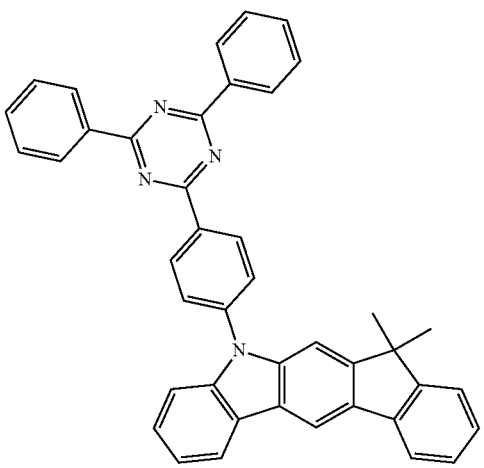

B-73
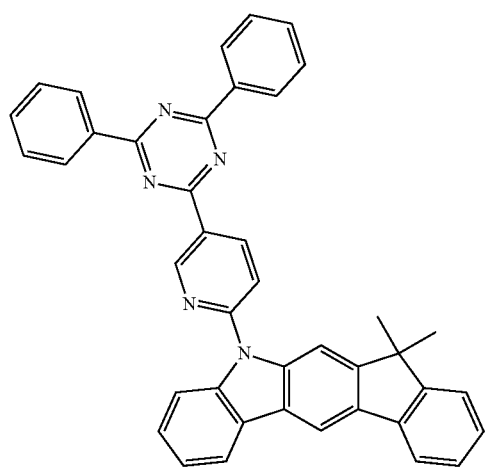
B-74
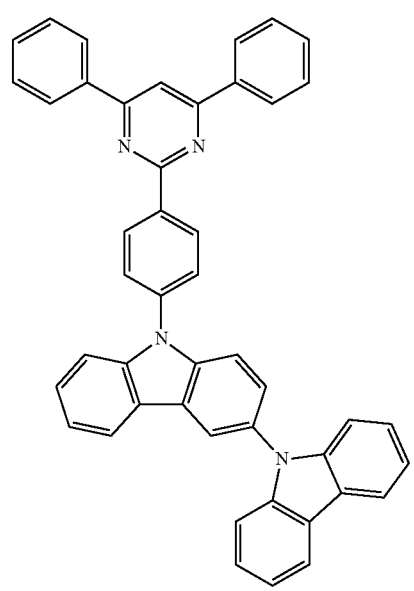
B-75
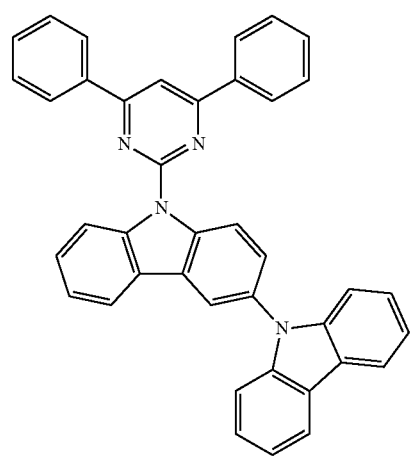
B-76
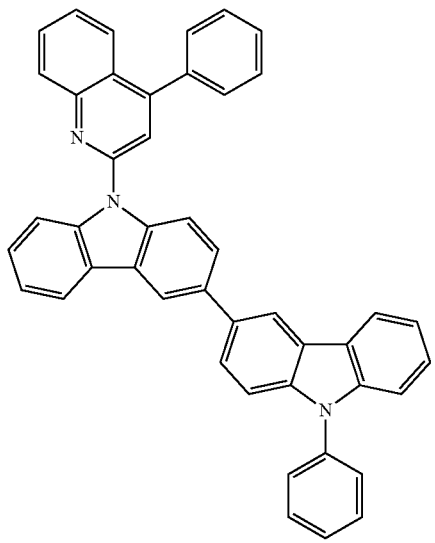
B-77
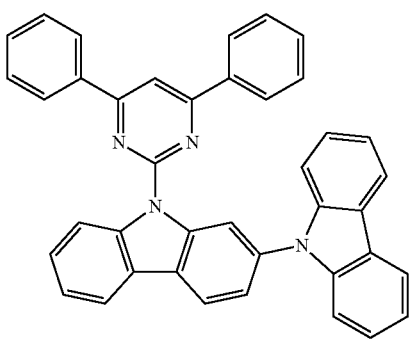
B-78
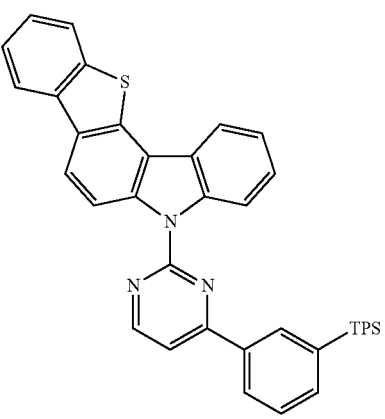

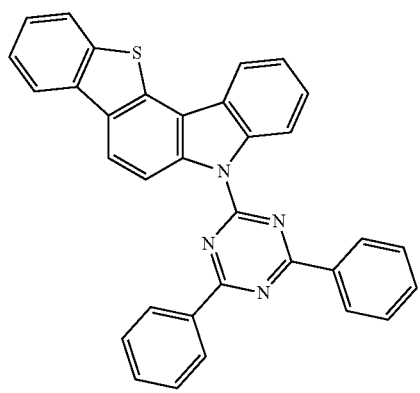
B-79
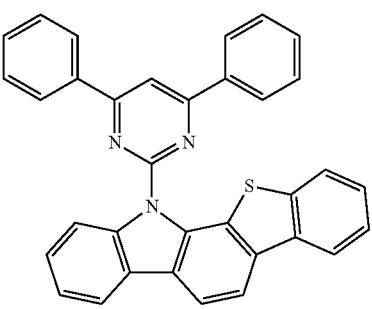
B-83
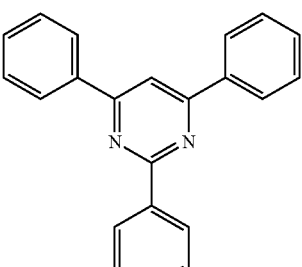
B-80
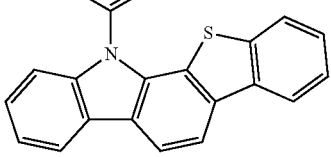
B-81
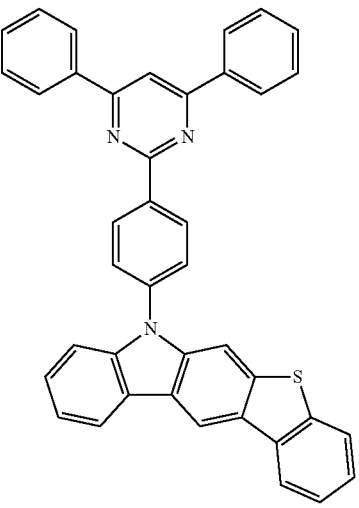
B-84
B-82
B-85

B-86
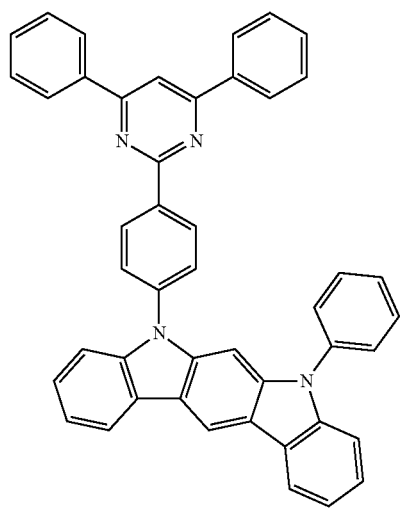
B-87
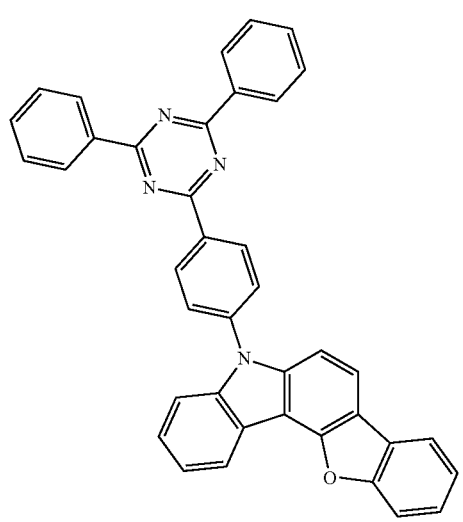
B-88
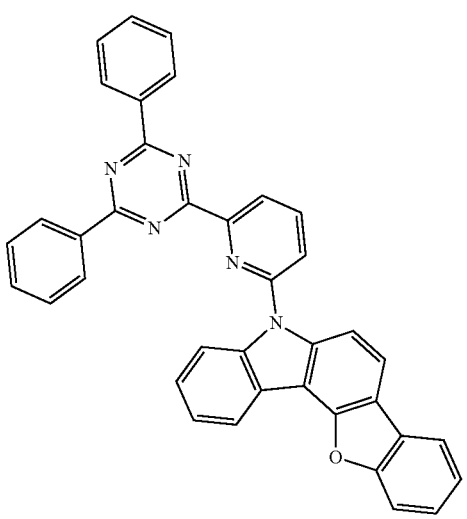
B-89
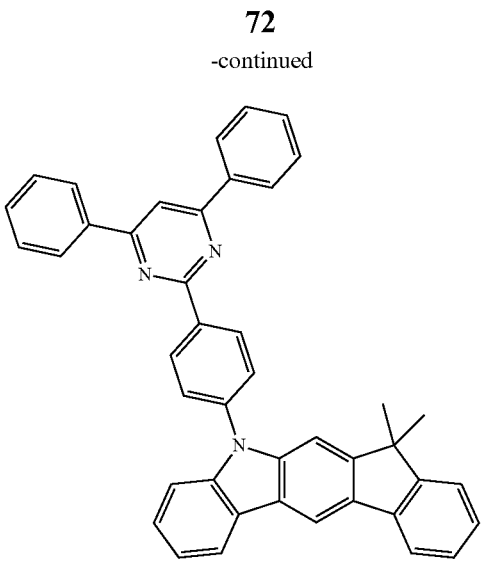
B-90
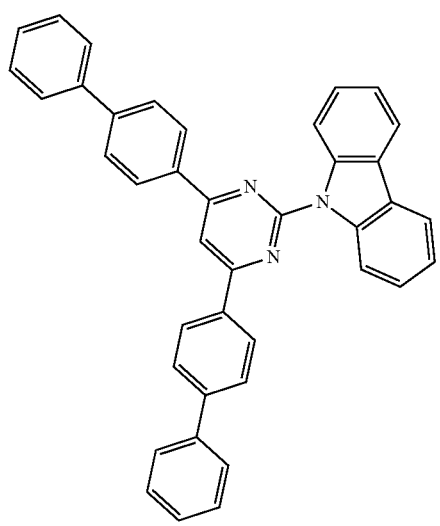
B-91
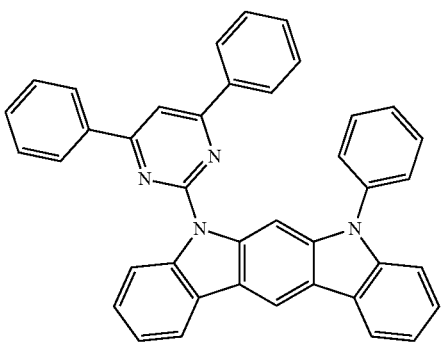

B-92
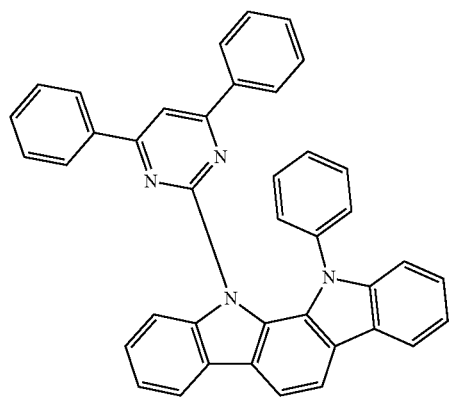
B-93
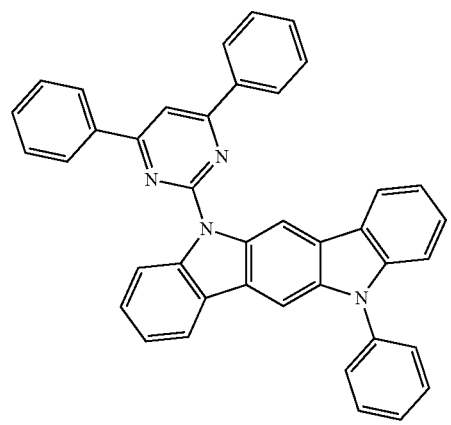
B-94
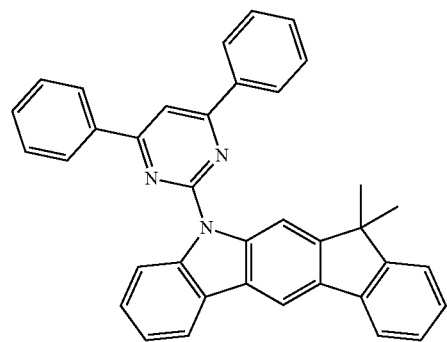
B-95
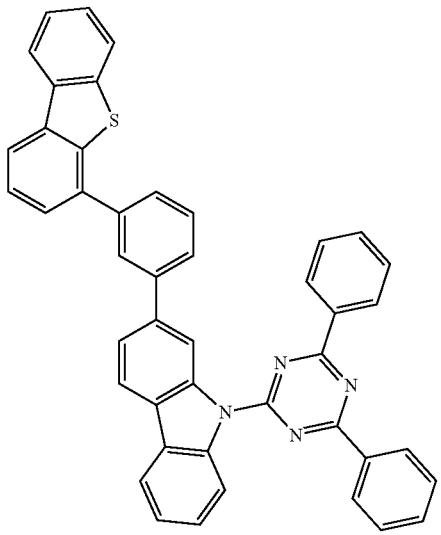
B-96
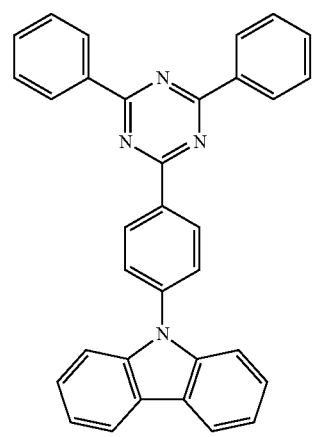
B-97
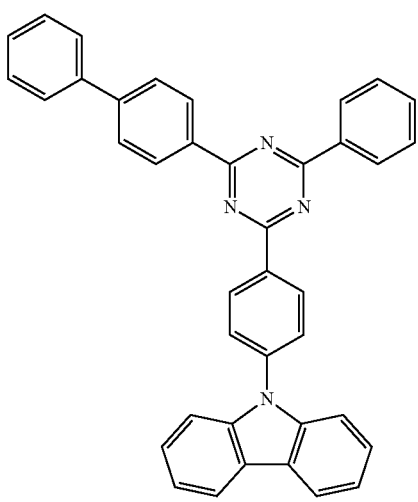

B-98
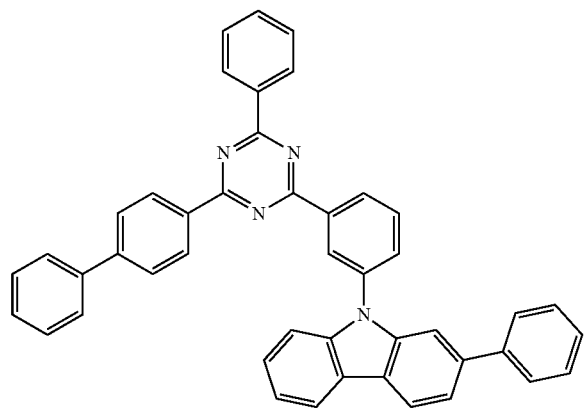
B-99
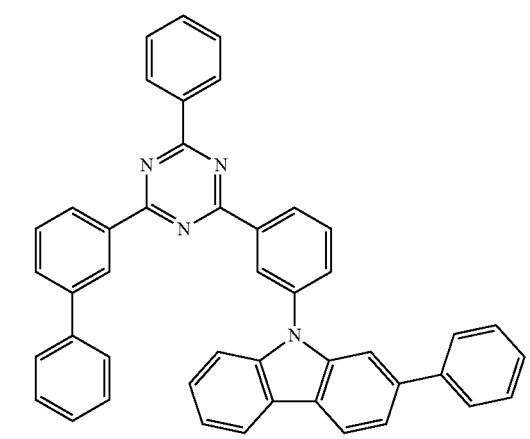
B-100
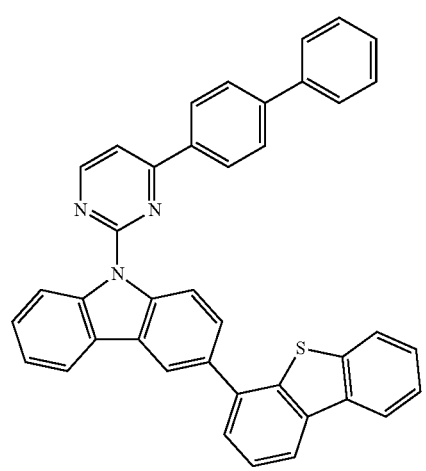
B-101
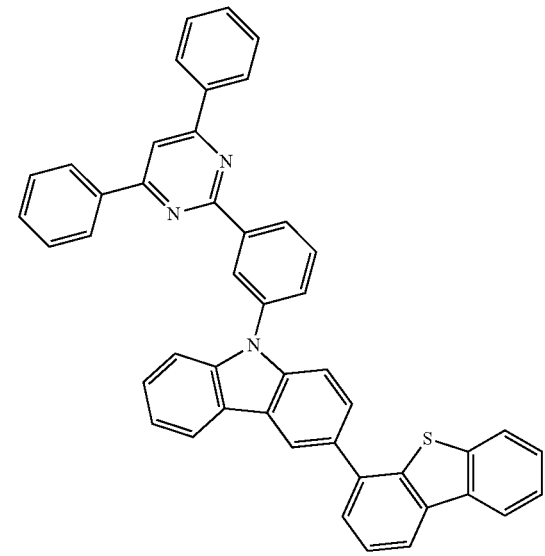
B-102
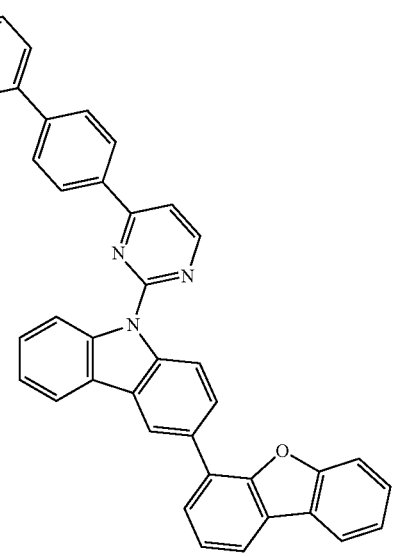

B-103
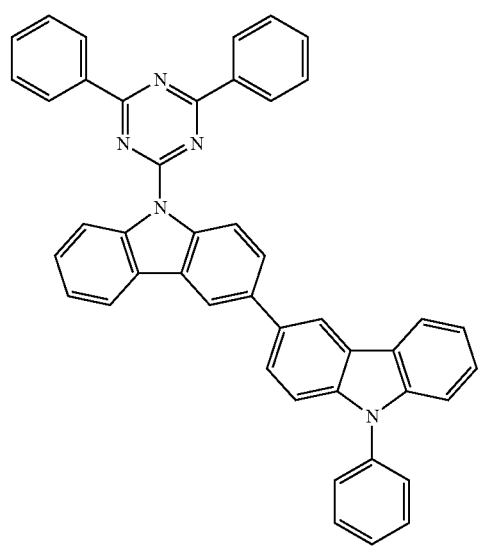
B-104
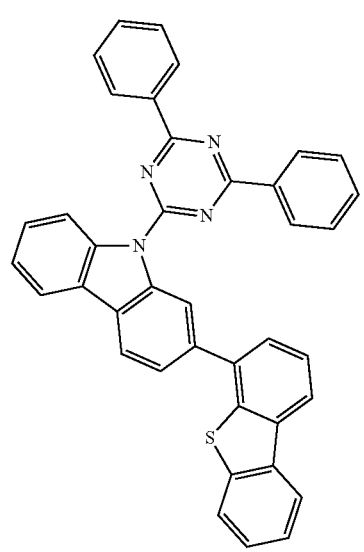
B-105
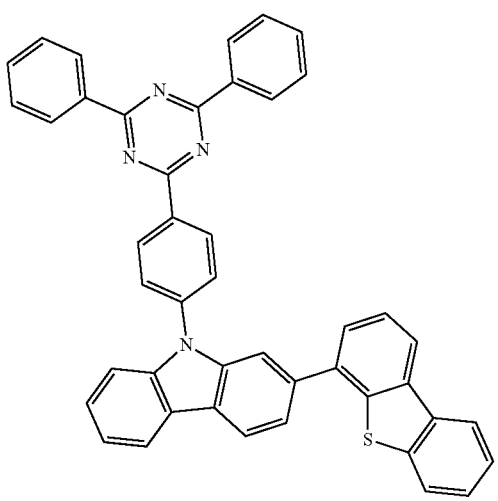
B-106
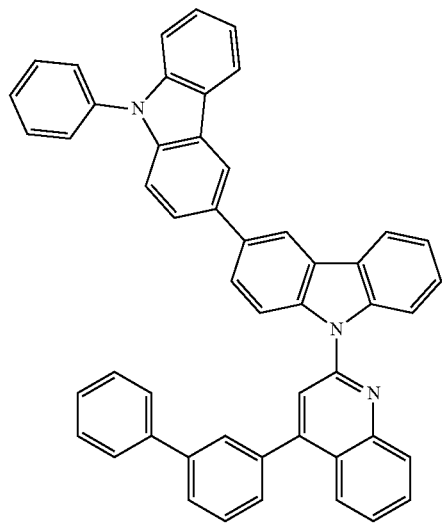
B-107
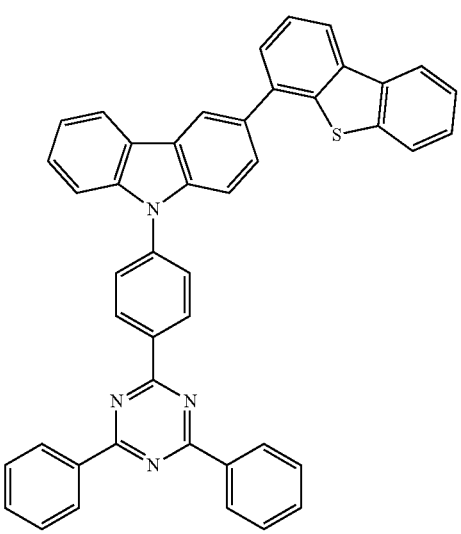
B-108
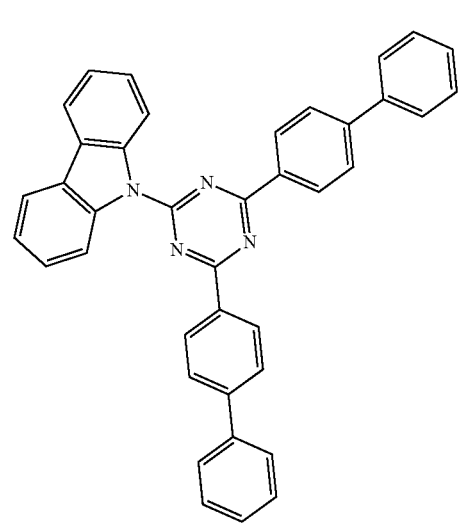

B-109
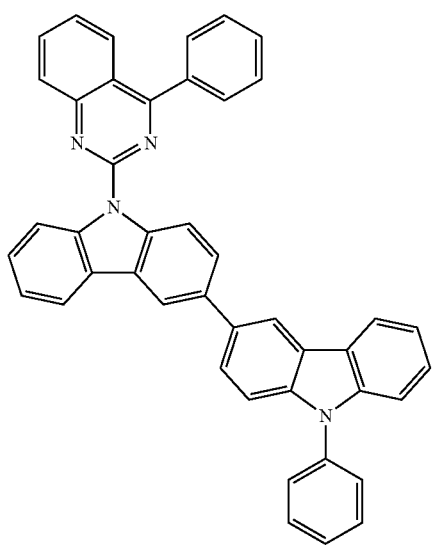
B-110
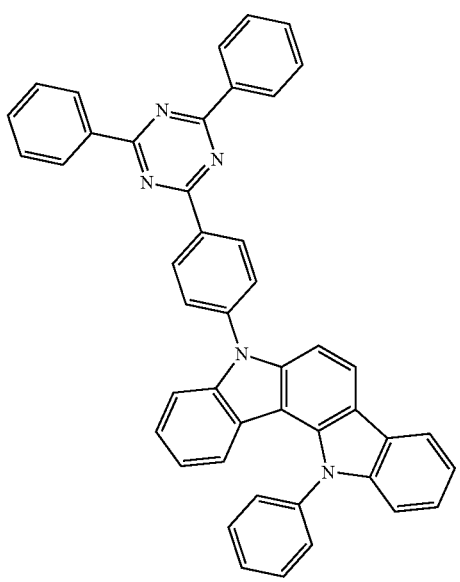
B-111
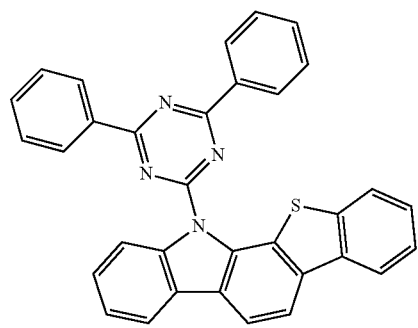
B-112
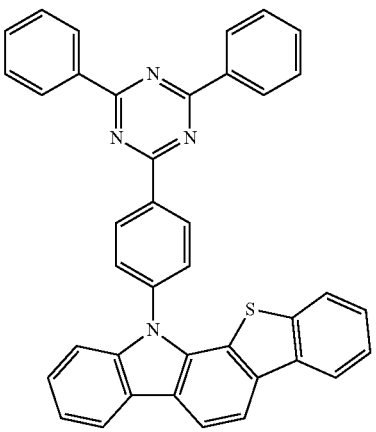
B-113
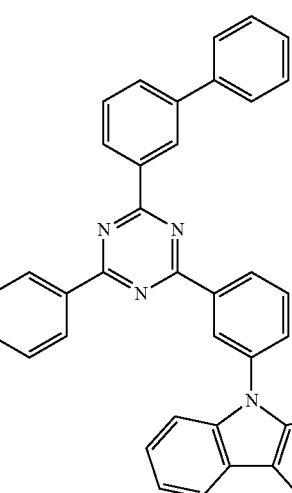
B-114
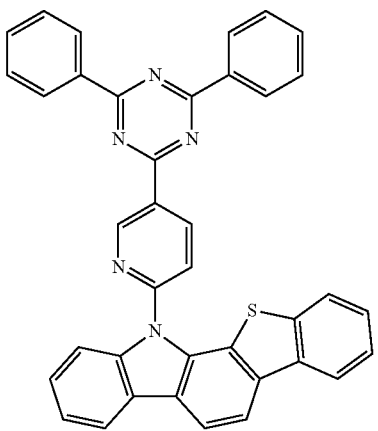

B-115
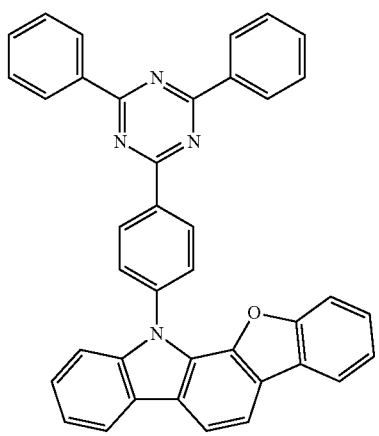
B-116
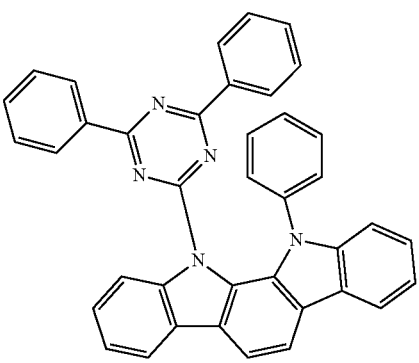
B-117
B-118
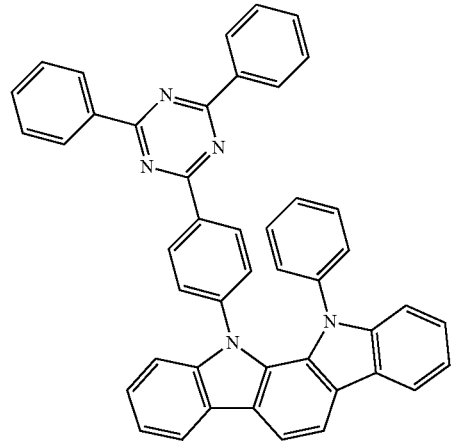
B-119
B-120
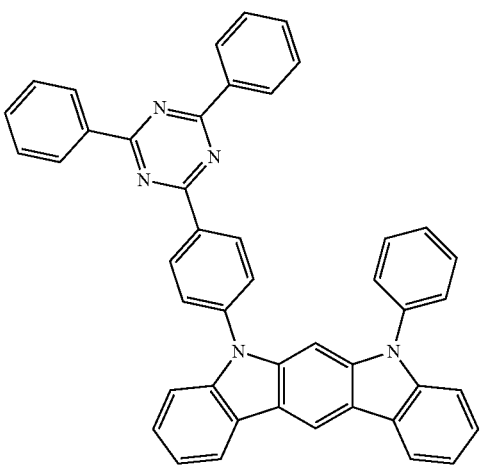

B-121
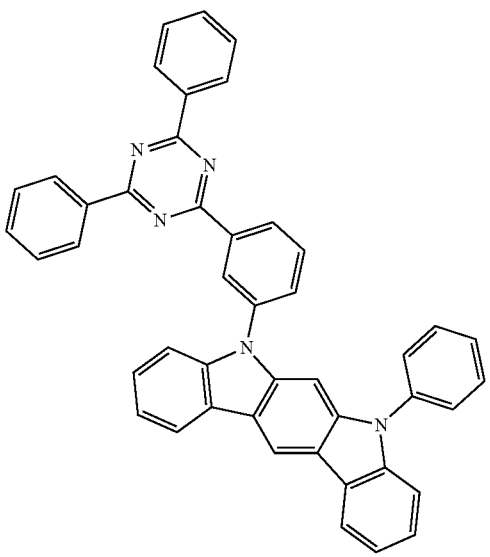
B-124
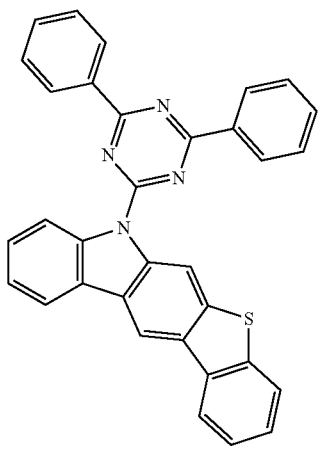
B-122
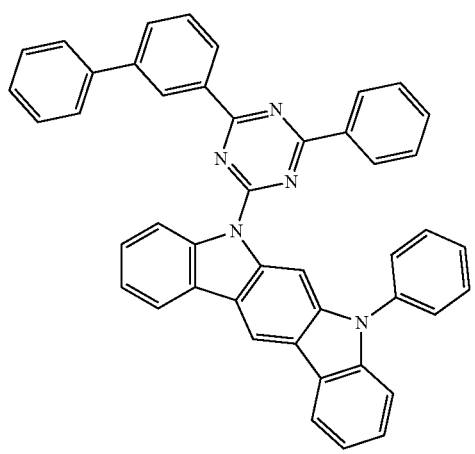
B-125
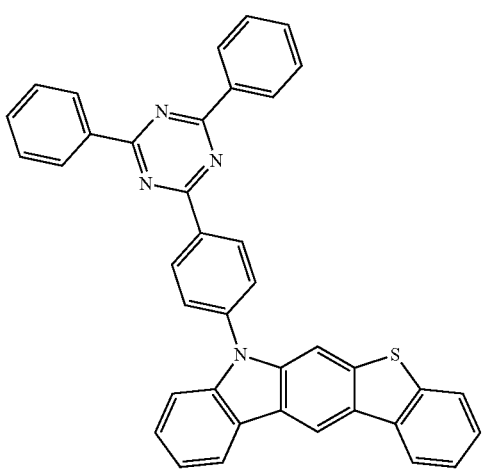
B-123
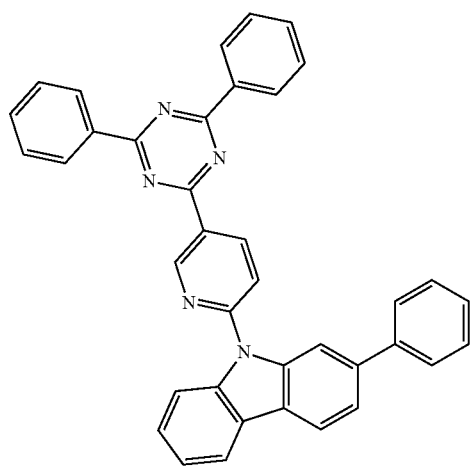
B-126
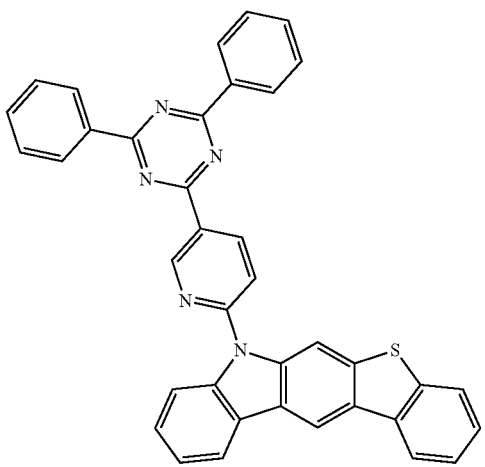

B-127
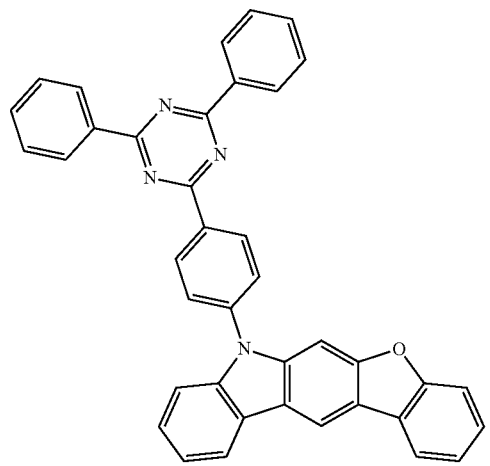
B-128
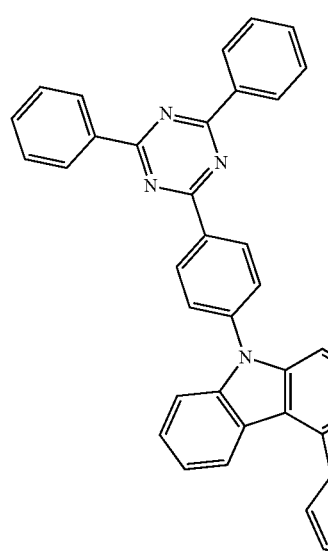
B-129
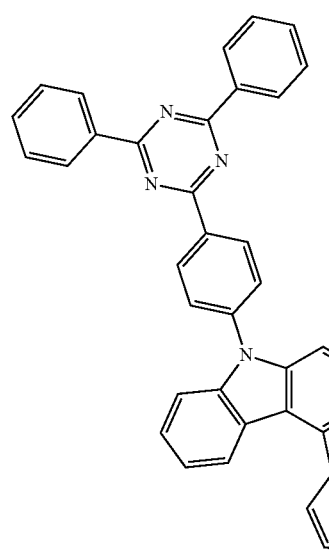
B-130
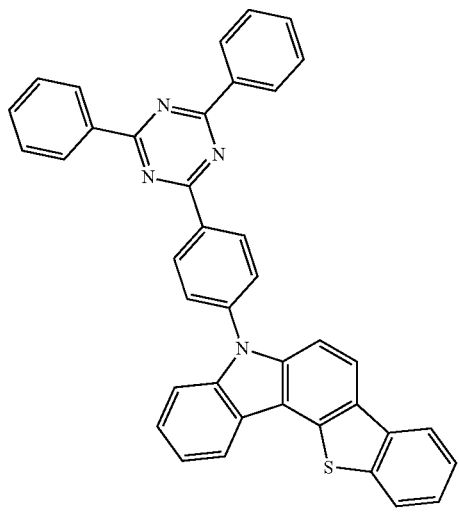
B-131
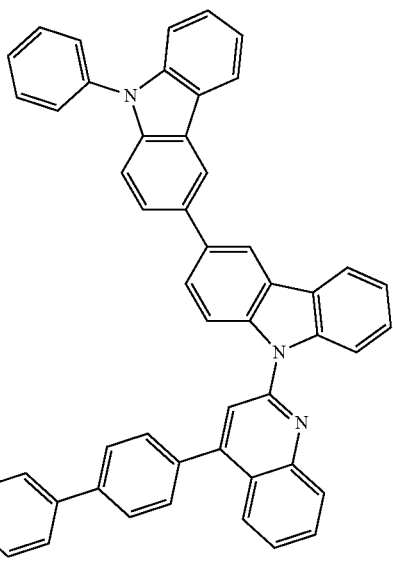
B-132
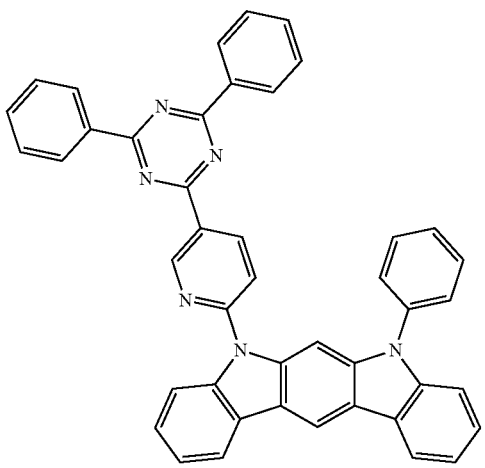

B-133
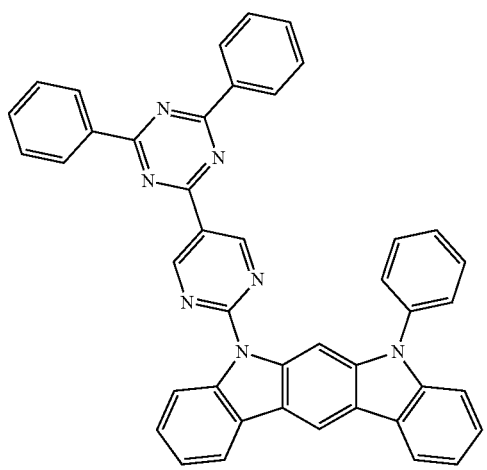
B-134
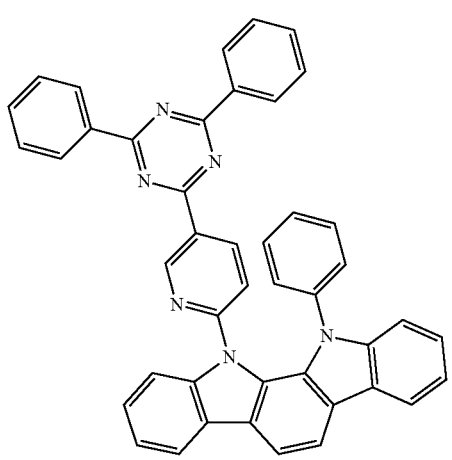
B-135
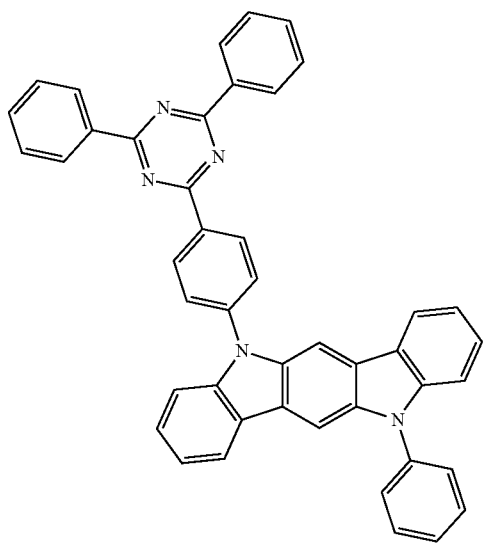
B-136
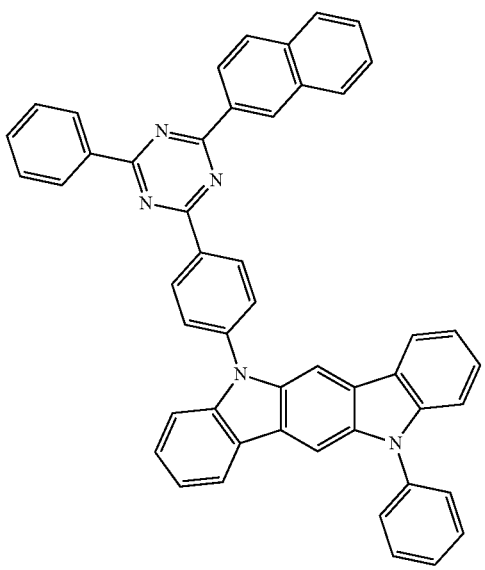
B-137
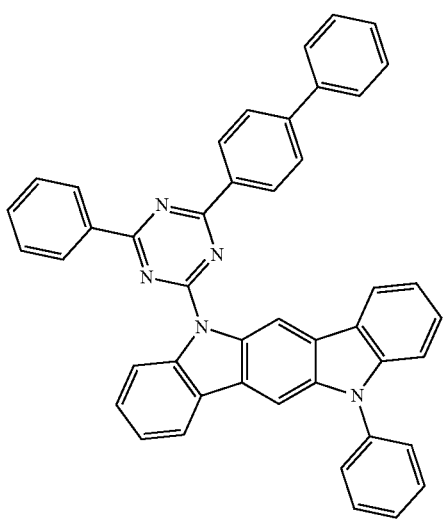
B-138
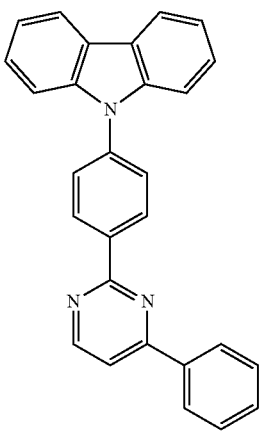

B-139
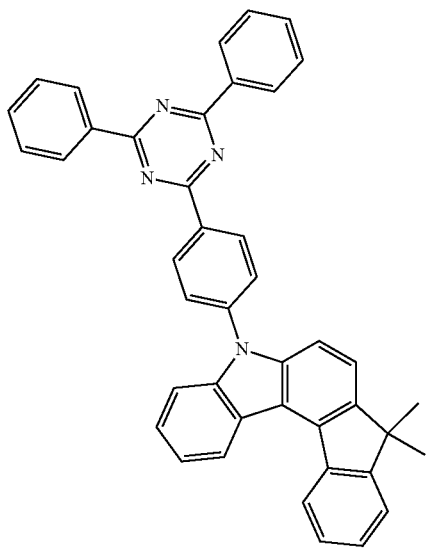
B-140
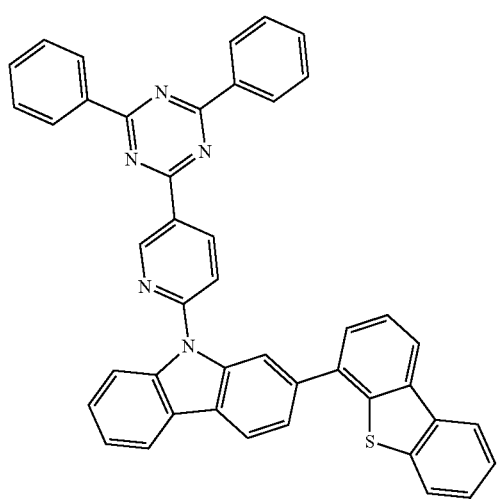
B-141
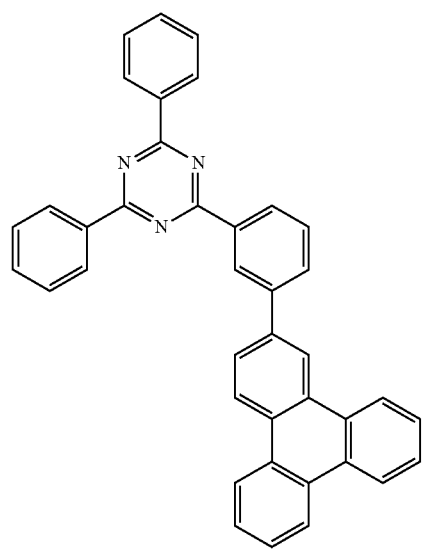
B-142
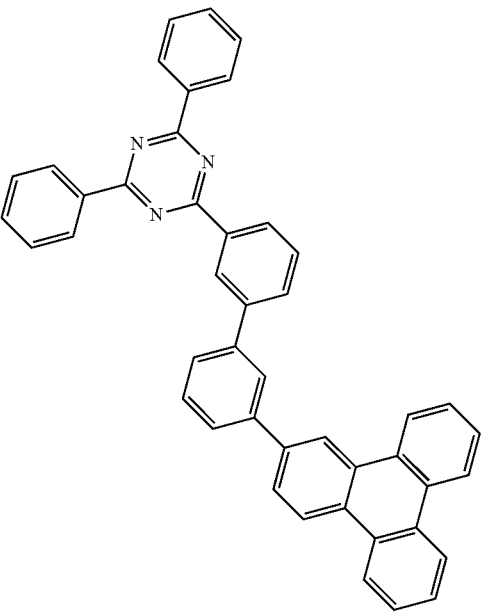
B-143
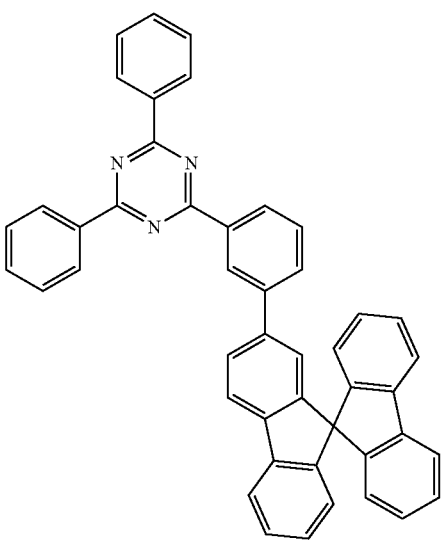

-continued
B-144
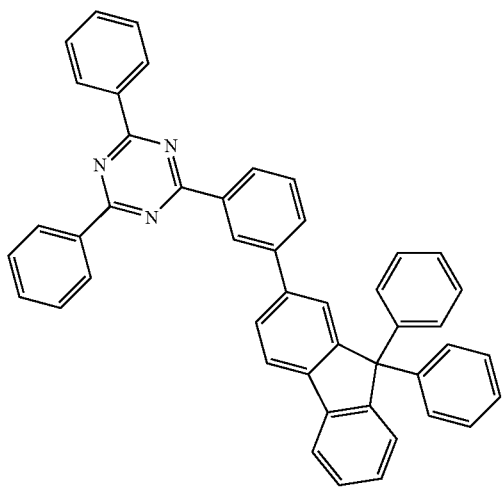
B-145
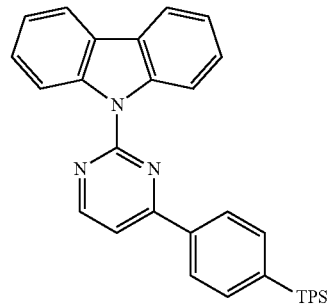
B-146
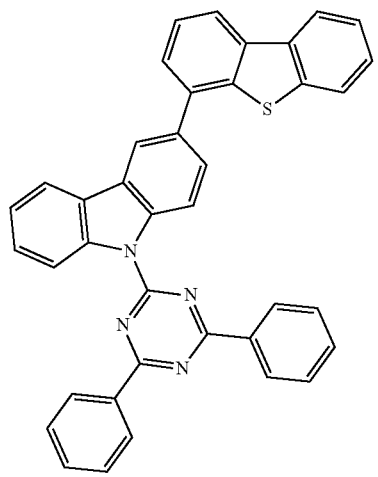
-continued
B-147
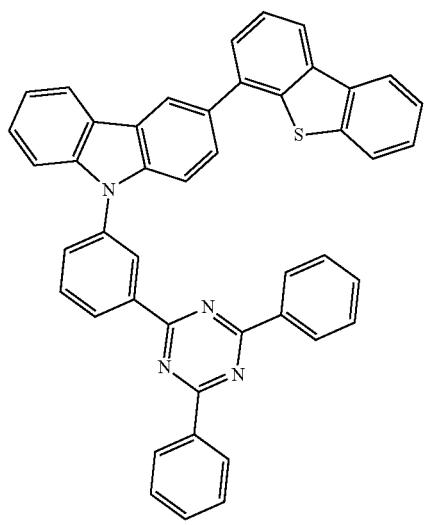
B-148
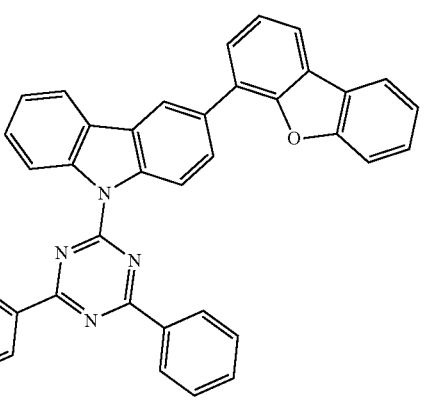
B-149
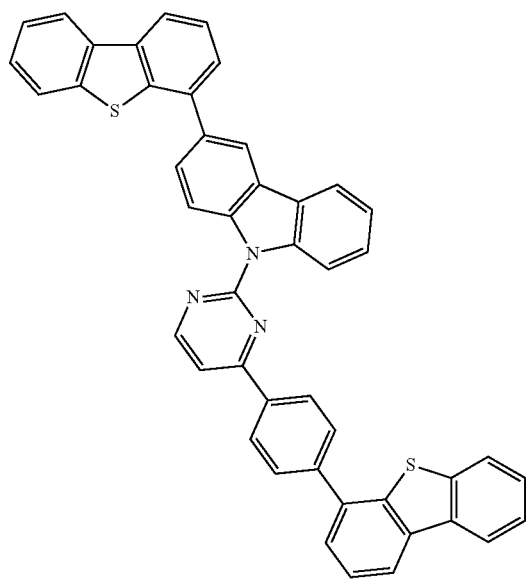

B-150
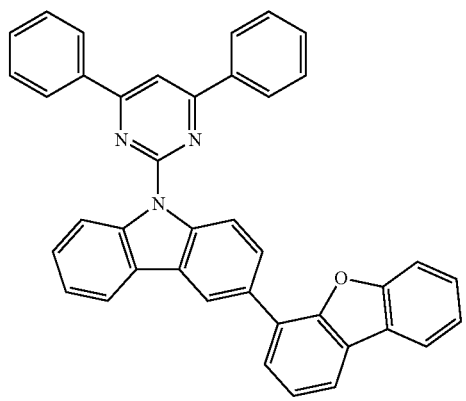
B-151
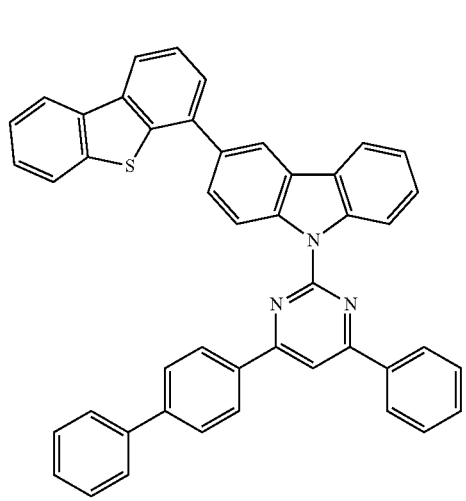
B-152
B-153
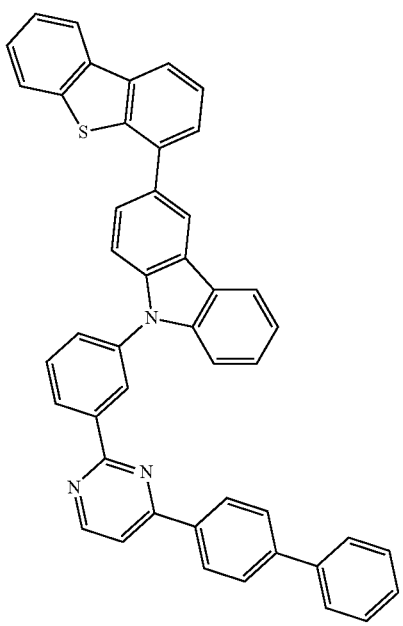
B-154
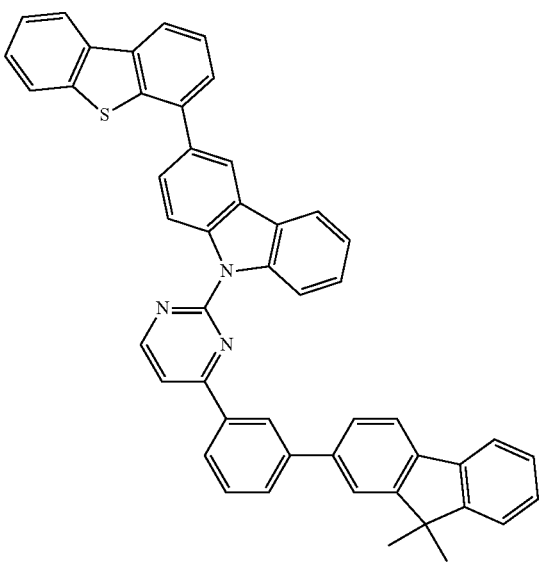

B-155
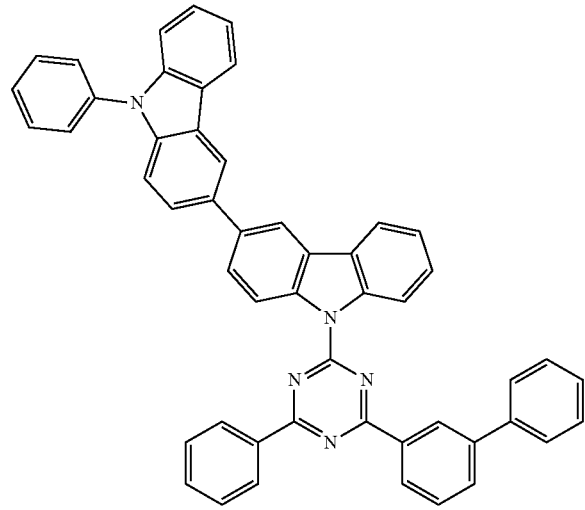
B-157
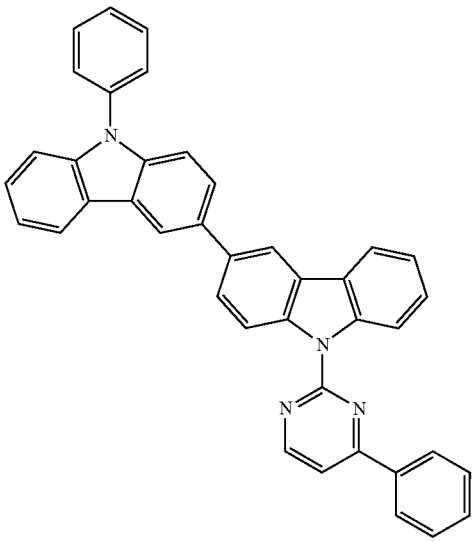
B-158
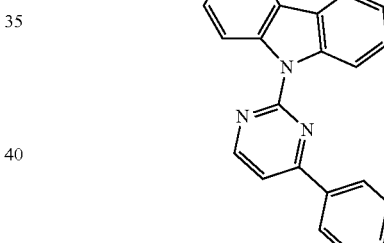
B-156
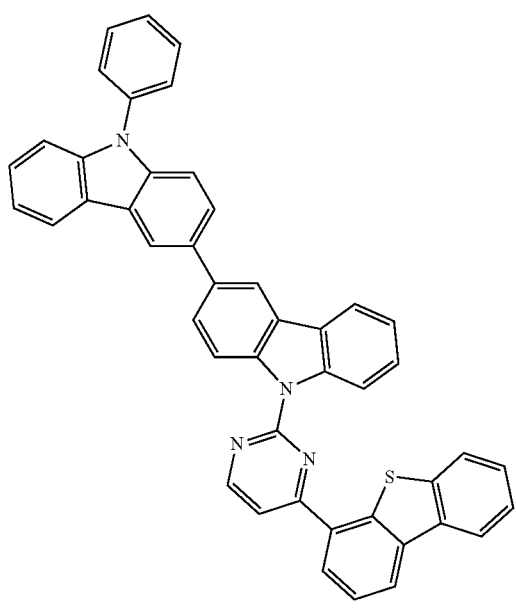
B-159
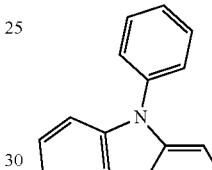

B-160
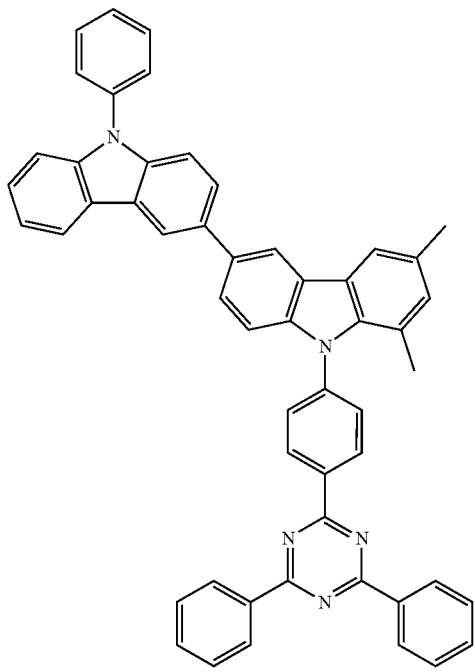
B-161
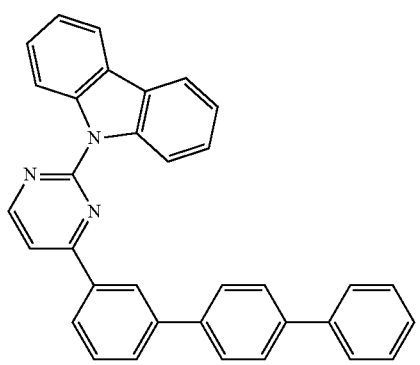
B-162
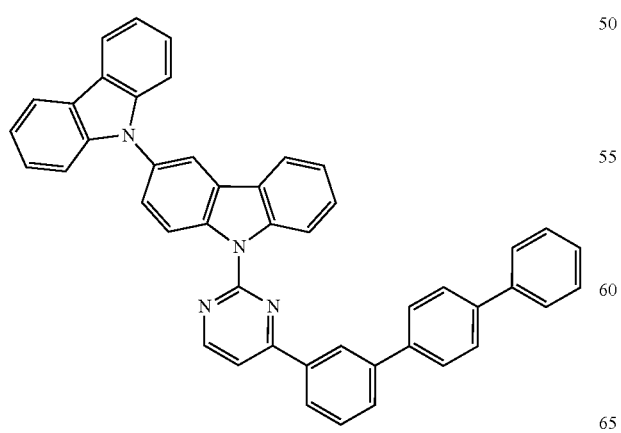
B-163
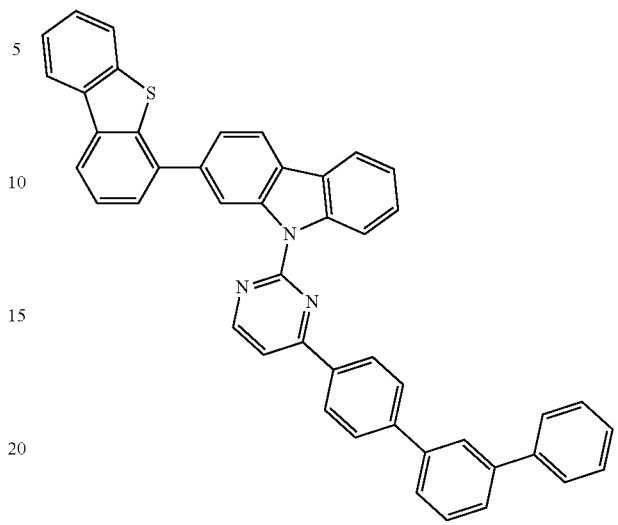
B-164
B-165

B-166
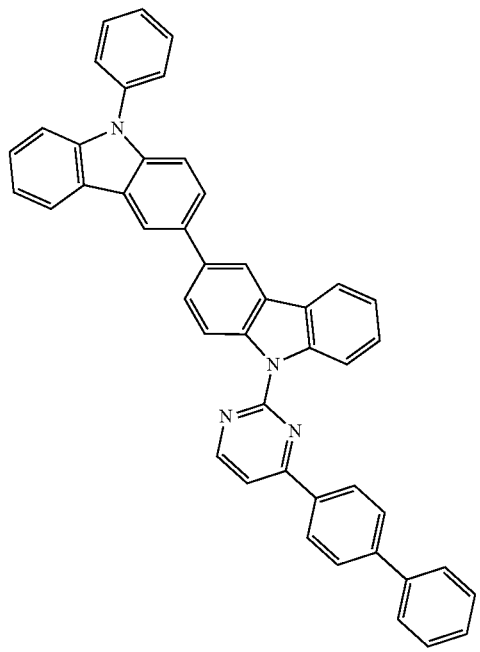
B-167
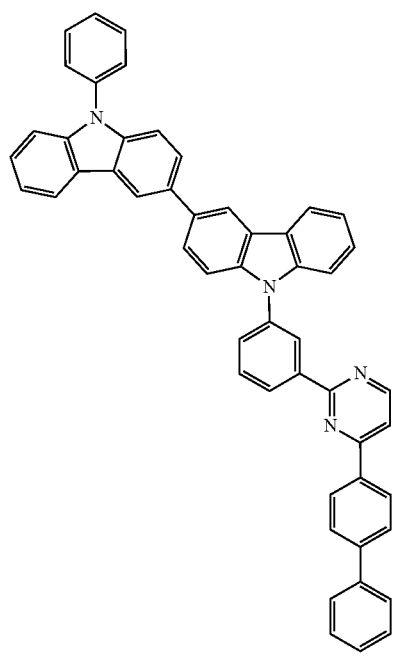
B-168
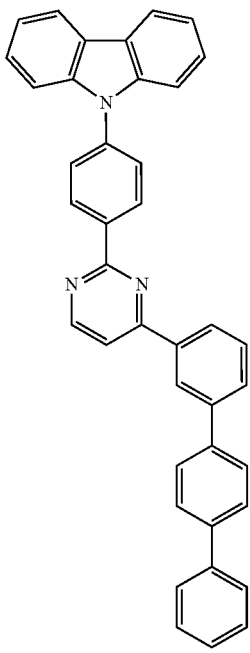
B-169
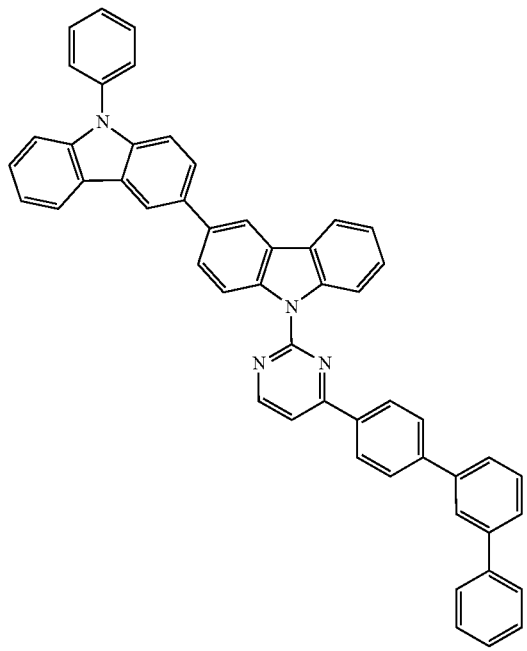

B-170
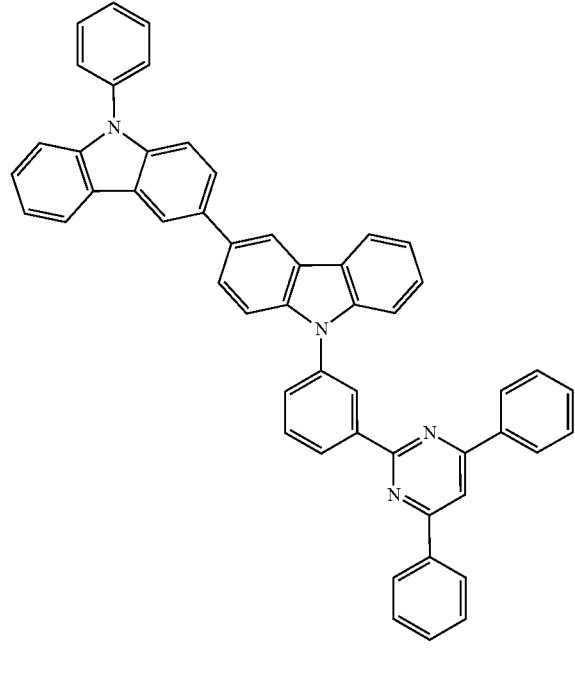
B-172
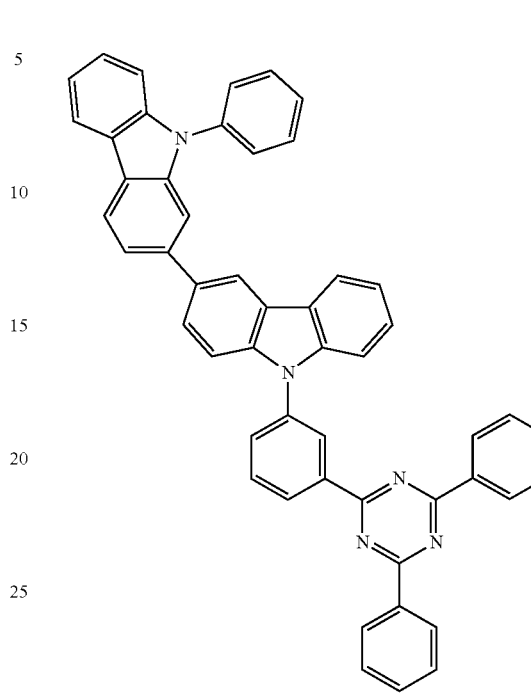
B-171
B-173
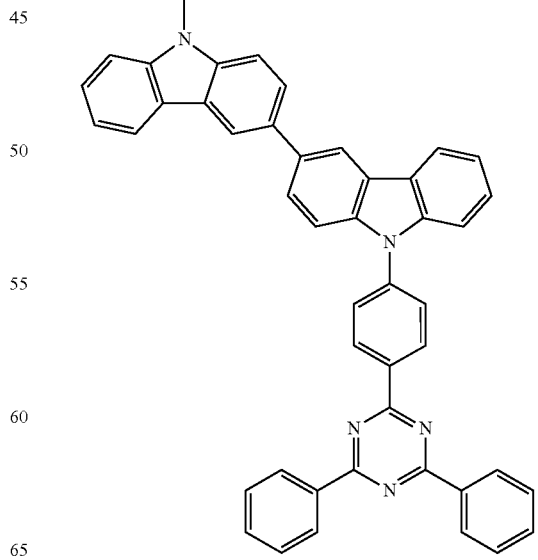

B-174
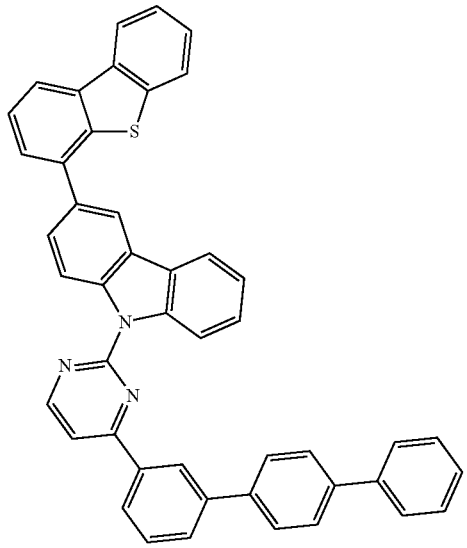
B-175
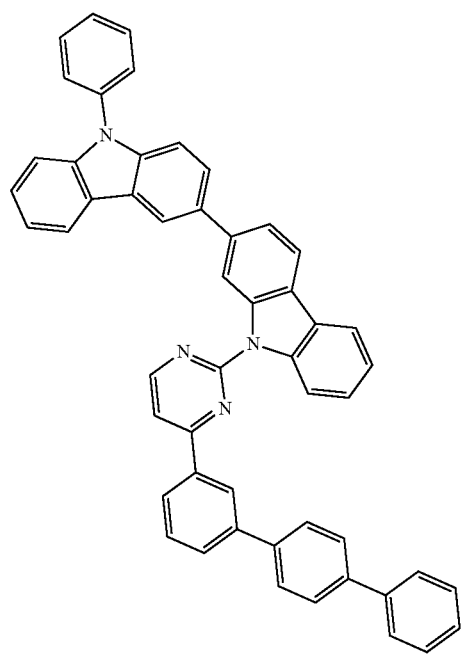
B-176
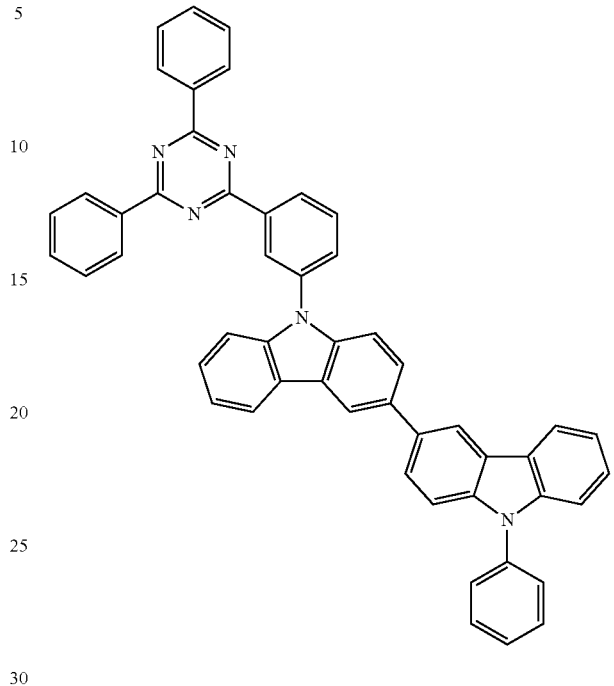
B-177
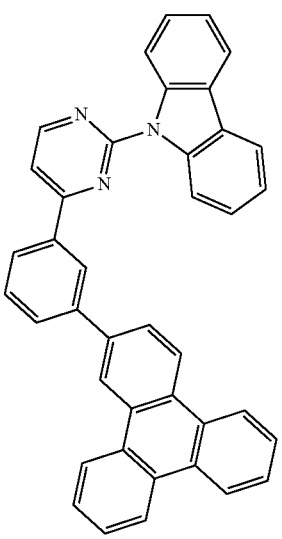

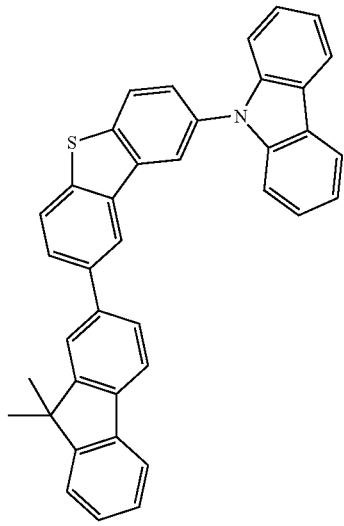
B-178
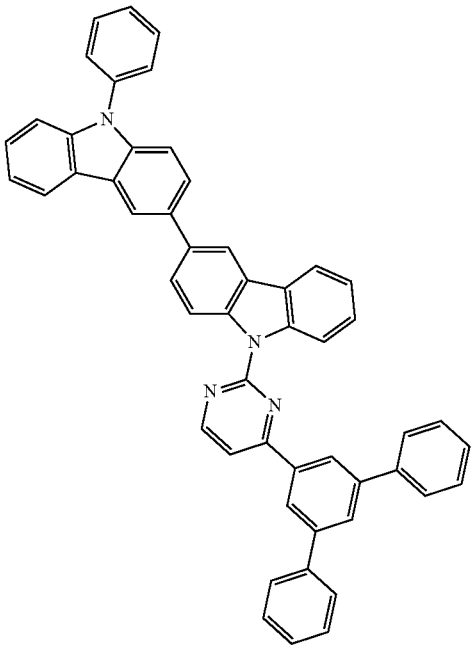
B-180
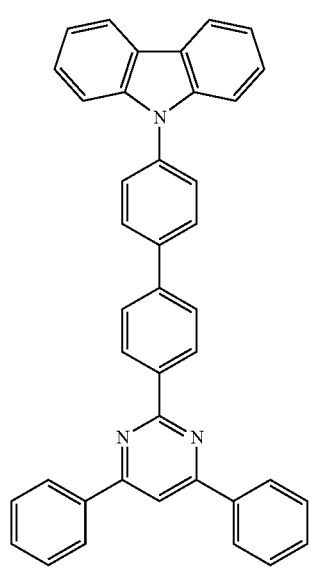
B-179
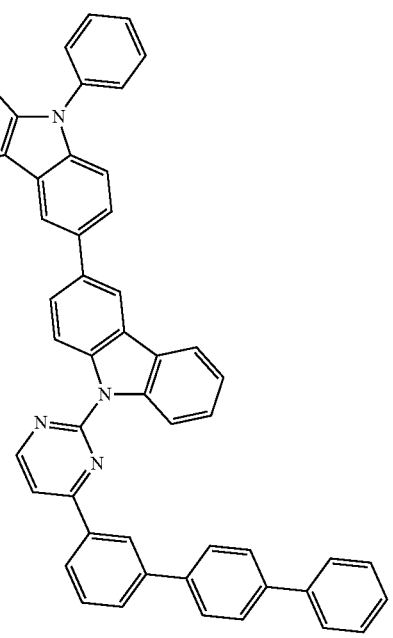
B-181

B-182
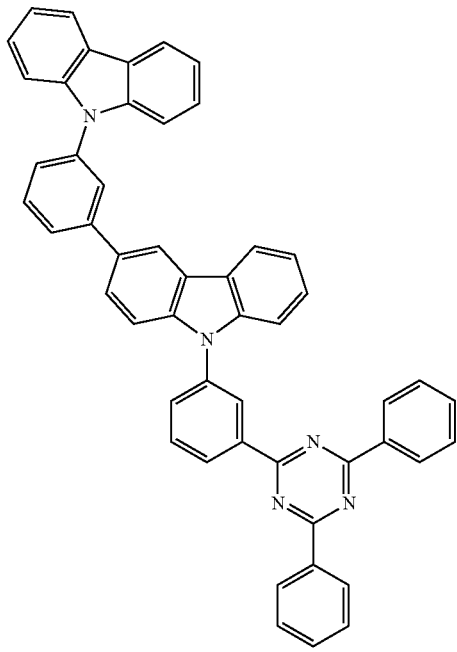
B-183
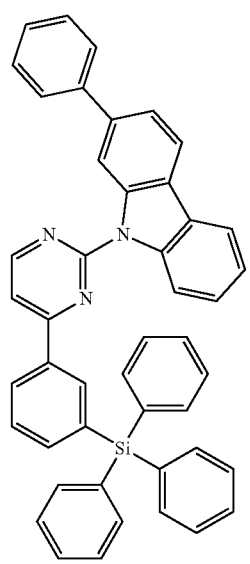
B-184
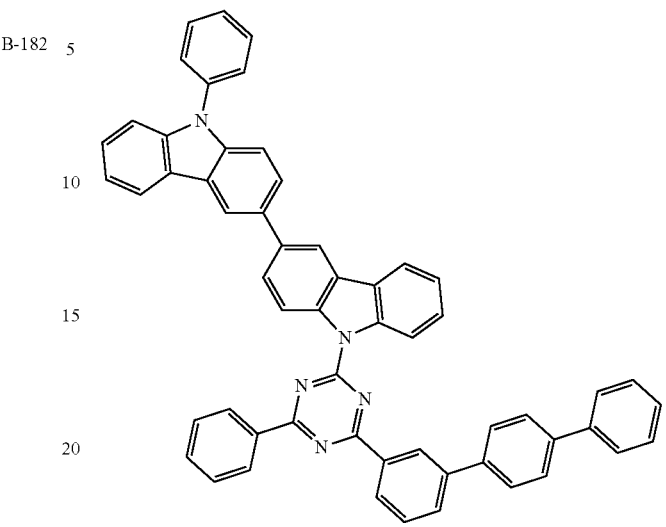
B-185
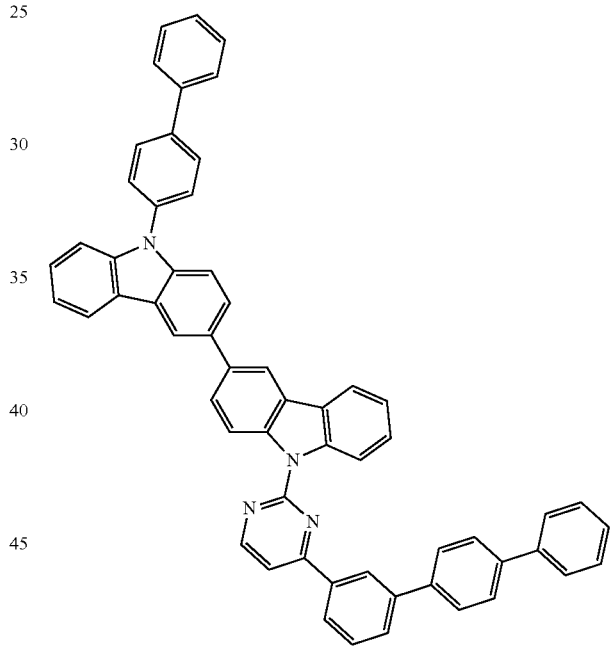
B-186
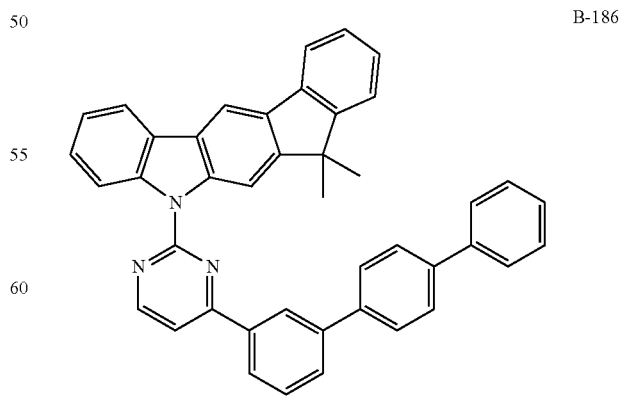

B-187
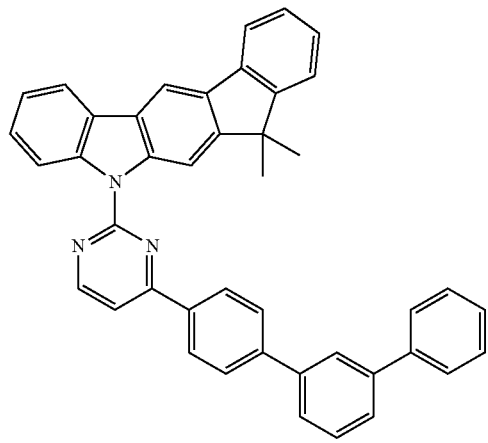
B-188
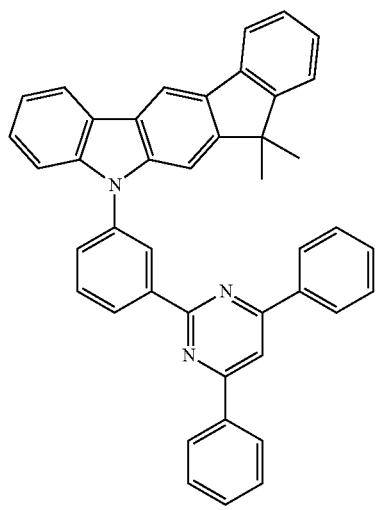
B-189
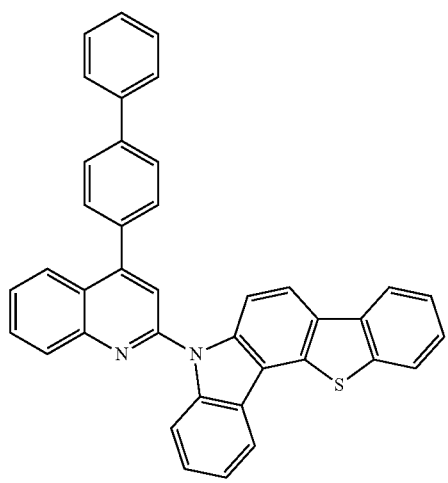
B-190
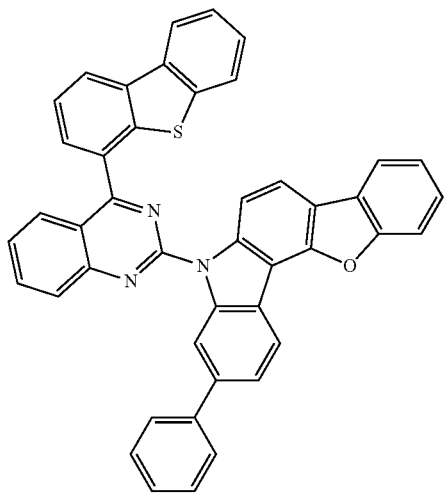
B-191
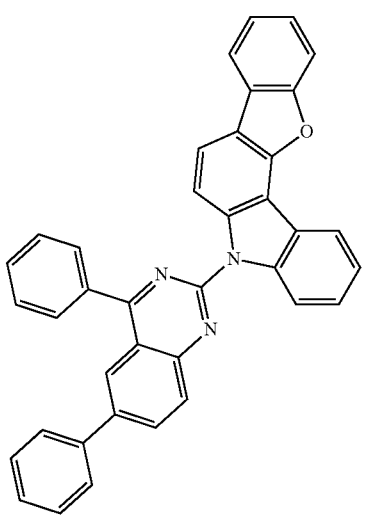
B-192
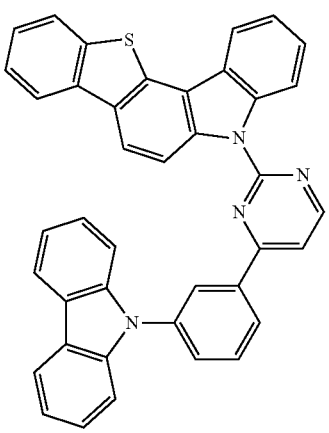

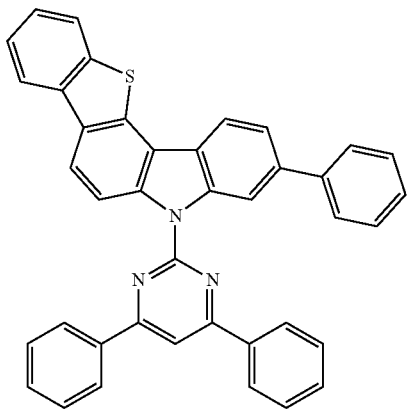

B-193

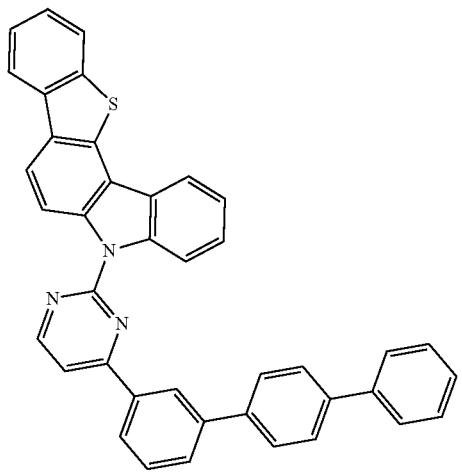

B-196

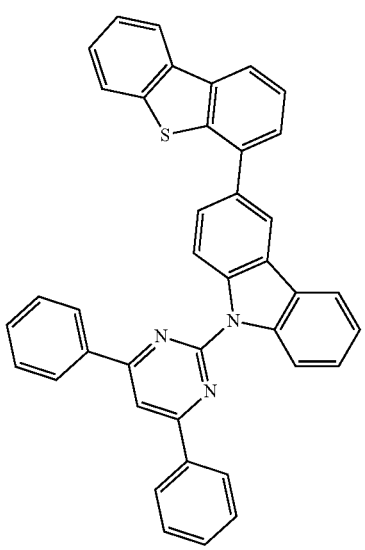

B-194

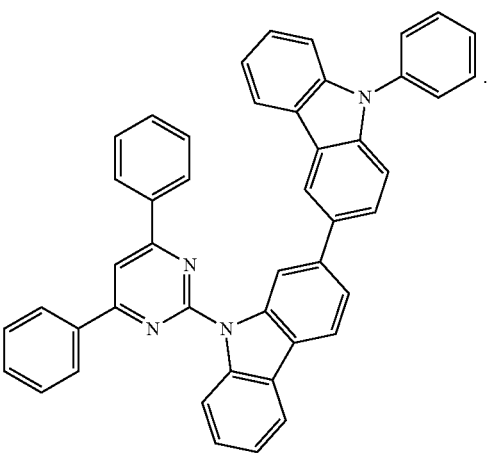

B-197

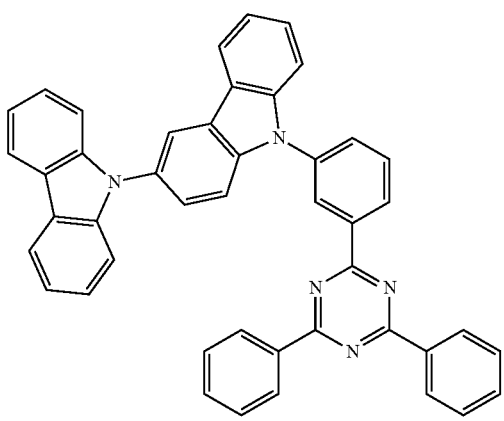

B-195

[wherein TPS represents triphenylsilyl.]

The dopant to be comprised in the organic electroluminescent device of the present disclosure is preferably at least one phosphorescent dopant. The phosphorescent dopant material for the organic electroluminescent device of the present disclosure is not limited, but may be preferably selected from metallated complex compounds of iridium (Ir), osmium (Os), copper (Cu) or platinum (Pt), more preferably selected from ortho-metallated complex compounds of iridium (Ir), osmium (Os), copper (Cu) or platinum (Pt), and even more preferably ortho-metallated iridium complex compounds.

The compounds represented by the following formulae 101 to 103 may be used as the dopant to be comprised in the organic electroluminescent device of the present disclosure:

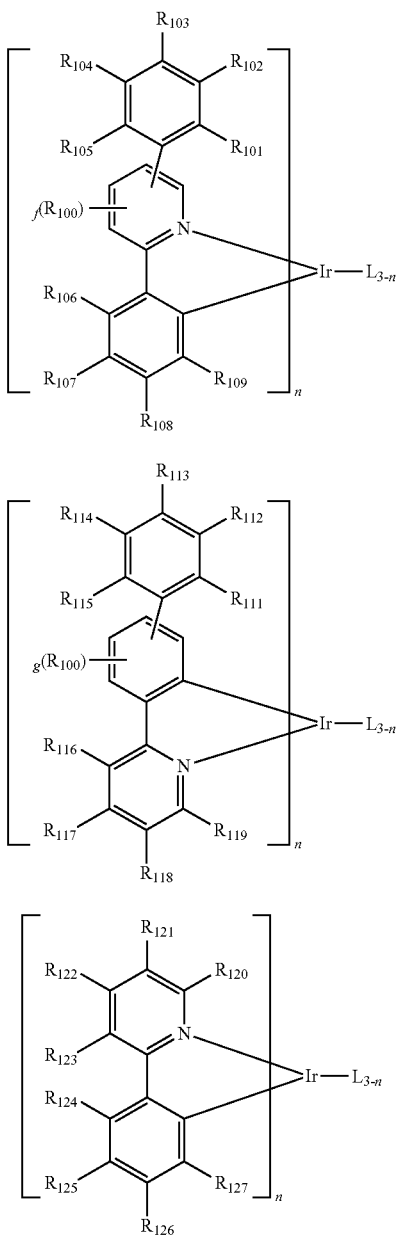

(101)

(102)

(103)

wherein L is selected from the following structures:

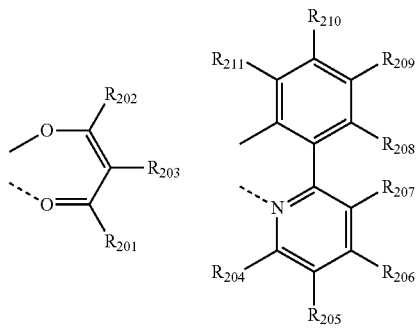

$R_{100}$ represents hydrogen, a substituted or unsubstituted (C1-C30)alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a (C1-C30)alkyl substituted or unsubstituted with a halogen, a substituted or unsubstituted (C3-C30)cycloalkyl, a substituted or unsubstituted (C6-C30)aryl, a cyano, or a substituted or unsubstituted (C1-C30)alkoxy; $R_{106}$ to $R_{109}$, each independently, may be linked to an adjacent substituent(s) to form a substituted or unsubstituted fused ring, for example, a fluorene substituted or unsubstituted with an alkyl, a dibenzothiophene substituted or unsubstituted with an alkyl, or a dibenzofuran substituted or unsubstituted with an alkyl; 8120 to $R_{123}$, each independently, may be linked to an adjacent substituent(s) to form a substituted or unsubstituted fused ring, for example, a quinoline substituted or unsubstituted with an alkyl or aryl;

$R_{124}$ to $R_{127}$, each independently, represent hydrogen, deuterium, a halogen, a substituted or unsubstituted (C1-C30)alkyl, or a substituted or unsubstituted (C6-C30)aryl; $R_{124}$ to $R_{127}$, each independently, may be linked to an adjacent substituent(s) to form a substituted or unsubstituted fused ring, for example, a fluorene substituted or unsubstituted with an alkyl, a dibenzothiophene substituted or unsubstituted with an alkyl, or a dibenzofuran substituted or unsubstituted with an alkyl;

$R_{201}$ to $R_{211}$, each independently, represent hydrogen, deuterium, a halogen, a (C1-C30)alkyl substituted or unsubstituted with a halogen, a substituted or unsubstituted (C3-C30)cycloalkyl, or a substituted or unsubstituted (C6-C30)aryl; $R_{208}$ to $R_{211}$, each independently, may be linked to an adjacent substituent(s) to form a substituted or unsubstituted fused ring, for example, a fluorene substituted or unsubstituted with an alkyl, a dibenzothiophene substituted or unsubstituted with an alkyl, or a dibenzofuran substituted or unsubstituted with an alkyl;

f and g, each independently, represent an integer of 1 to 3; when f or g is an integer of 2 or more, each of $R_{100}$ may be the same or different; and n represents an integer of 1 to 3.

Specifically, the phosphorescent dopant includes the following:

D-1

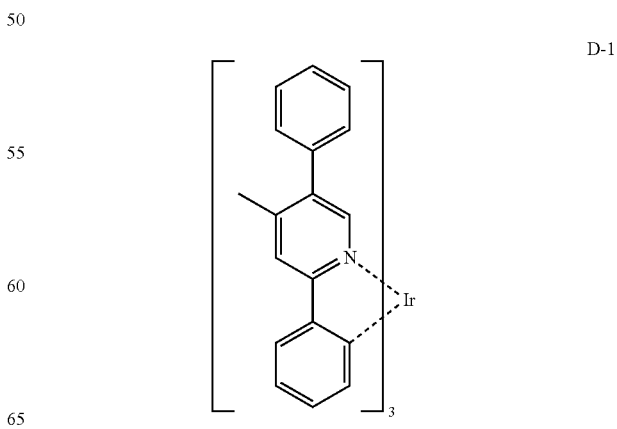

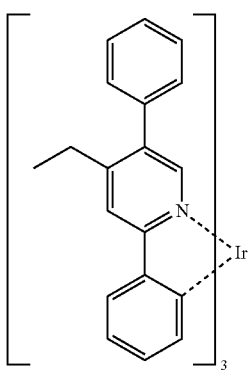 D-2
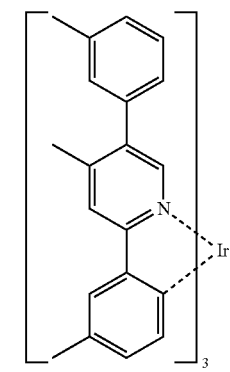 D-3
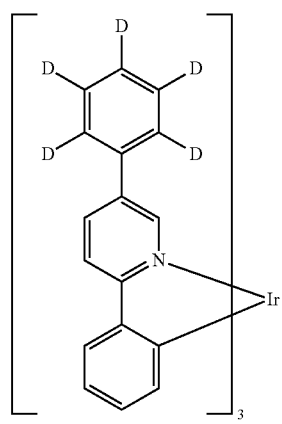 D-4
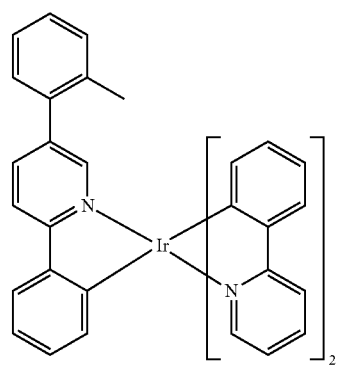 D-5
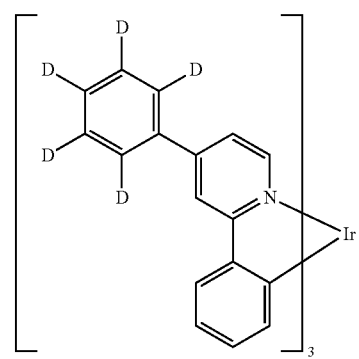 D-6
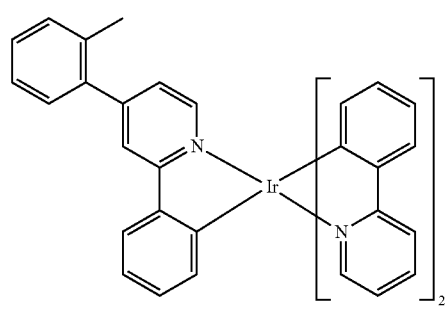 D-7
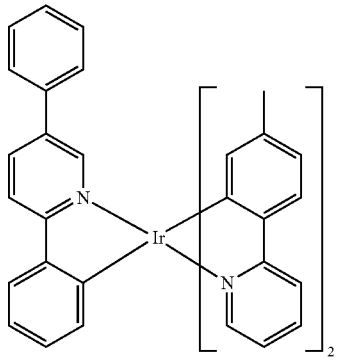 D-8
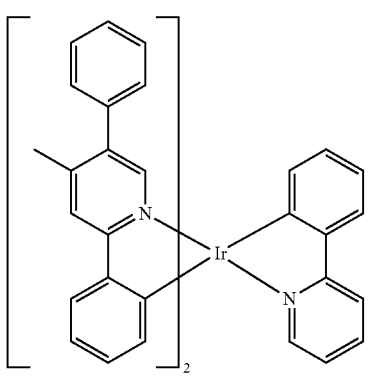 D-9

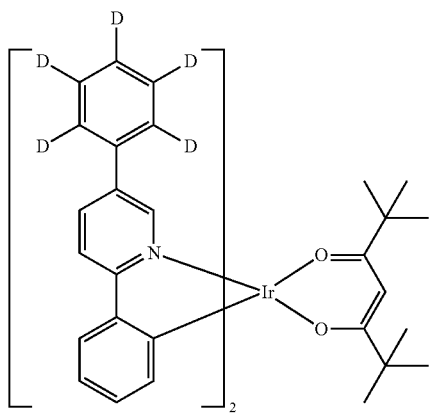
D-10
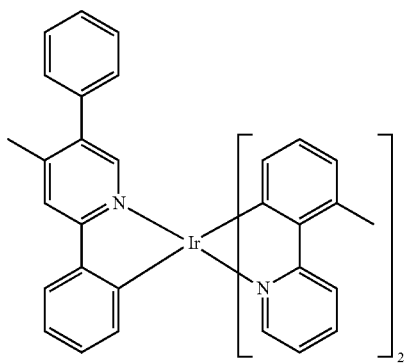
D-14
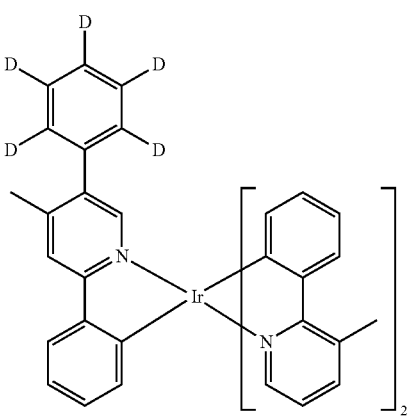
D-15
D-11
D-12
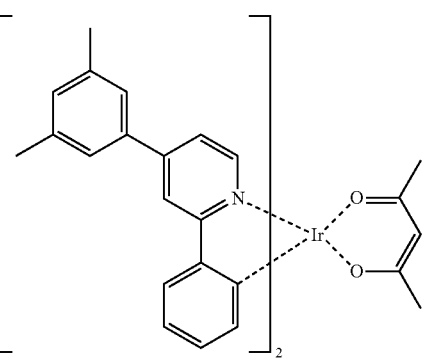
D-16
D-13
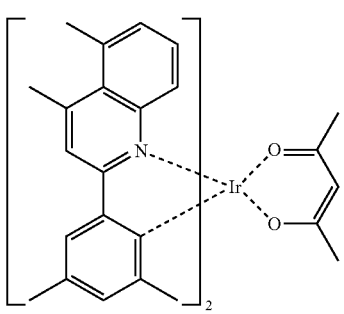
D-17

D-18
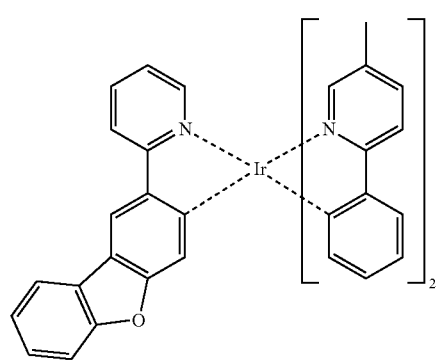
D-19
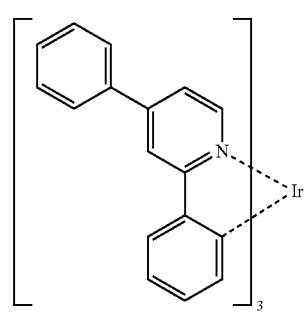
D-20
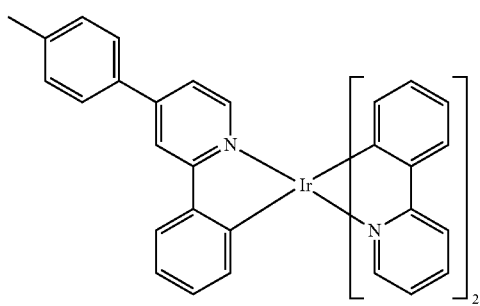
D-21
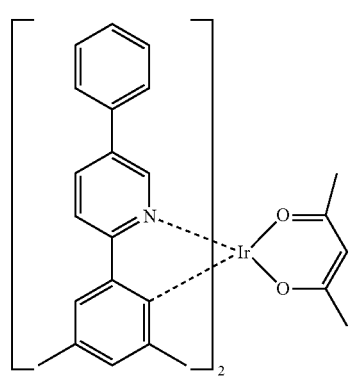
D-22
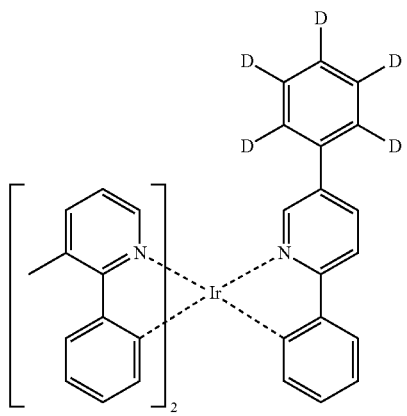
D-23
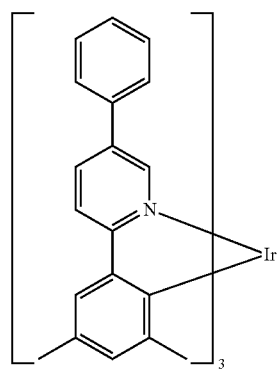
D-24
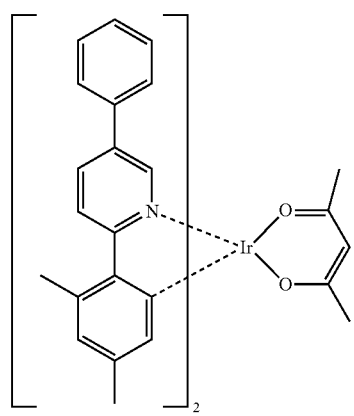
D-25
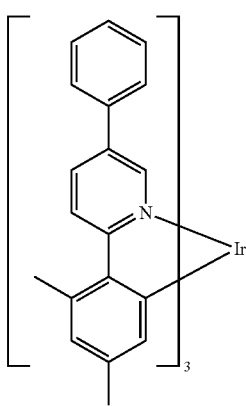

-continued
D-26
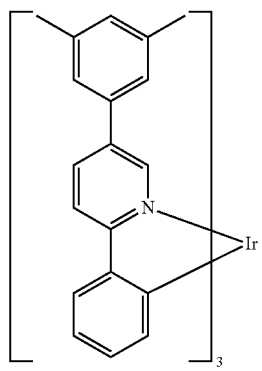
D-27
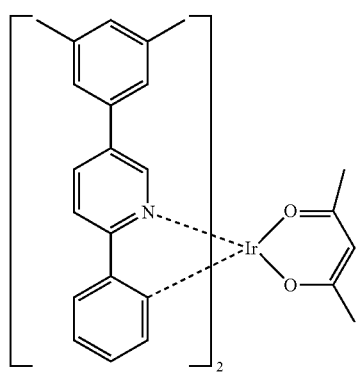
D-28
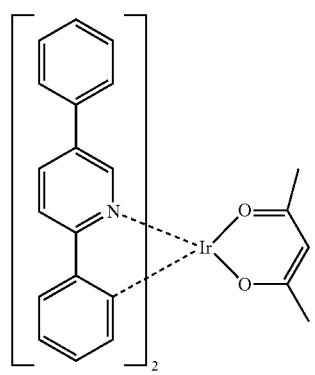
D-29
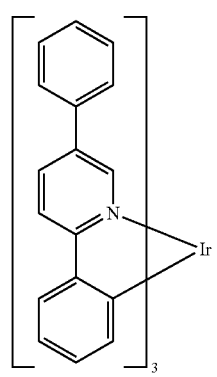
-continued
D-30
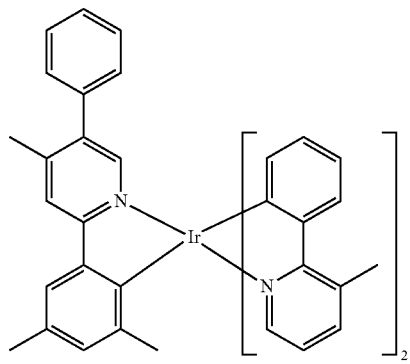
D-31
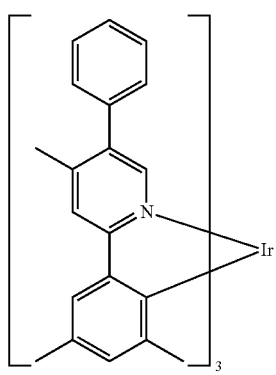
D-32
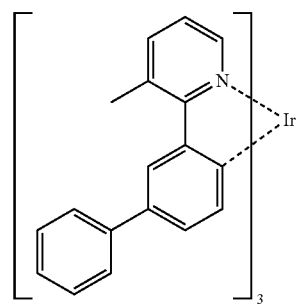
D-33
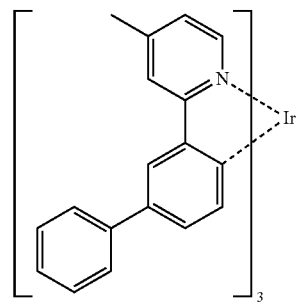

-continued
D-34
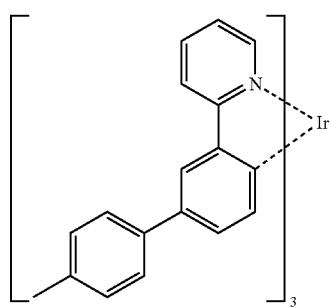
D-35
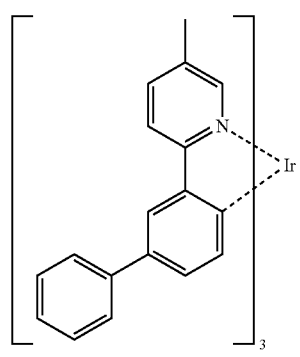
D-36
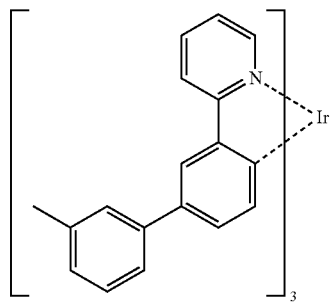
D-37
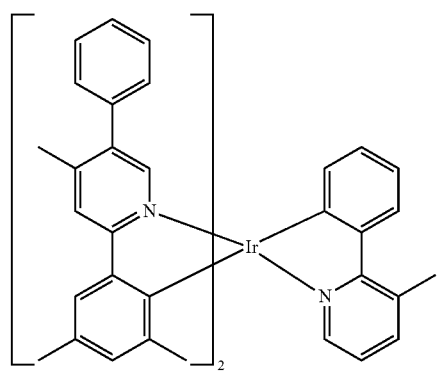
-continued
D-38
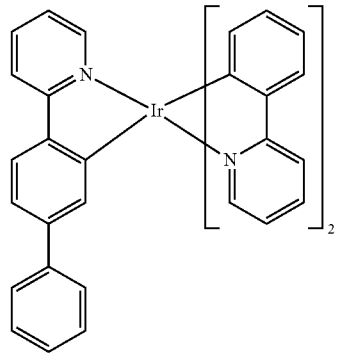
D-39
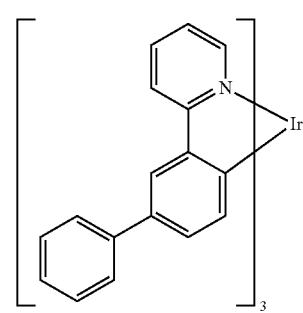
D-40
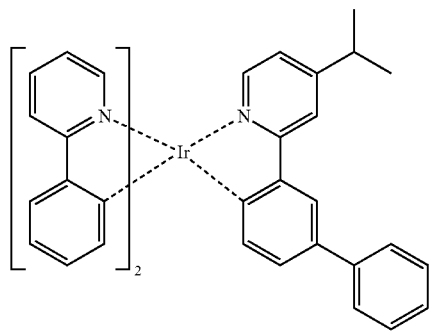
D-41
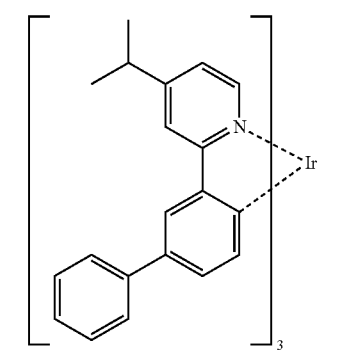
D-42
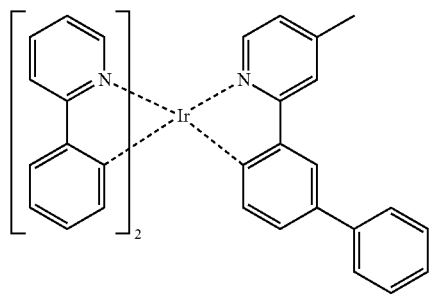

D-43 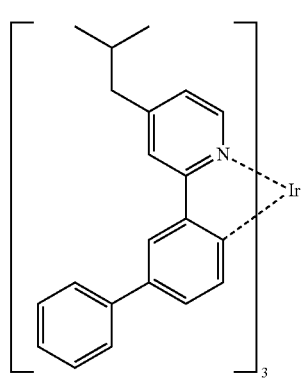
D-47 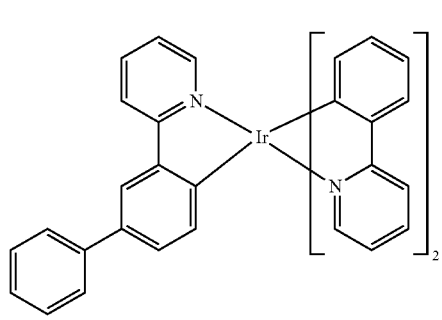
D-44 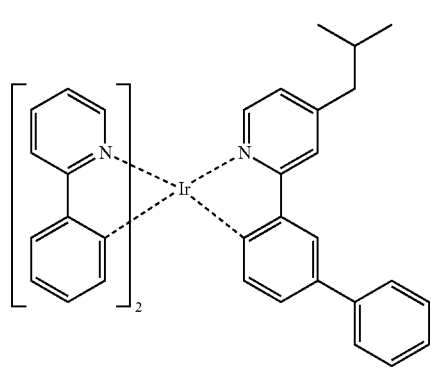
D-48 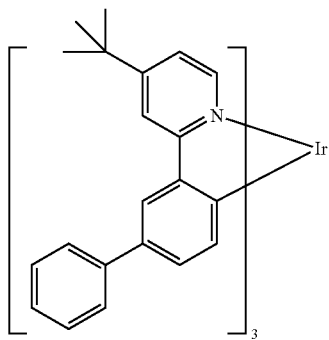
D-45 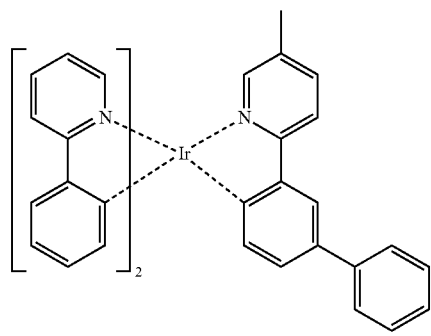
D-49 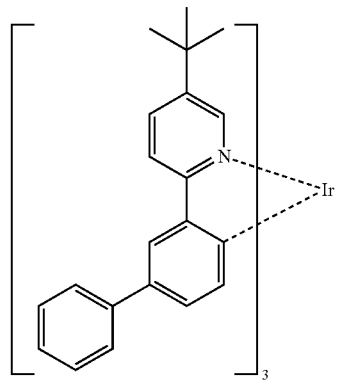
D-46 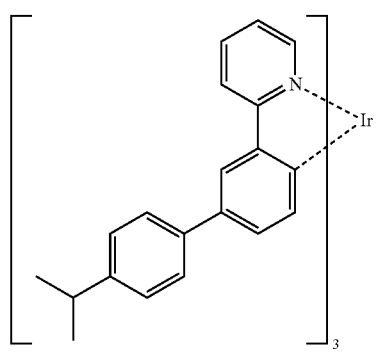
D-50 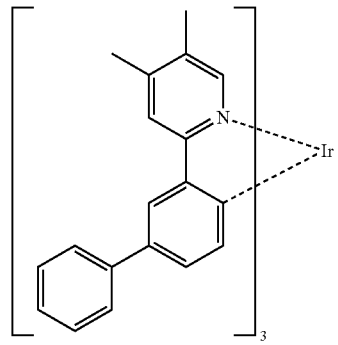

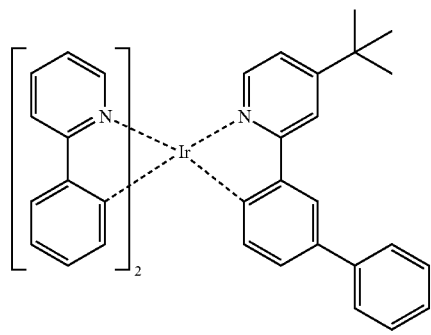
D-51
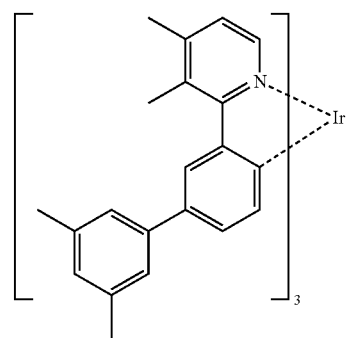
D-55
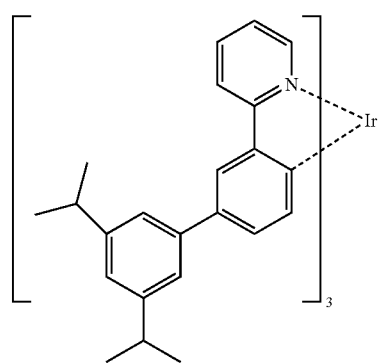
D-52
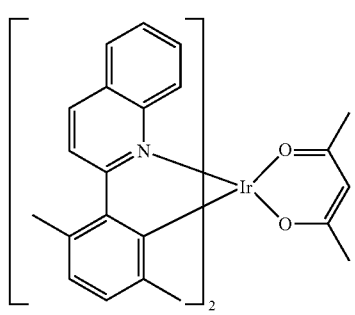
D-56
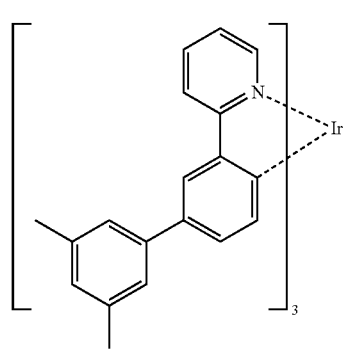
D-53
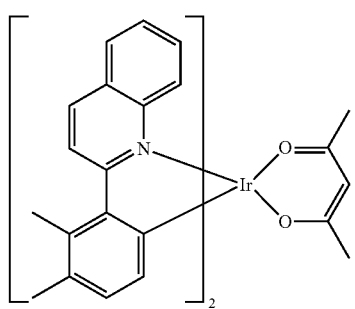
D-57
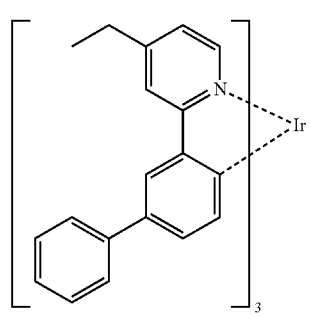
D-54
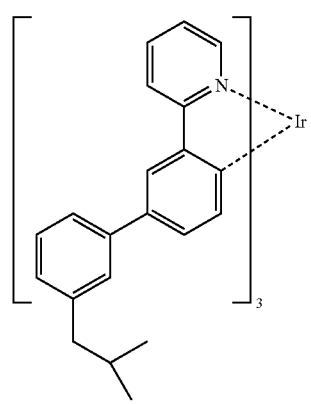
D-58

D-59
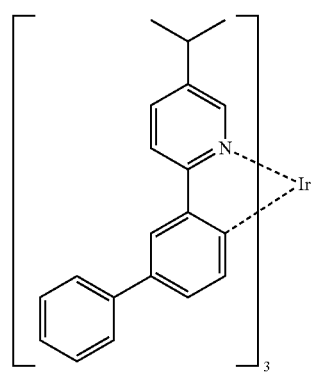
D-60
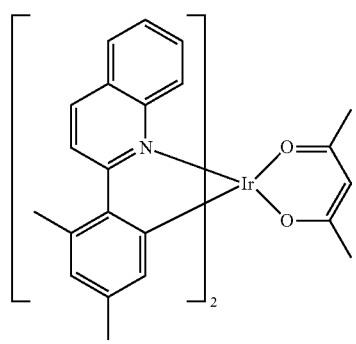
D-61
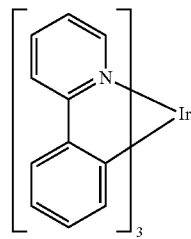
D-62
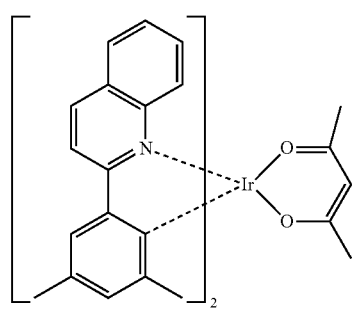
D-63
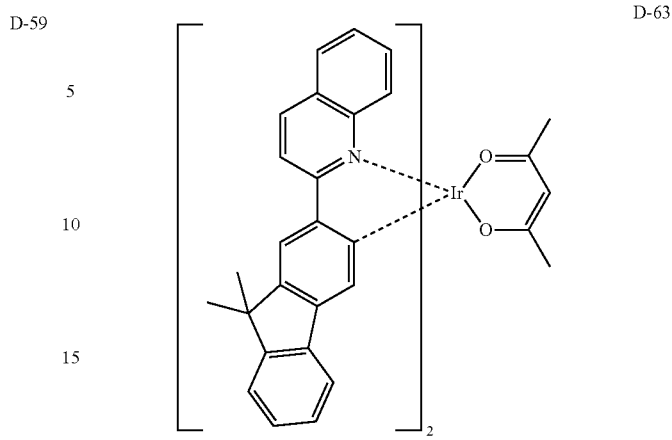
D-64
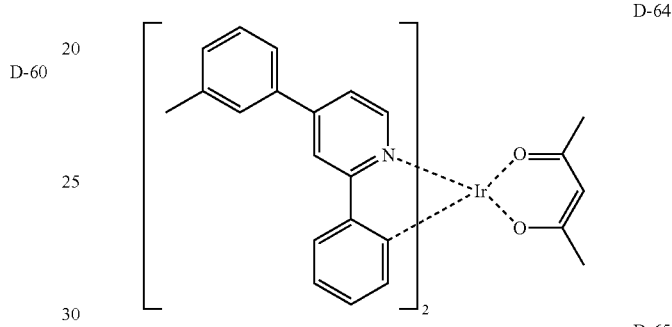
D-65
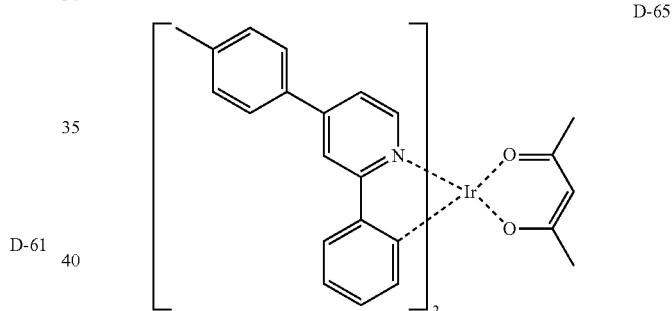
D-66
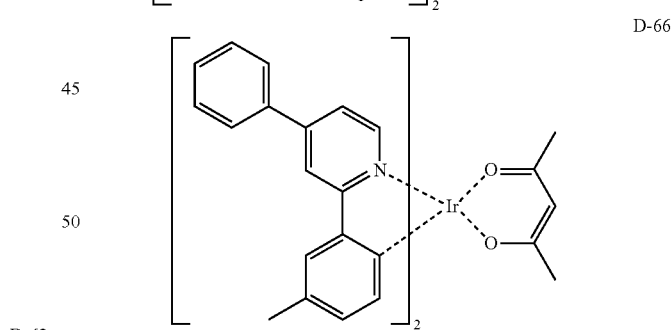
D-67
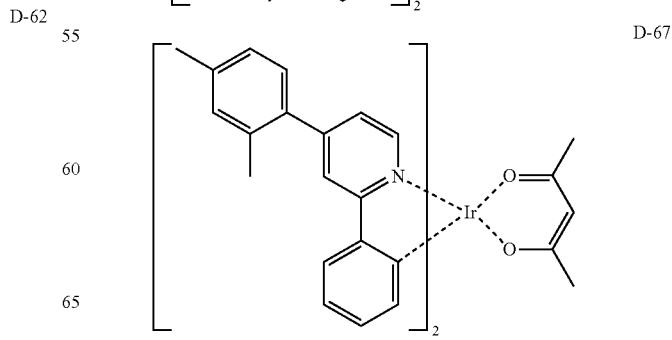

-continued
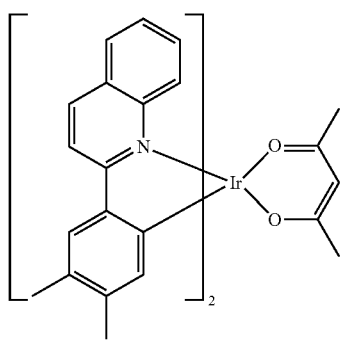
D-68
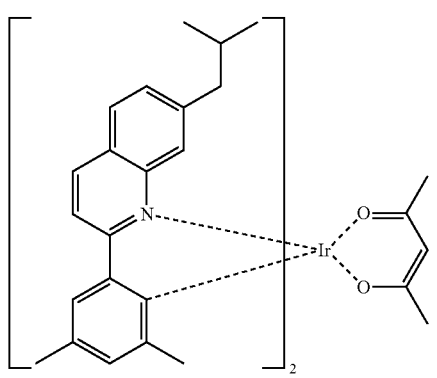
D-69
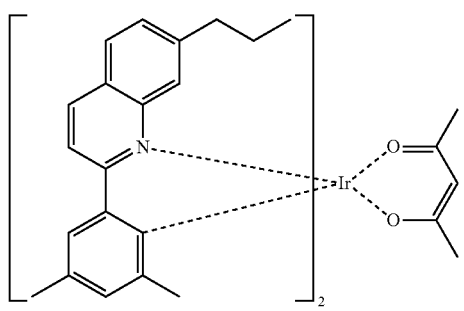
D-70
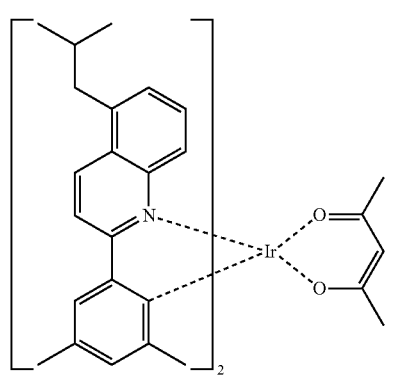
D-71
-continued
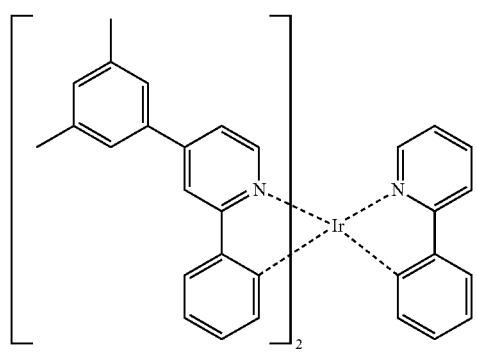
D-72
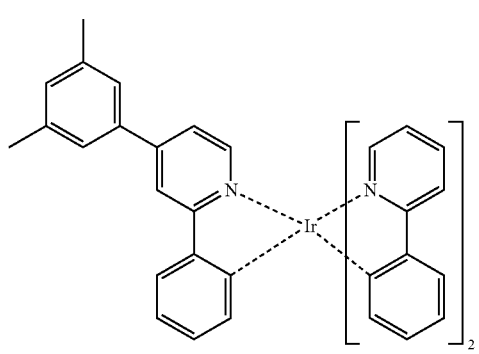
D-73
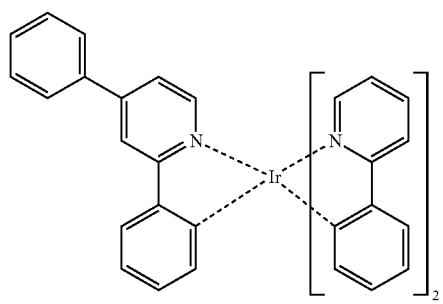
D-74
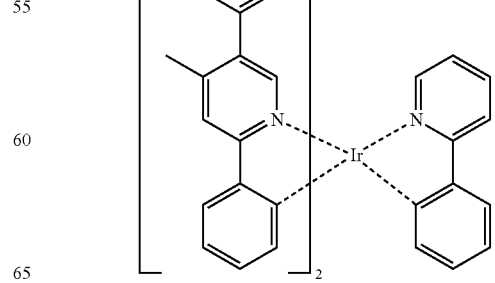
D-75

D-76
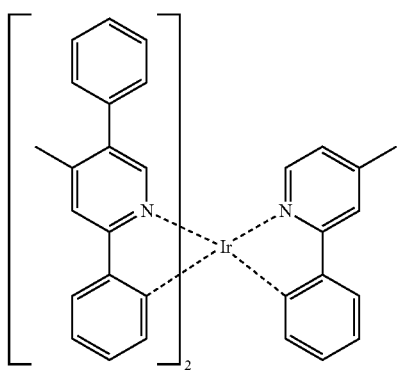
D-77
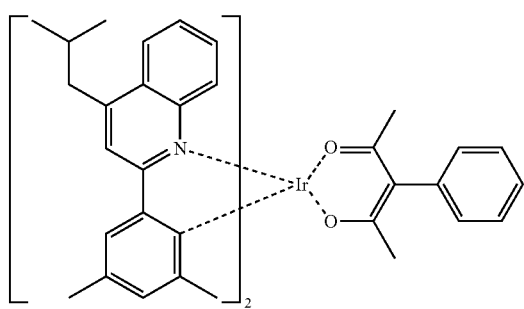
D-78
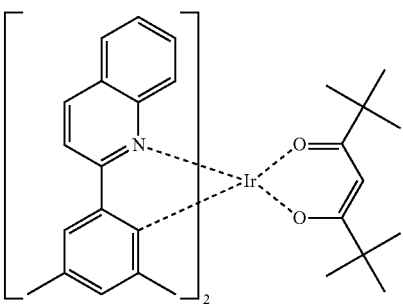
D-79
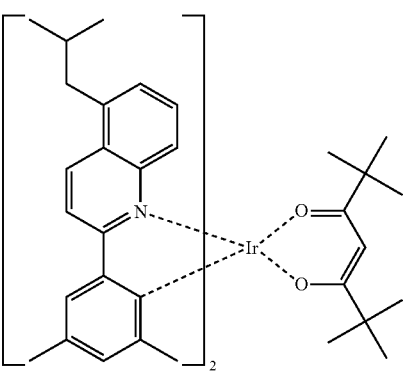
D-80
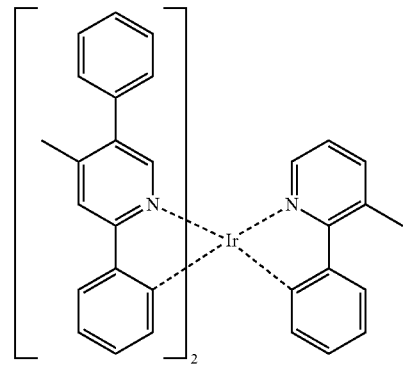
D-81
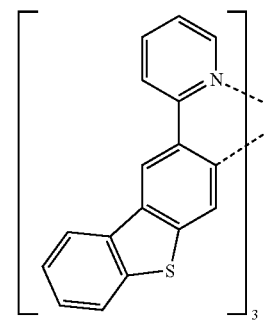
D-82
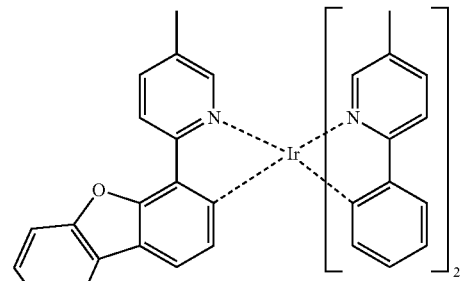
D-83
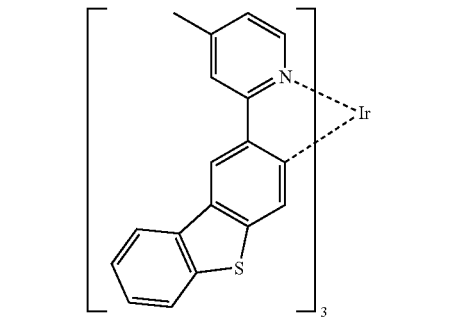
D-84
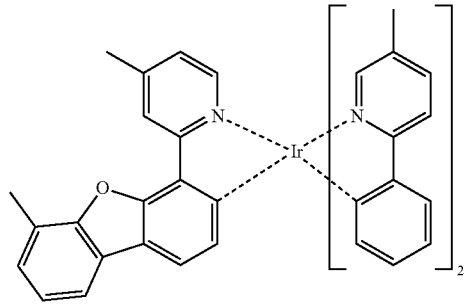

D-85 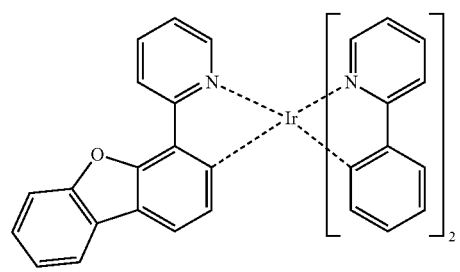
D-86 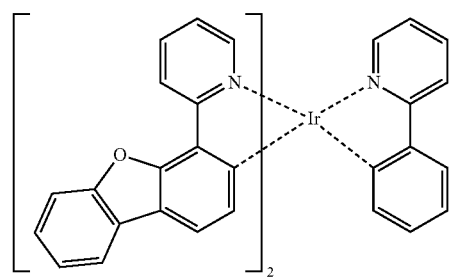
D-87 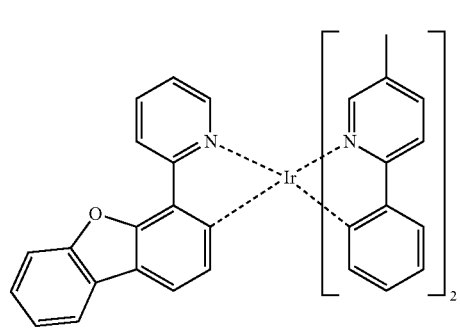
D-88 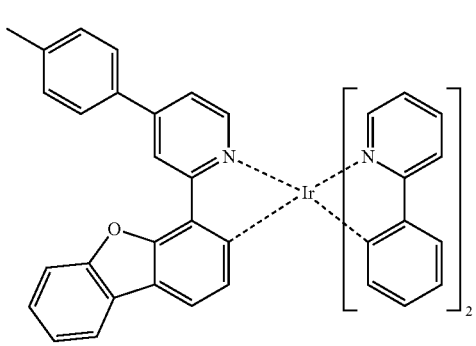
D-89 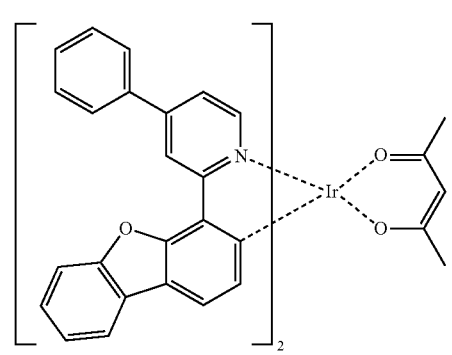
D-90 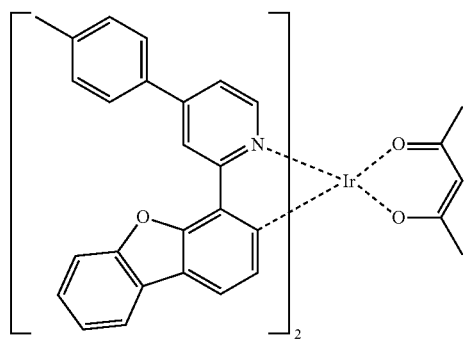
D-91 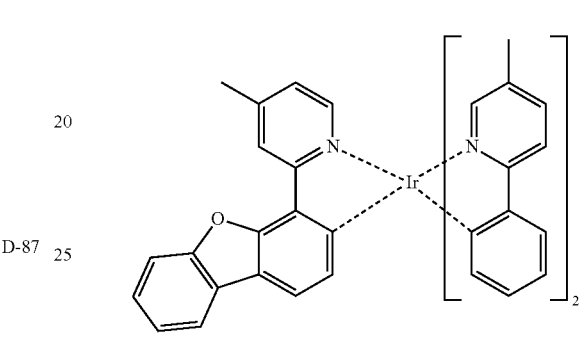
D-92 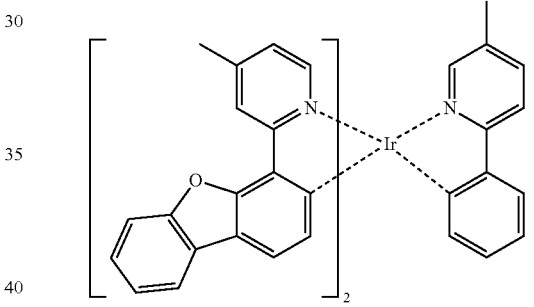
D-93 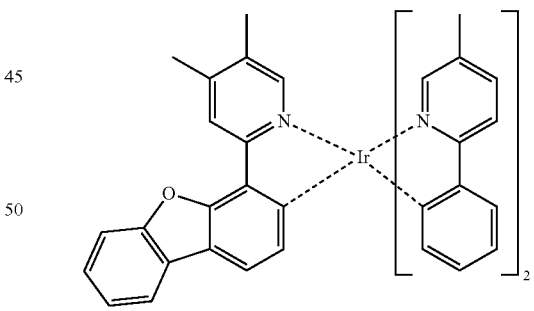
D-94 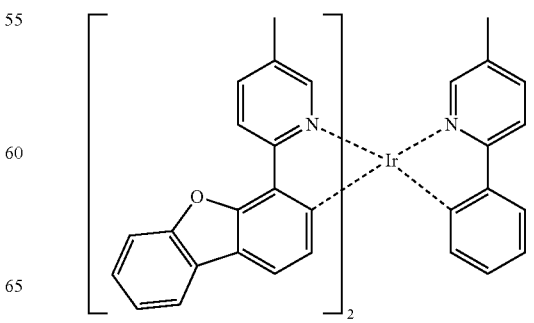

D-95
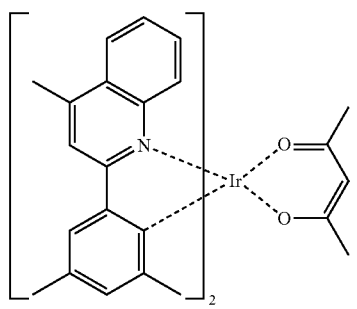
D-96
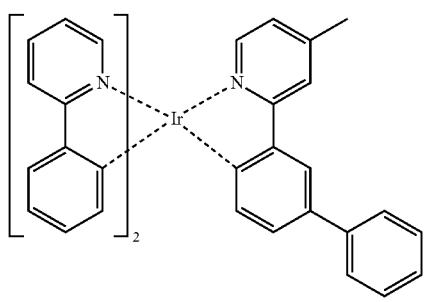
D-97
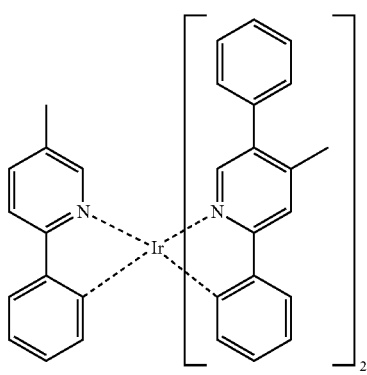
D-98
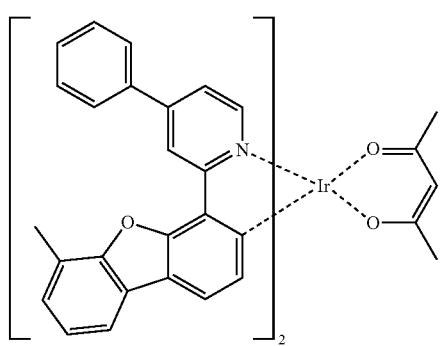
D-99
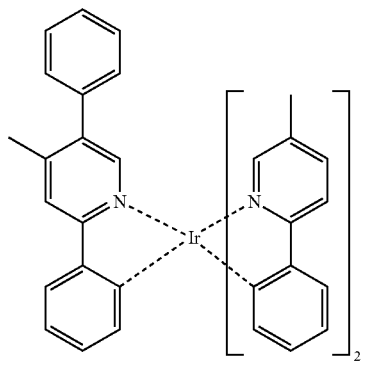
D-100
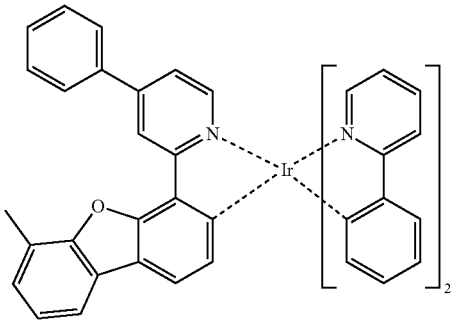
D-101
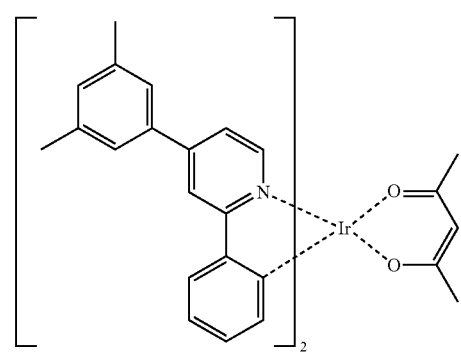
D-102
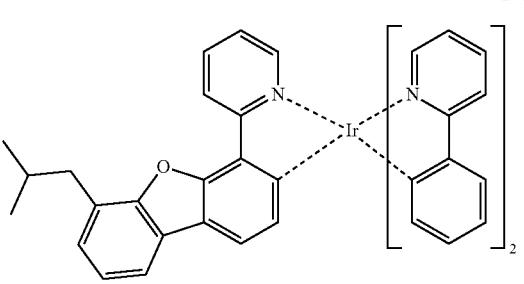

D-103
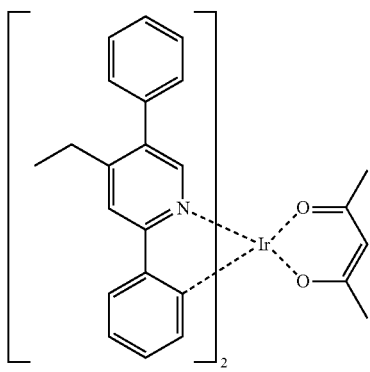
D-107
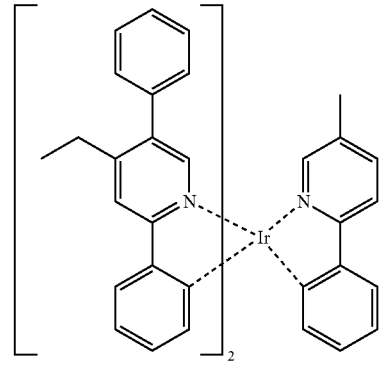
D-104
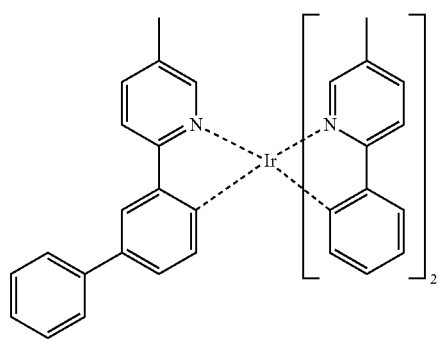
D-108
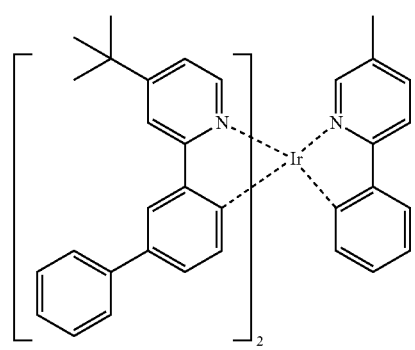
D-105
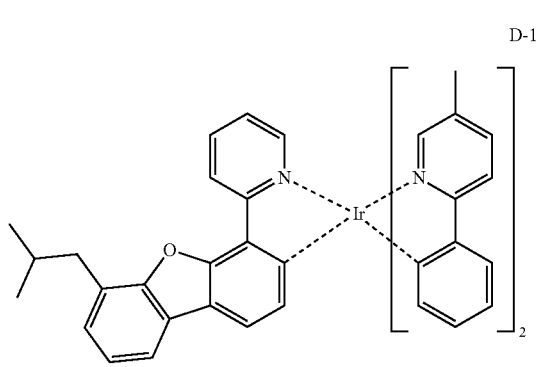
D-109
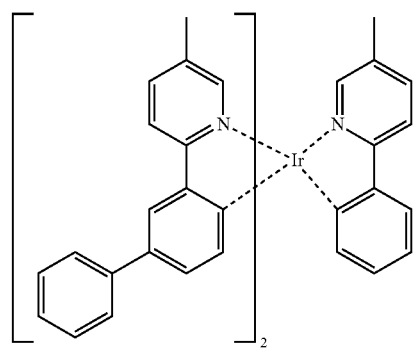
D-106
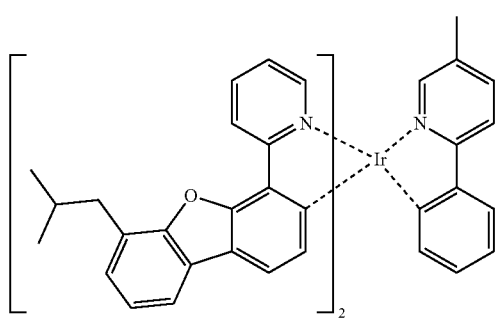
D-110
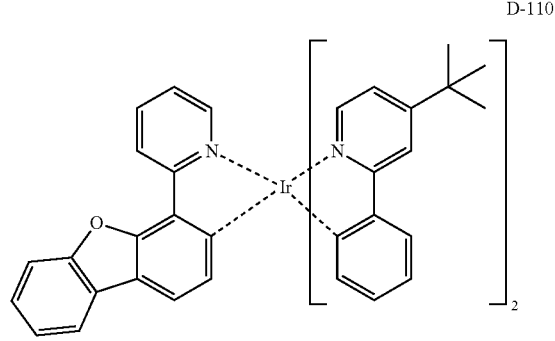

D-111
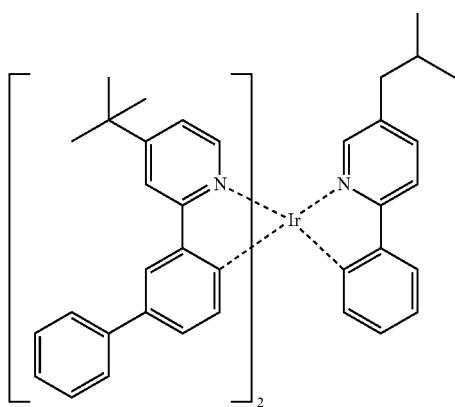
D-112
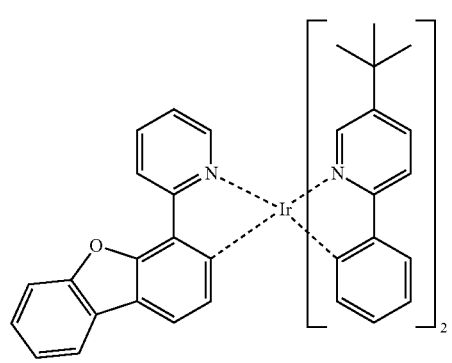
D-113
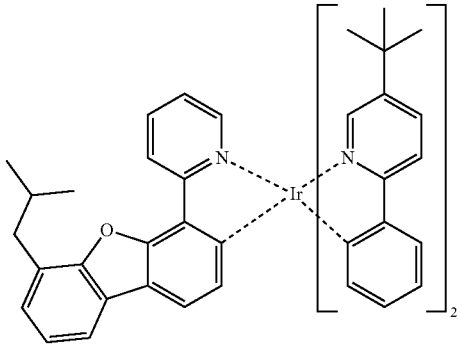
D-114
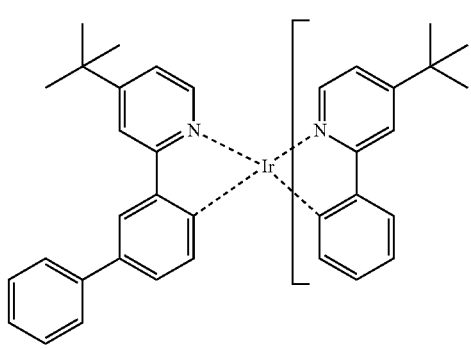
D-115
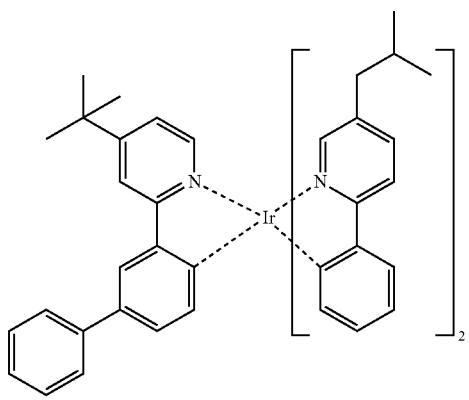
D-116
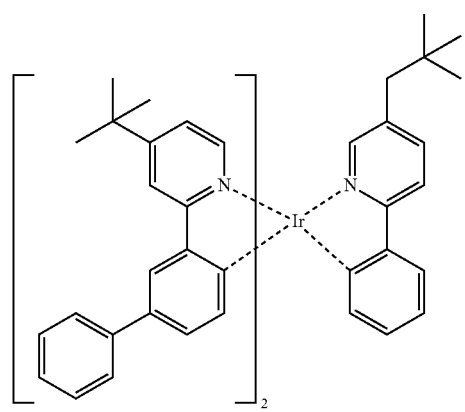
D-117
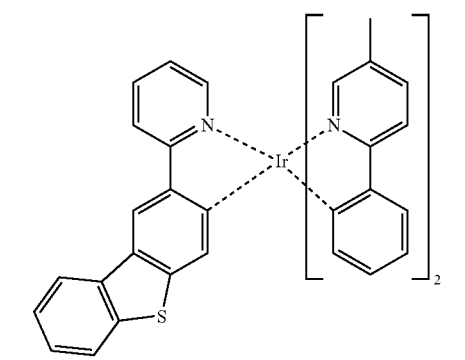
D-118
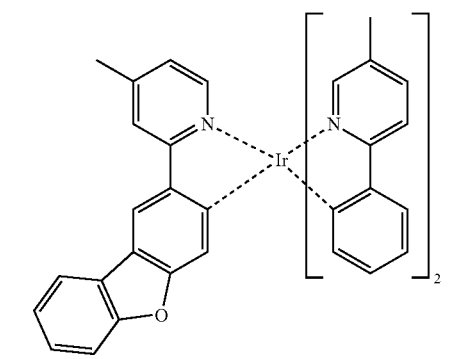

D-119
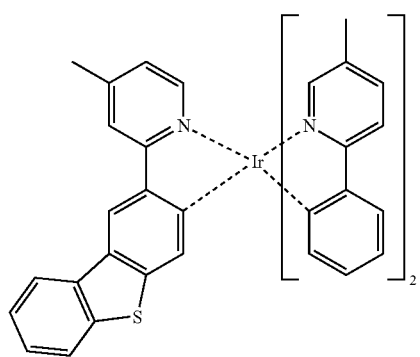
D-120
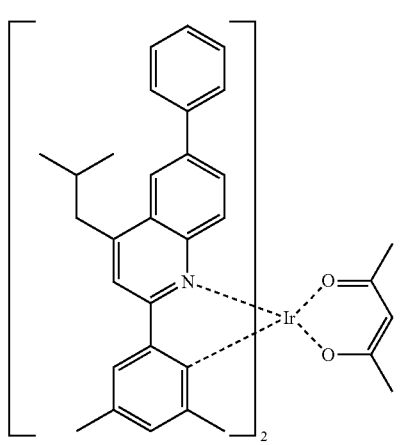
D-121
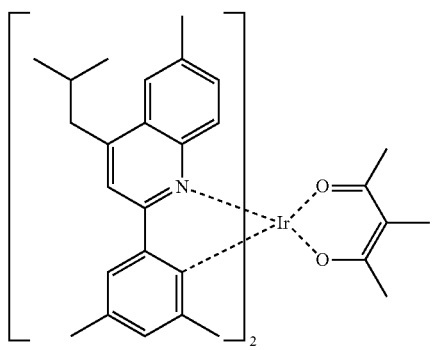
D-122
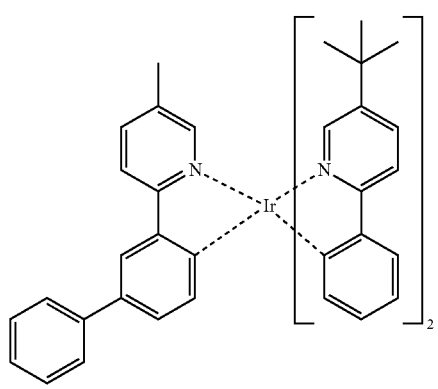
D-123
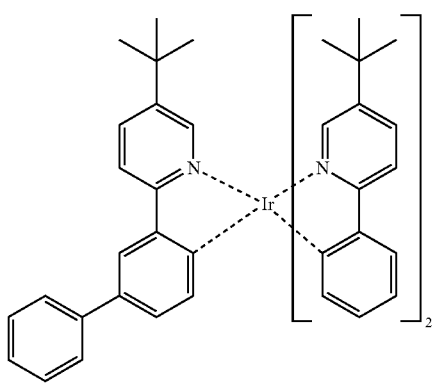
D-124
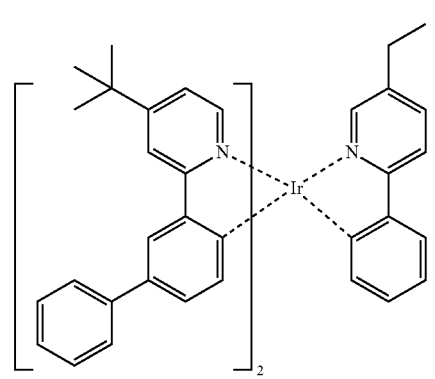
D-125
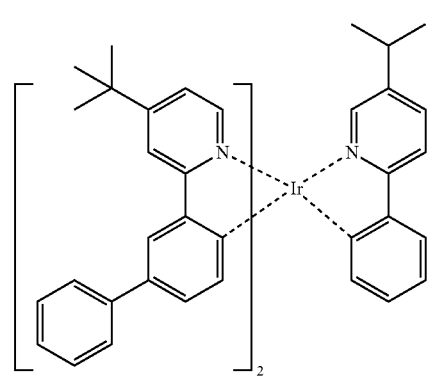
D-126
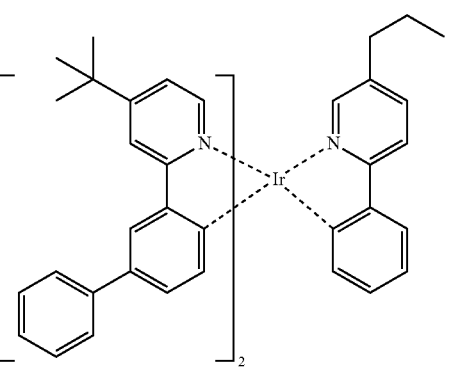

D-127
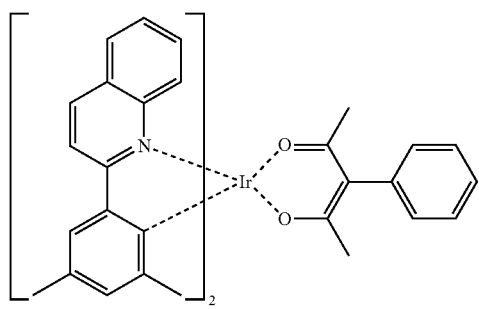
D-128
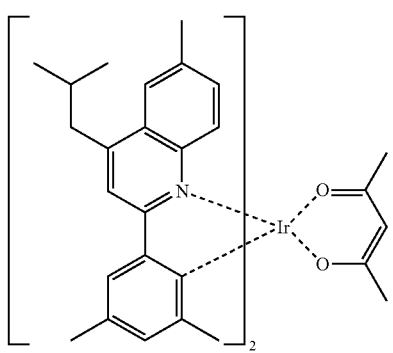
D-129
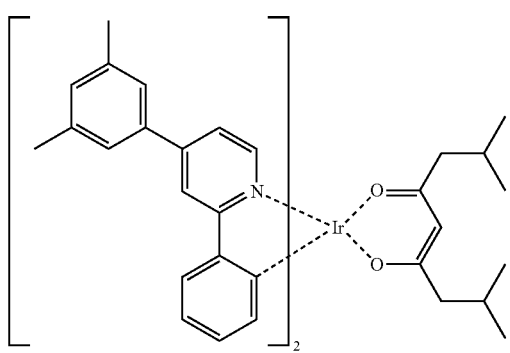
D-130
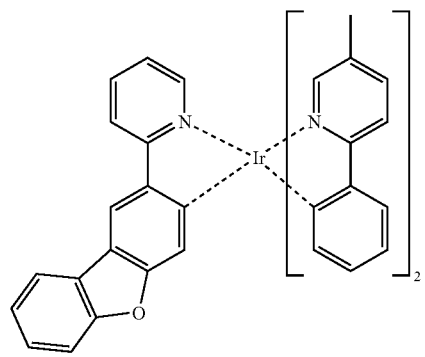
D-131
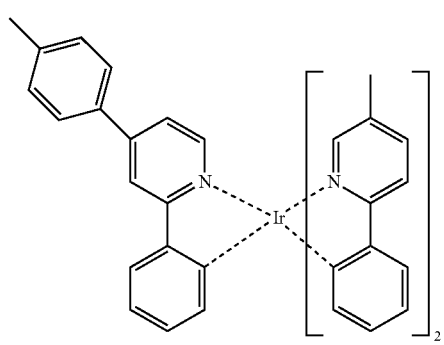
D-132
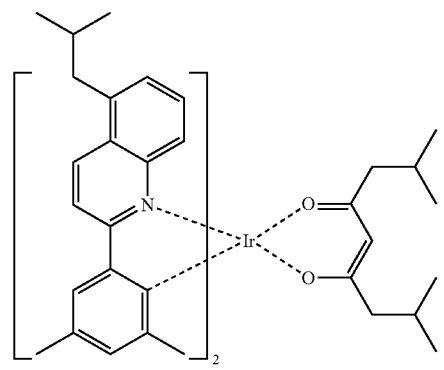
D-133
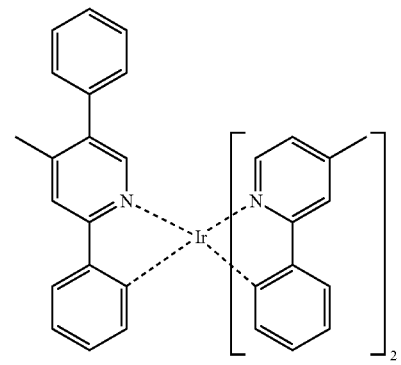
D-134
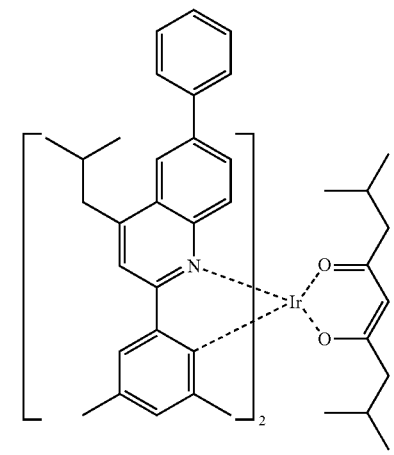

D-135
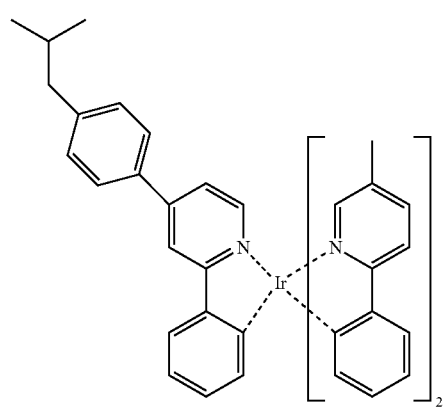
D-136
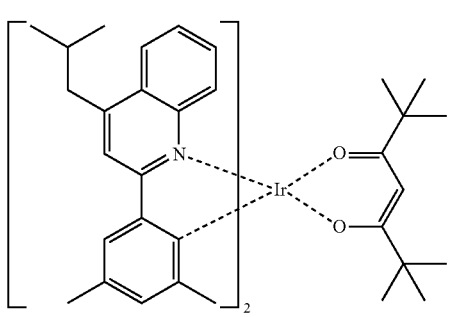
D-137
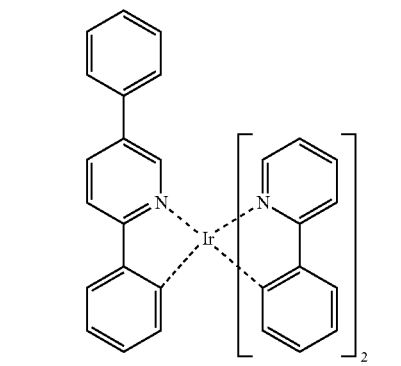
D-138
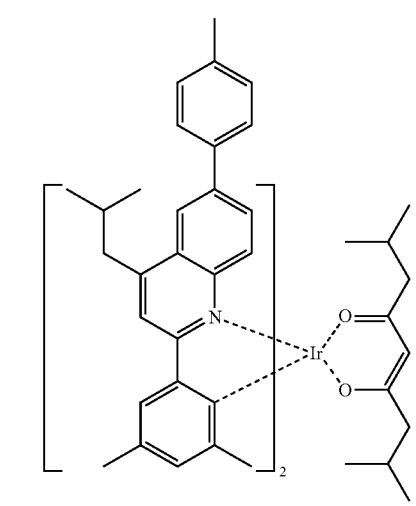
D-139
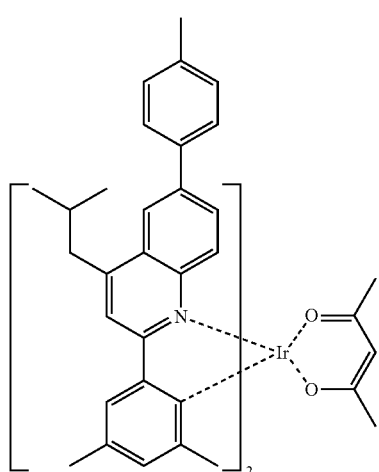
D-140
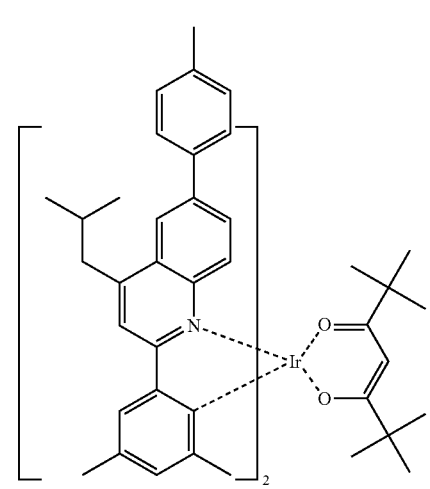
D-141
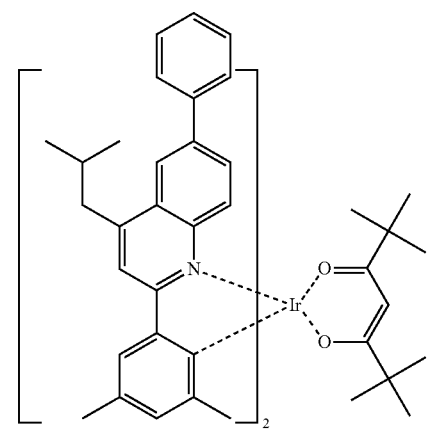

D-142

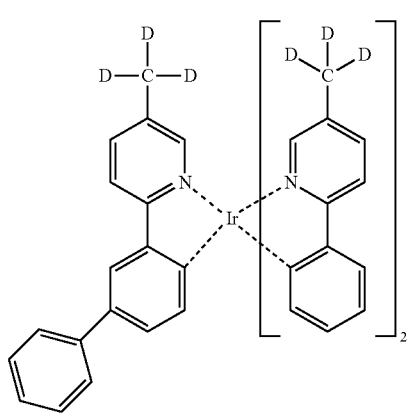

D-143

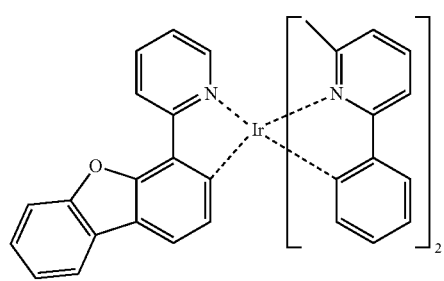

D-144

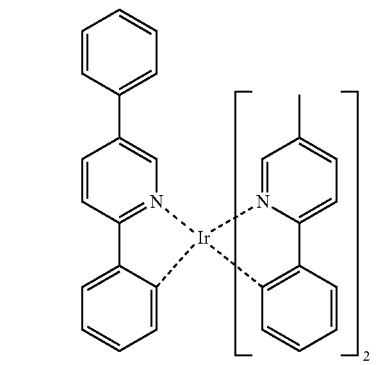

D-145

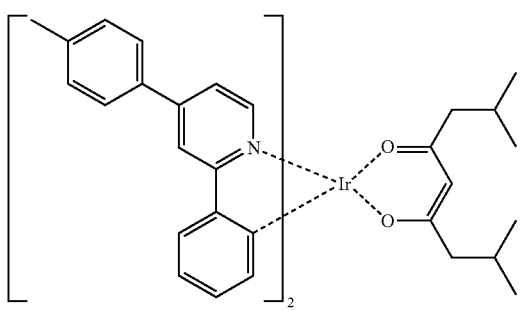

D-146

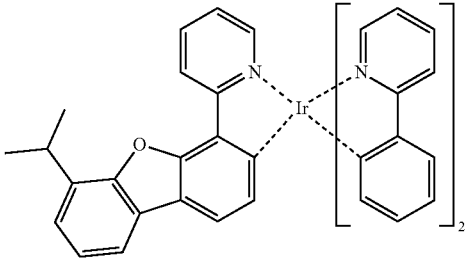

D-147

D-148

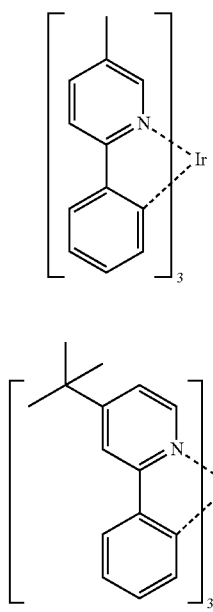

According to an additional aspect of the present disclosure, a composition for preparing an organic electroluminescent device is provided. The composition may comprise the compound of the present disclosure, as a host material or a hole transport material.

The organic electroluminescent device of the present disclosure may comprise a first electrode, a second electrode, and at least one organic layer disposed between the first and second electrodes. The organic layer may comprise a light-emitting layer, which may comprise the composition for the organic electroluminescent device of the present disclosure.

The organic electroluminescent device of the present disclosure comprises an organic electroluminescent compound of formula 1, and may further comprise at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal. The organic layer may further comprise an auxiliary light-emitting layer, a hole auxiliary layer, and a charge generating layer, besides the light-emitting layer.

In addition, the organic electroluminescent device of the present disclosure may emit white light by further comprising at least one light-emitting layer, which comprises a blue electroluminescent compound, a red electroluminescent compound or a green electroluminescent compound known in the field, besides the compound of the present disclosure. If necessary, it may further comprise an orange light-emitting layer or a yellow light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

Furthermore, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the compound of the present disclosure, the preparation method of the compound, and the luminescent properties of the device will be explained in detail with reference to the following examples.

[Example 1] Preparation of Compound C-1

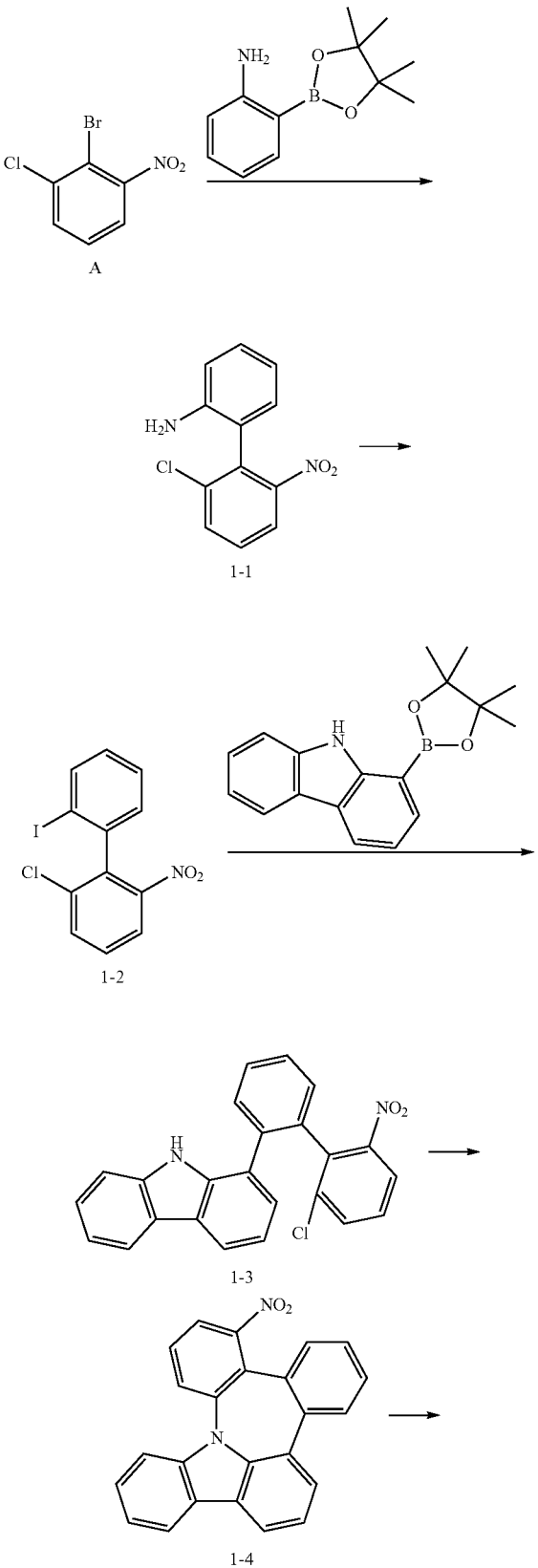

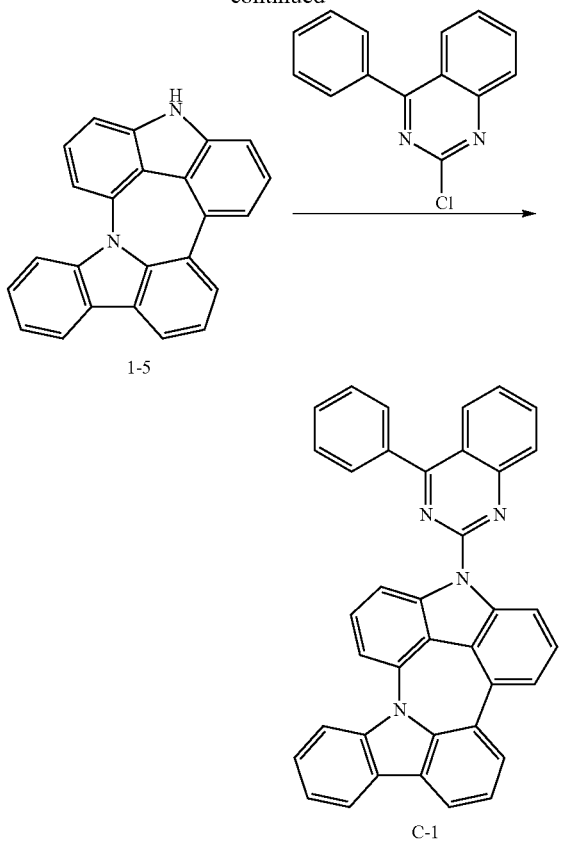

1) Preparation of Compound 1-1

After introducing compound A (36.0 g, 152.3 mmol), 2-(4,4,5,5-tetramethyl-1,3,2-dioxaboran-2-yl)aniline (40 g, 182.7 mmol), tetrakis(triphenylphosphine)palladium (5.28 g, 4.6 mmol), cesium carbonate (124.0 g, 380.6 mmol), toluene (760 mL), EtOH (190 mL), and distilled water (190 mL) into a reaction vessel, the mixture was stirred at 120° C. for 5 hours. After completion of the reaction, the mixture was washed with distilled water and extracted with ethyl acetate. The obtained organic layer was dried with magnesium sulfate and the solvent was removed therefrom by a rotary evaporator. The products were purified by column chromatography to obtain compound 1-1 (19.3 g, yield: 50.4%).

2) Preparation of Compound 1-2

After introducing compound 1-1 (19.2 g, 77.2 mmol) and acetonitrile (768 mL) into a reaction vessel, para-toluenesulfonic acid monohydrate (44.06 g, 231.6 mmol) was added at 0° C. After 10 minutes, sodium nitrite (10.66 g, 154.4 mmol) and potassium iodide (32.0 g, 193.0 mmol) were dissolved in distilled water (576 mL), and then slowly added dropwise to the mixture. After completion of the dropwise addition, the mixture was warmed slowly to room temperature and then additionally stirred for 5 hours. After completion of the reaction, an aqueous solution of sodium thiosulfate was added thereto to stop the reaction. The mixture was then extracted with ethyl acetate. The obtained organic layer was dried with magnesium sulfate and the solvent was removed therefrom by a rotary evaporator. The products were purified by column chromatography to obtain compound 1-2 (18.6 g, yield: 67.0%).

3) Preparation of Compound 1-3

After introducing compound 1-2 (18.6 g, 51.7 mmol), 1-(4,4,5,5-tetramethyl-1,3,2-dioxaboran-2-yl)-9H-carbazole (15.3 g, 62.1 mmol), tetrakis(triphenylphosphine)palladium (3.0 g, 2.6 mmol), cesium carbonate (13.7 g, 129.3 mmol), toluene (260 mL), EtOH (65 mL), and distilled water (65 mL) into a reaction vessel, the mixture was stirred at 120° C. for 4 hours. After completion of the reaction, the mixture was washed with distilled water and extracted with ethyl acetate. The obtained organic layer was dried with magnesium sulfate and the solvent was removed therefrom by a rotary evaporator. The products were purified by column chromatography to obtain compound 1-3 (11.4 g, yield: 55.3%).

4) Preparation of Compound 1-4

After introducing compound 1-3 (11.0 g, 27.6 mmol), palladium(II)acetate (3.1 g, 13.8 mmol), tri-tert-butylphosphine (11.16 g, 27.6 mmol), cesium carbonate (35.94 g, 110.4 mmol), and o-xylene (184 mL) into a reaction vessel, the mixture was stirred under reflux for 3 hours. After completion of the reaction, the mixture was washed with distilled water and extracted with ethyl acetate. The obtained organic layer was dried with magnesium sulfate and the solvent was removed therefrom by a rotary evaporator. The products were purified by column chromatography to obtain compound 1-4 (5.4 g, yield: 54.0%).

5) Preparation of Compound 1-5

After introducing compound 1-4 (5.4 g, 14.9 mmol), triphenylphosphine (11.7 g, 44.7 mmol), and 1,2-dichlorobenzene (75 mL) into a reaction vessel, the mixture was stirred at 200° C. for 8 hours. After completion of the reaction, the mixture was distilled under reduced pressure to remove the solvent. The mixture was then washed with distilled water and extracted with ethyl acetate. The obtained organic layer was dried with magnesium sulfate and the solvent was removed therefrom by a rotary evaporator. The products were purified by column chromatography to obtain compound 1-5 (4.5 g, yield: 91.3%).

6) Preparation of Compound C-1

After dissolving compound 1-5 (3.5 g, 10.6 mmol), 2-chloro-4-phenylquinazoline (3.06 g, 12.7 mmol), dimethylaminopyridine (DMAP) (0.65 g, 5.3 mmol), potassium carbonate ($K_2CO_3$) (1.47 g, 10.6 mmol), and dimethyl formamide (53 mL) into a reaction vessel, the mixture was stirred at 155° C. for 4 hours. After completion of the reaction, the mixture was cooled to between 5° C. and 10° C. Then, MeOH (50 mL) and distilled water (60 mL) were added thereto, the mixture was stirred for 30 minutes, and then filtered to obtain compound C-1 (5.4 g, yield: 95.3%).

| | MW (Molecular Weight) | UV | PL | M.P. (Melting Point) |
|---|---|---|---|---|
| C-1 | 534.62 | 404 nm | 519 nm | 265° C. |

[Device Example 1] OLED Comprising the Compound of the Present Disclosure as a Host An OLED was produced using the organic electroluminescent compound of the present disclosure as follows. A transparent electrode indium tin oxide (ITO) thin film (10 Ω/sq) on a glass substrate for an organic electroluminescent device (OLED) (Geomatec) was subjected to an ultrasonic washing with acetone and isopropanol sequentially and was then stored in isopropanol. The ITO substrate was then mounted on a substrate holder of a vacuum vapor depositing apparatus. Compound HIL-1 was introduced into a cell of the vacuum vapor depositing apparatus and then the pressure in the chamber of the apparatus was controlled to $10^{-6}$ torr. Thereafter, an electric current was applied to the cell to evaporate compound HIL-1, thereby forming a first hole injection layer having a thickness of 80 nm on the ITO substrate. Compound HIL-2 was then introduced into another cell of the vacuum vapor depositing apparatus and evaporated by applying electric current to the cell, thereby forming a second hole injection layer having a thickness of 5 nm on the first hole injection layer. Compound HTL-1 was introduced into one cell of the vacuum vapor depositing apparatus and evaporated by applying electric current to the cell, thereby forming a first hole transport layer having a thickness of 10 nm on the second hole injection layer. Compound HTL-2 was then introduced into another cell of the vacuum vapor depositing apparatus and evaporated by applying electric current to the cell, thereby forming a second hole transport layer having a thickness of 60 nm on the first hole transport layer. After forming the hole injection layer and the hole transport layer, a light-emitting layer was deposited thereon as follows. Compound C-1 was introduced, as a host material, into a cell of the vacuum vapor depositing apparatus and compound D-71 was introduced into another cell. The two compounds were then evaporated at different rates, so that the dopant was deposited in a doping amount of 3 wt % based on the total amount of the host and dopant to form a light-emitting layer having a thickness of 40 nm on the hole transport layer. Compounds ETL-1 and Liq were then introduced into another two cells of the vacuum vapor depositing apparatus, respectively, and evaporated at the same rate of 1:1, thereby forming an electron transport layer having a thickness of 30 nm on the light-emitting layer. After depositing compound Liq as an electron injection layer having a thickness of 2 nm on the electron transport layer, an Al cathode having a thickness of 80 nm was then deposited by another vacuum vapor deposition apparatus on the electron injection layer to produce the OLED.

HIL-2

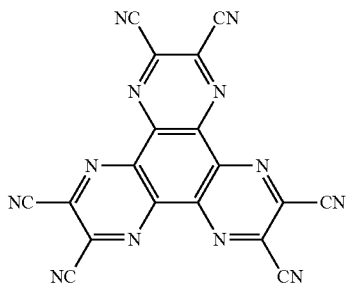

HTL-1

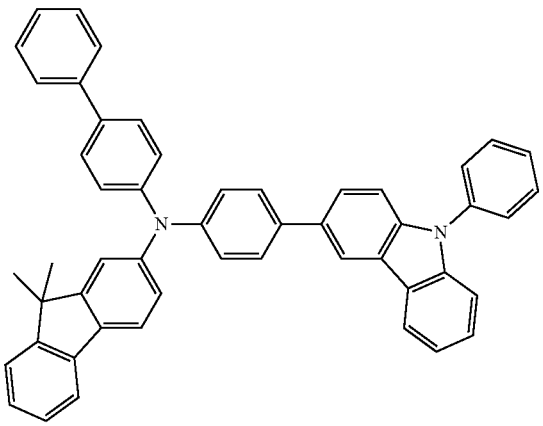

HTL-2

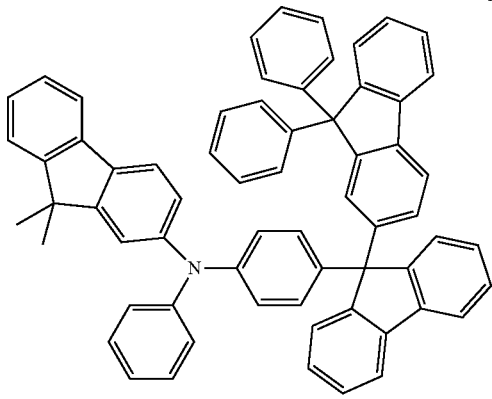

HIL-1

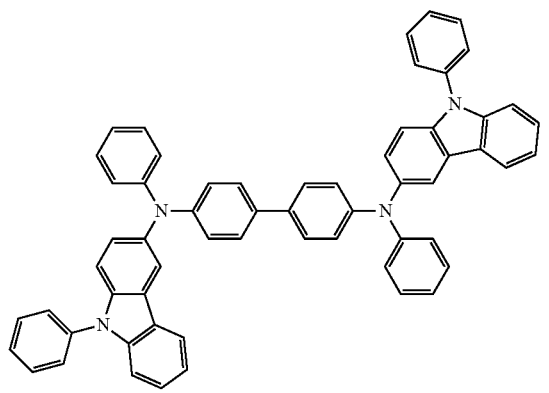

ETL-1

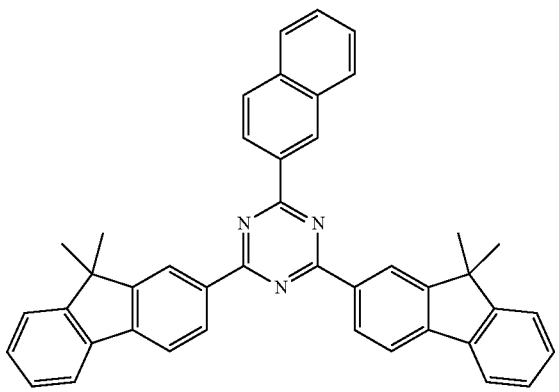

-continued

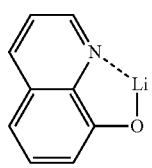

Liq

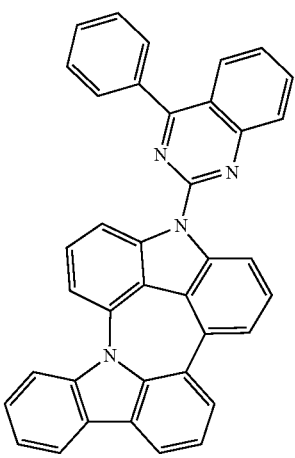

C-1

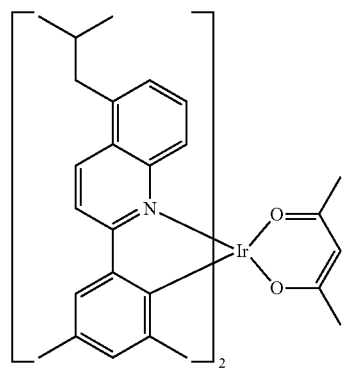

D-71

When an initial luminance at 5000 nit and a constant current is set at 100%, the time taken to be 98% of the luminance was 80 hours or more.

[Comparative Device Example 1] OLED Comprising a Conventional Organic Electroluminescent Compound An OLED was produced in the same manner as in Device Example 1, except for using the following compound B-1 as a host for a light-emitting layer.

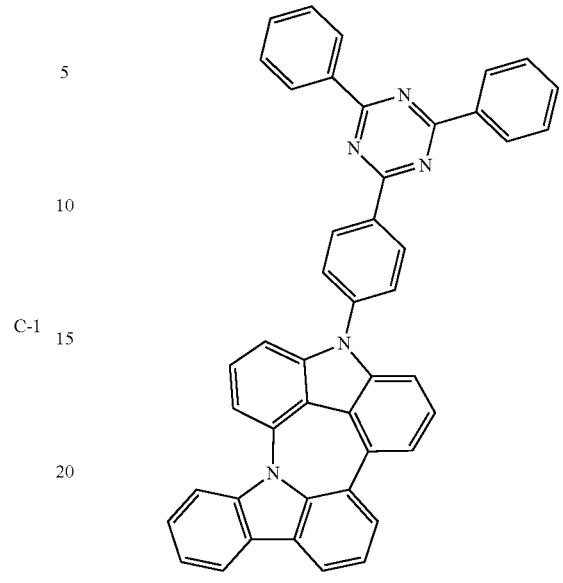

B-1

In Comparative Device Example 1, when an initial luminance at 5000 nit and a constant current is set at 100% as in Device Example 1, the time taken to be 98% of the luminance was 40 hours or more.

As confirmed by the Device Example and the Comparative Device Example, the OLED employing the organic electroluminescent compound of the present disclosure has better properties including more improved lifespan than the conventional OLED employing the conventional organic electroluminescent compound. Compound B-1 used in Comparative Device Example 1 or triazine derivatives suggested in the above-mentioned Korean Patent Application Laying-Open No. 10-2015-077220 has a planar structure, and thereby, has good driving voltage. However, they have insufficient thermal stability, since they have high Ts (Sublimation Temperature) due to strong molecular interactions by said planar structure. Furthermore, the triazine has relatively short conjugation length, and such short conjugation results in instability of material itself, since the function of the conjugation is to stabilize electrons (radicals).

On the other hand, the organic electroluminescent compound of the present disclosure has a naphthalene-based substituent in the substituent position corresponding to the triazine, such as a quinazoline or a quinoxaline. The naphthalene-based substituent has a non-planar structure relative to the triazine, and thereby, it may give higher driving voltage relative to the triazine. In addition, the naphthalene-based substituent, in contrast to the triazine, has low Ts and longer conjugation length relative to the triazine, and thereby, it may give superior heat stability and electron stabilization properties to the triazine.

The effects of the present disclosure confirmed by the Device Example and the Comparative Device Example may be considered in that the intermediate properties, between the naphthalene-based substituent and the triazine, of the organic electroluminescent compound of the present disclosure having the naphthalene-based substituent in the substituent position corresponding to the triazine, comprehensively affect lifespan of the OLED of the present disclosure, and thereby, the OLED of the present disclosure may have superior lifespan to the conventional OLED, due to the presence of the naphthalene-based substituent in the organic electroluminescent compound of the present disclosure.

The invention claimed is:
1. An organic electroluminescent compound represented by the following formula

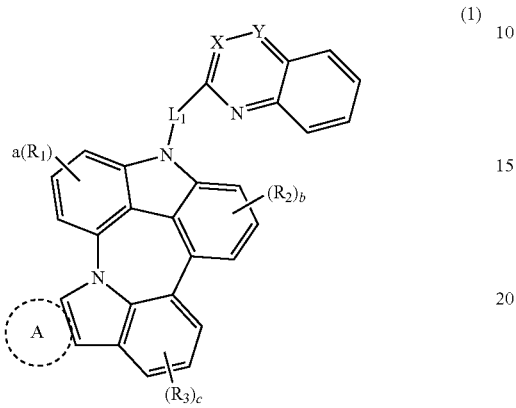

(1)

wherein
X and Y, each independently, represent CR$_4$ or N;
L$_1$ represents a single bond, a substituted or unsubstituted (C6-C30)arylene, or a substituted or unsubstituted (3- to 30-membered) heteroarylene;
A represents a substituted or unsubstituted (C6-C30)aryl, or a substituted or unsubstituted (3- to 30-membered) heteroaryl;
R$_1$, R$_2$, and R$_3$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or two or more R$_1$'s may be linked to an adjacent substituent(s) to form a substituted or unsubstituted (3 to 30-membered), mono- or polycyclic, alicyclic or aromatic ring, or a fused ring of the alicyclic ring and the aromatic ring, whose carbon atom(s) may be replaced with at least one heteroatom selected from the group consisting of nitrogen, oxygen, and sulfur; or two or more R$_2$'s may be linked to an adjacent substituent(s) to form a substituted or unsubstituted (3 to 30-membered), mono- or polycyclic, alicyclic or aromatic ring, or a fused ring of the alicyclic ring and the aromatic ring, whose carbon atom(s) may be replaced with at least one heteroatom selected from the group consisting of nitrogen, oxygen, and sulfur; or two or more R$_3$'s may be linked to an adjacent substituent(s) to form a substituted or unsubstituted (3 to 30-membered), mono- or polycyclic, alicyclic or aromatic ring, or a fused ring of the alicyclic ring and the aromatic ring, whose carbon atom(s) may be replaced with at least one heteroatom selected from the group consisting of nitrogen, oxygen, and sulfur;

R$_4$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

wherein the heteroaryl(ene) contains one or more heteroatoms selected from the group consisting of B, N, O, S, Si, and P;

a, b, and c, each independently, represent an integer of 1 to 3, and when a, b, or c is an integer of 2 or more, each of R$_1$, R$_2$ or R$_3$ may be the same or different.

2. The organic electroluminescent compound according to claim 1, wherein the organic electroluminescent compound of formula 1 is represented by any of the following formulae 2, 3, 6, 7, 8, and 9:

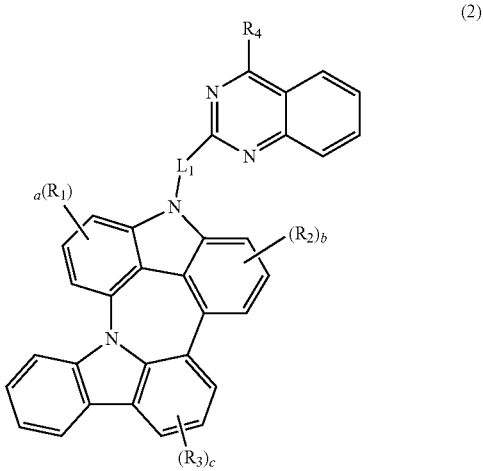

(2)

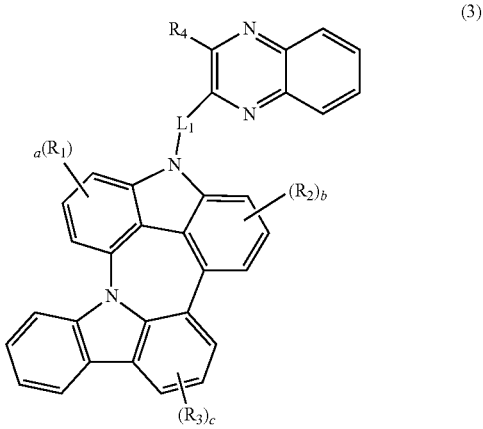

(3)

(6) 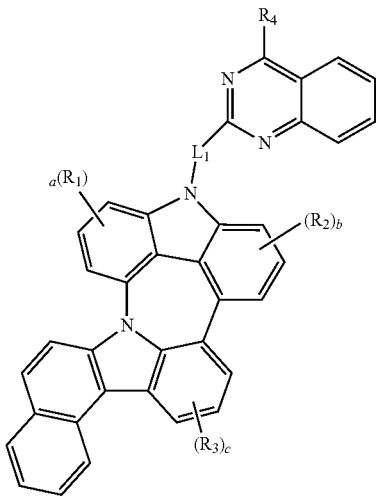

(7) 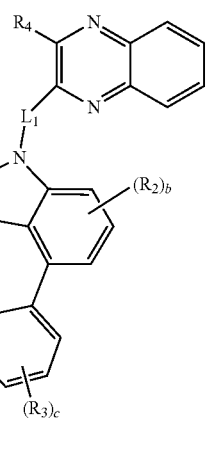

(8) 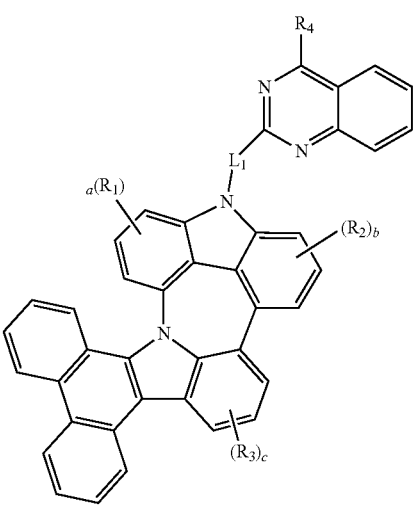

(9) 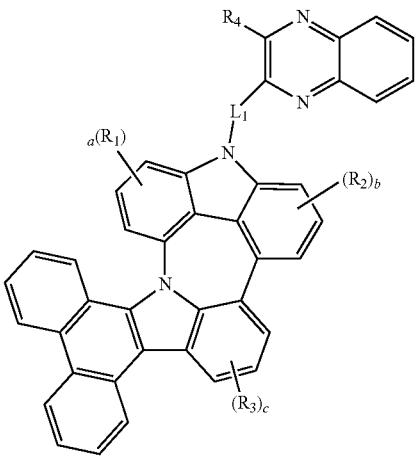

wherein $L_1$, $R_1$, $R_2$, $R_3$, $R_4$, a, b, and c are as defined in claim 1.

3. The organic electroluminescent compound according to claim 1, wherein the organic electroluminescent compound of formula 1 is represented by the following formula 10:

(10) 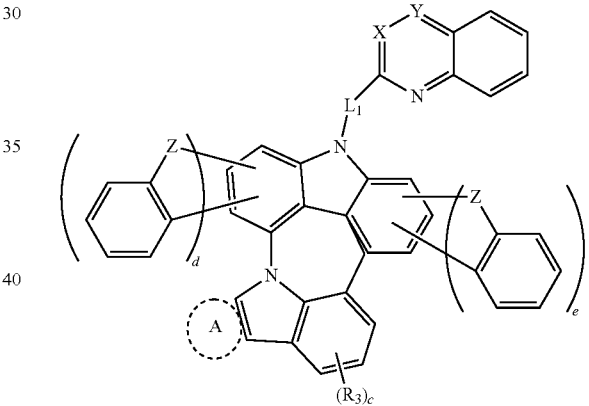

wherein

X, Y, $L_1$, A, $R_3$, and c are as defined in claim 1,

Z represents O, S, $CR_5R_6$, or $NR_7$, $R_5$, $R_6$, and $R_7$, each independently, are the same as $R_4$ defined in claim 1, and d and e, each independently, represent an integer of 0 or 1.

4. The organic electroluminescent compound according to claim 1, wherein in the $L_1$, A, $R_1$, $R_2$, $R_3$, and, $R_4$, the substituent of the substituted aryl(ene), the substituted heteroaryl(ene), the substituted alkyl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic or aromatic ring, or a fused ring of the alicyclic ring and the aromatic ring, each independently, is at least one selected from the group consisting of deuterium; a halogen; a cyano; a carboxy; a nitro; a hydroxy; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3 to 7-membered) heterocycloalkyl; a (C6-C30)aryloxy; a (C6-C30)arylthio; a (3 to 30-membered) heteroaryl substituted or unsubstituted with a (C1-C30)alkyl or a (C6-C30)aryl; a (C6-C30)aryl substituted or unsubstituted with a (3 to 30-membered) heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

5. The organic electroluminescent compound according to claim 1, wherein the compound represented by formula 1 is selected from the group consisting of:

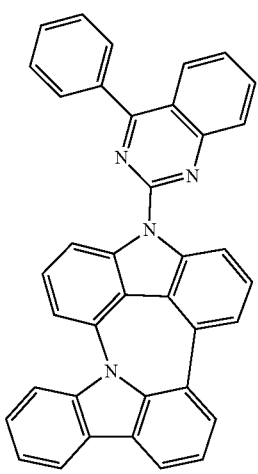

C-1

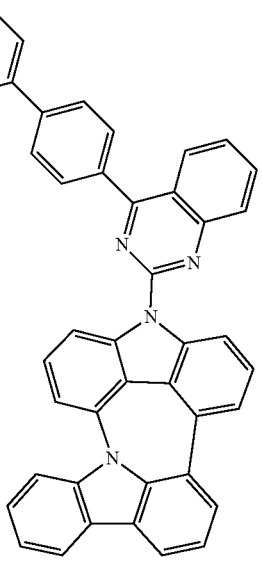

C-2

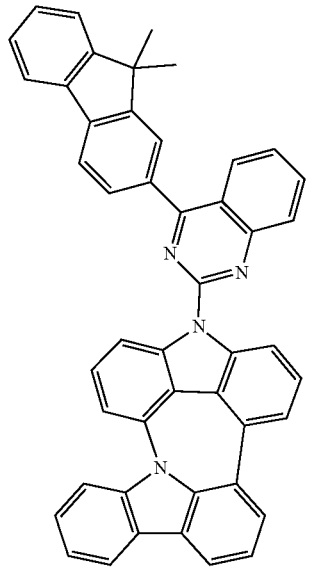

C-3

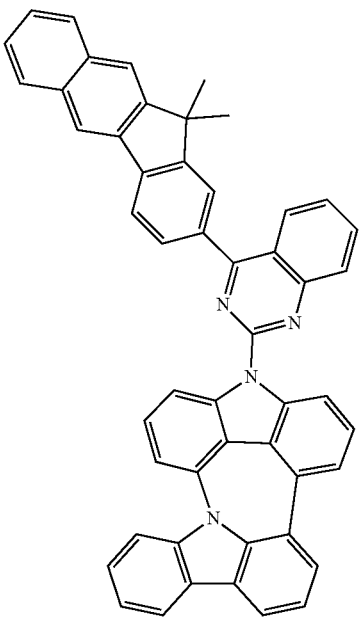

C-4

C-5
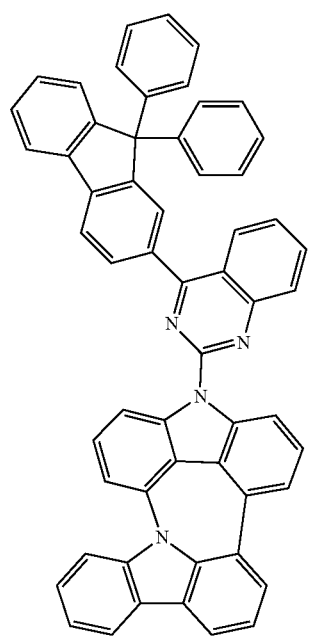
C-7
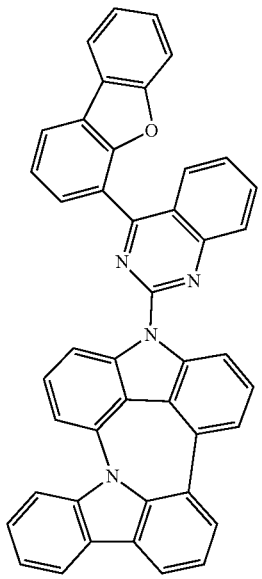
C-6
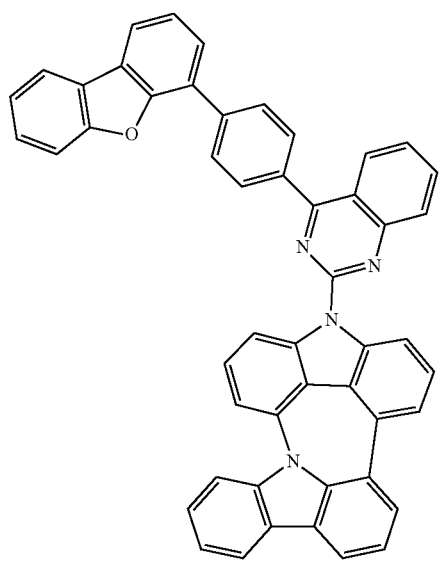
C-8
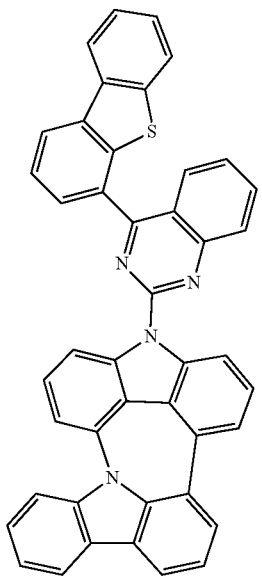

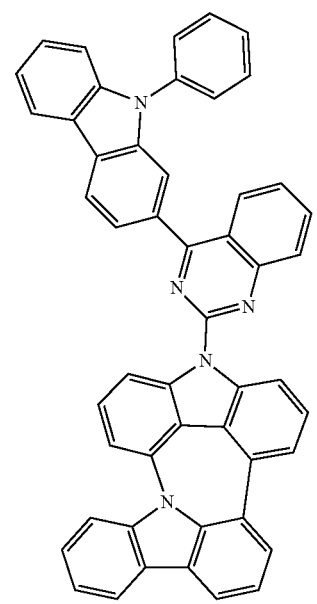
C-9
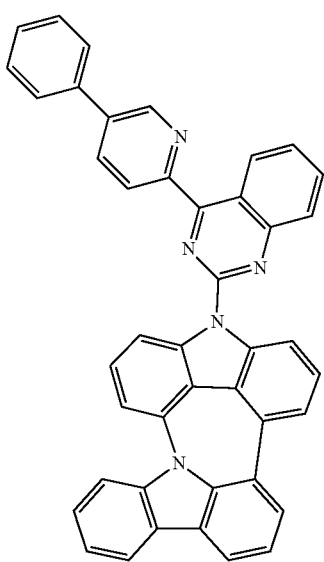
C-10
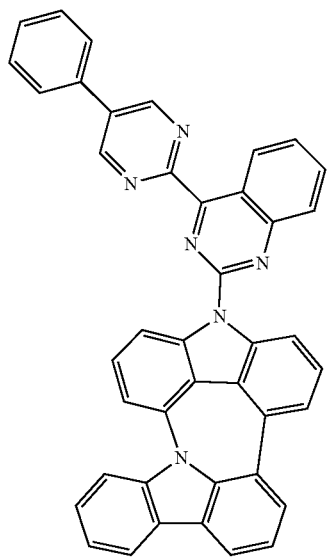
C-11
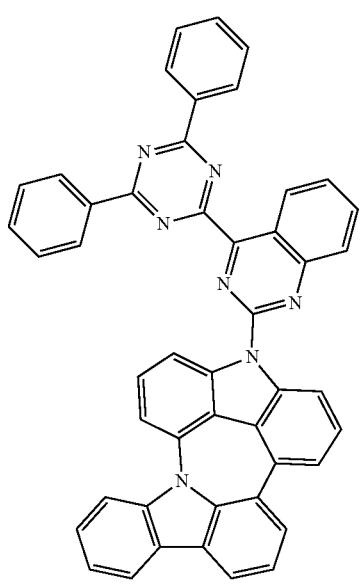
C-12
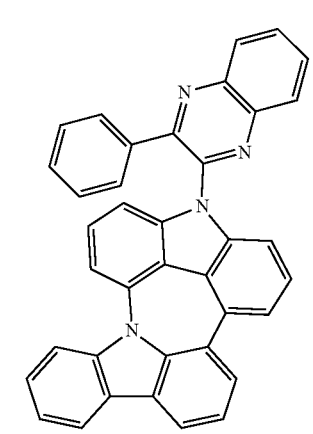
C-13

-continued
C-14
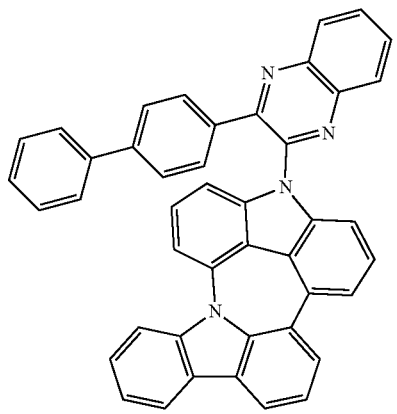
C-15
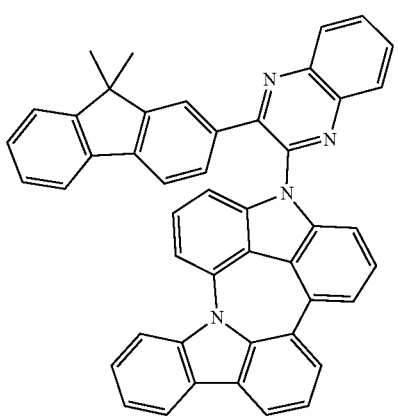
C-16
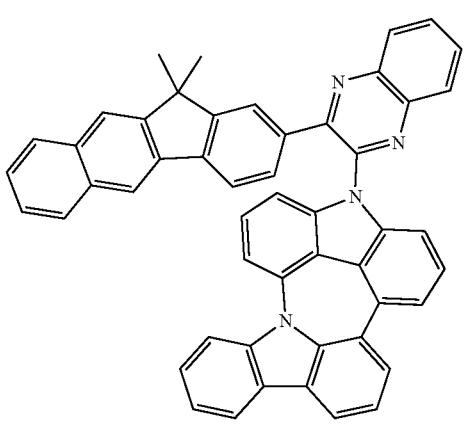
-continued
C-17
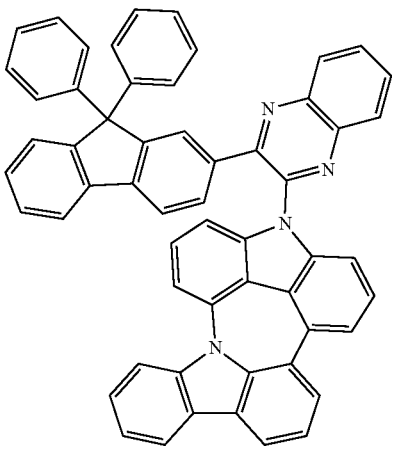
C-18
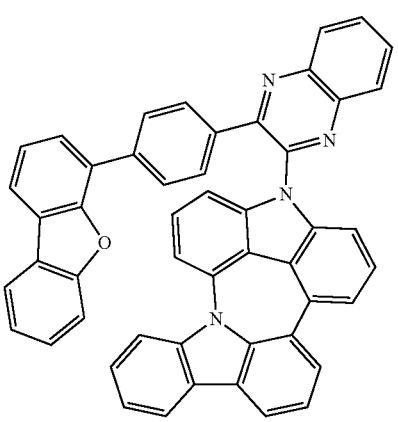
C-19
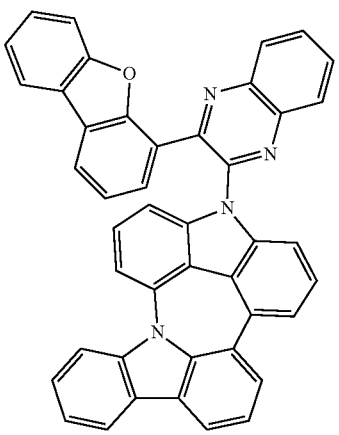

C-20
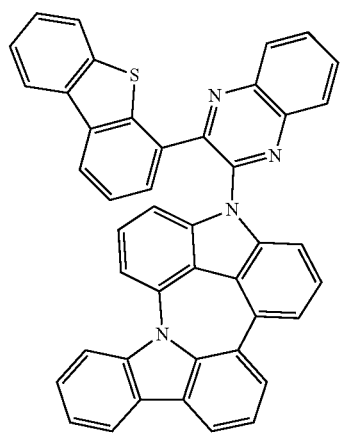
C-21
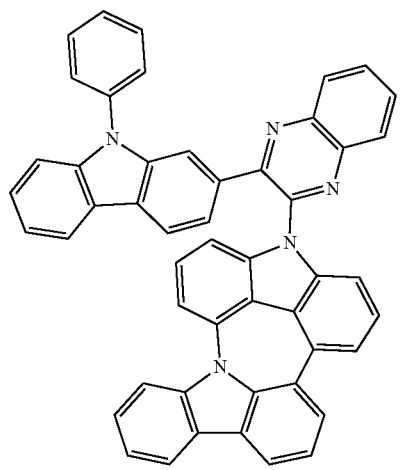
C-22
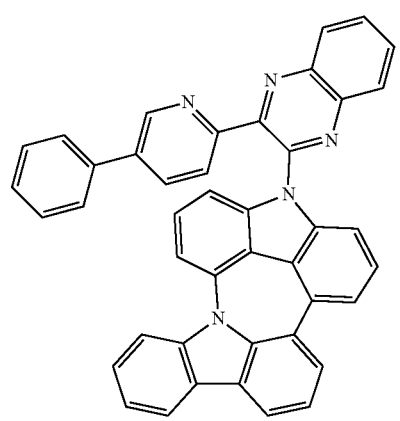
C-23
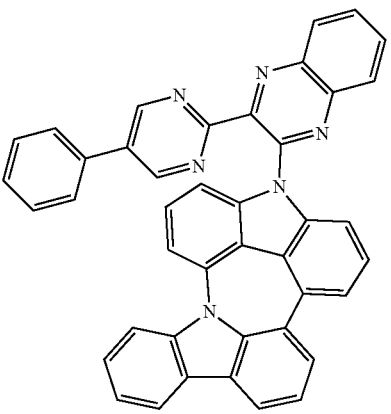
C-24
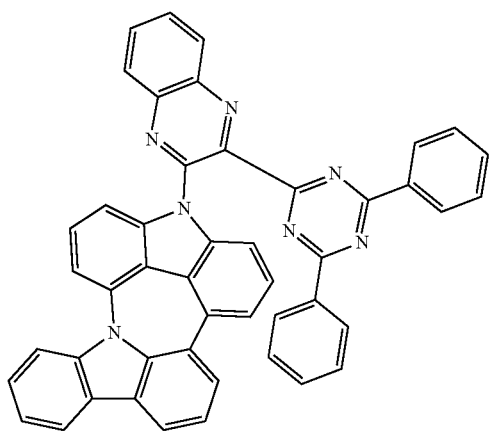
C-25
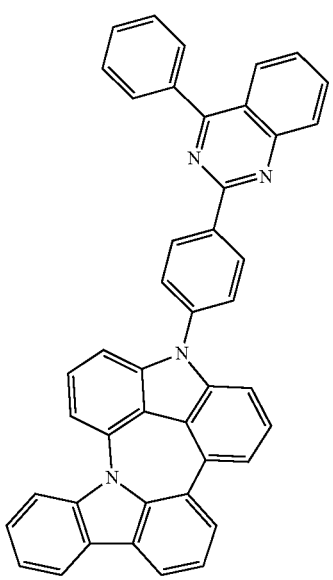

C-26
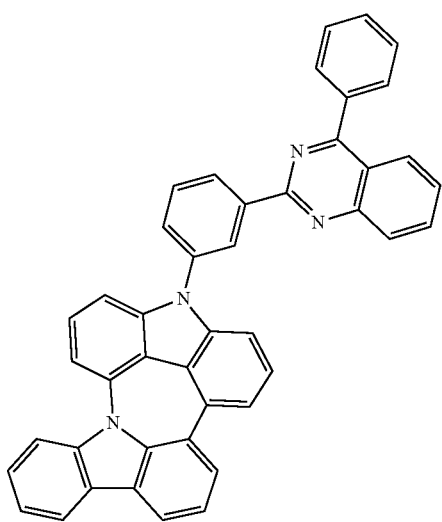
C-27
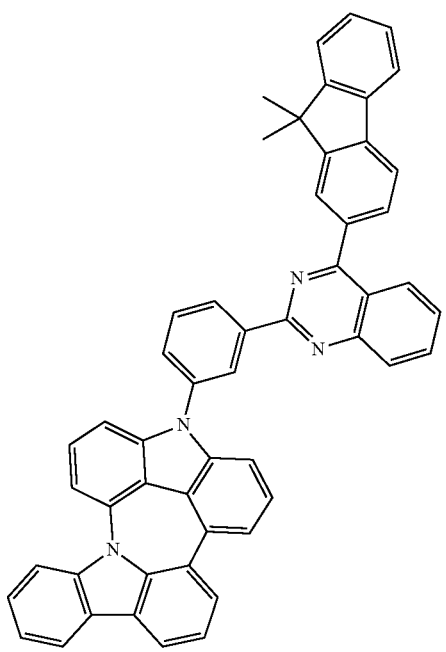
C-28
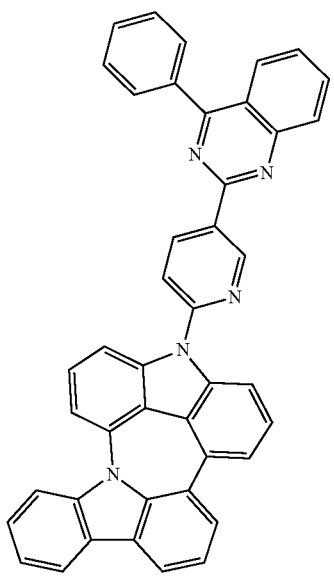
C-29
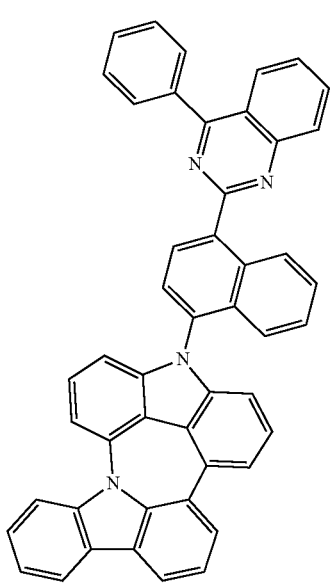

C-30
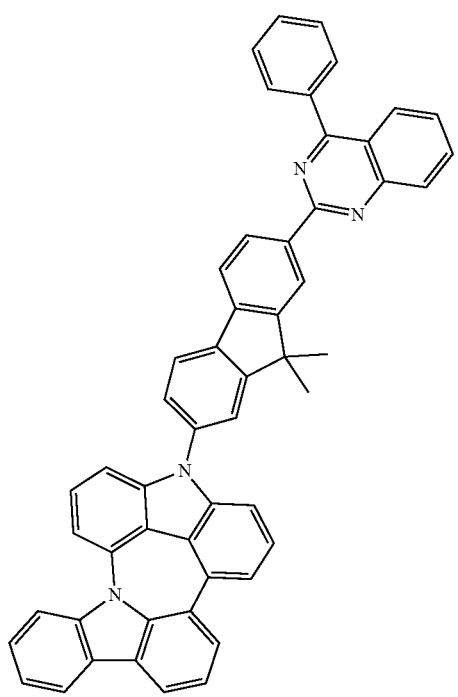
C-32
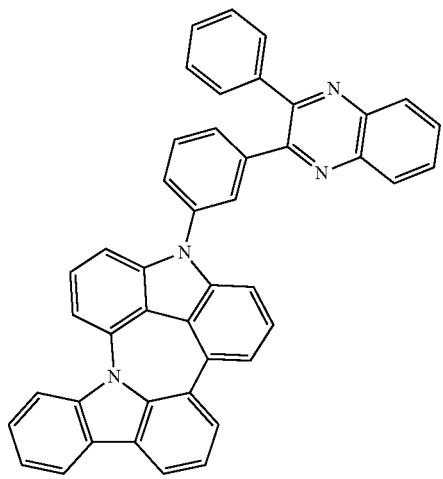
C-33
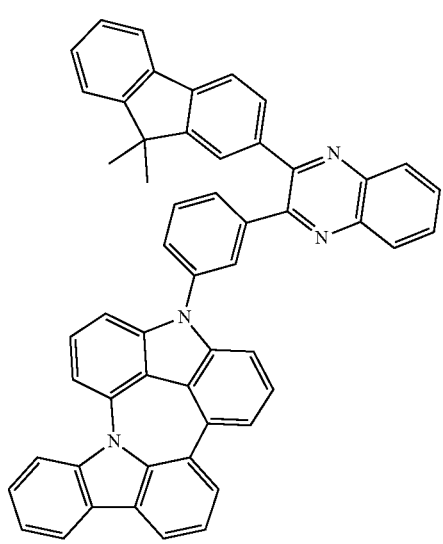
C-31
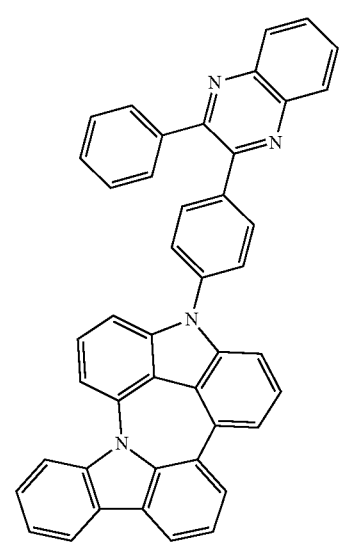
C-34
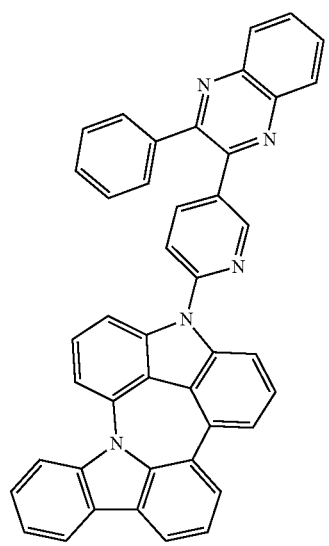

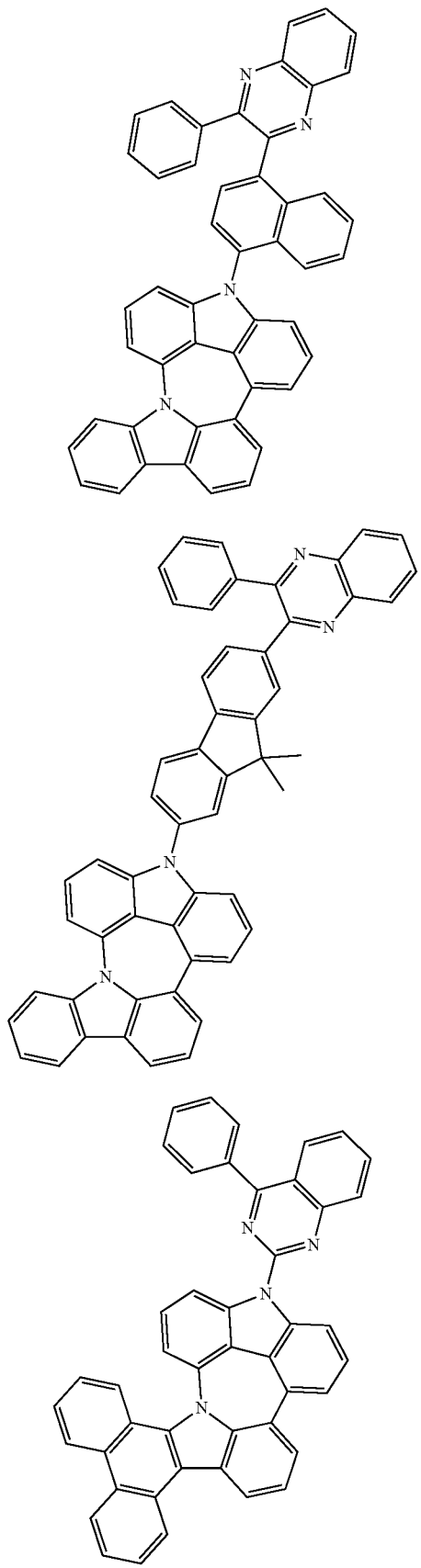
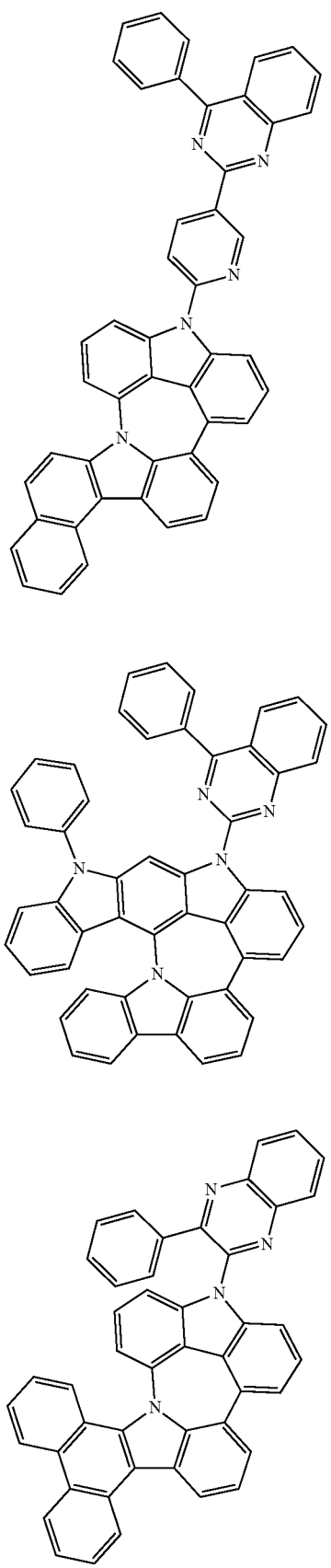

-continued
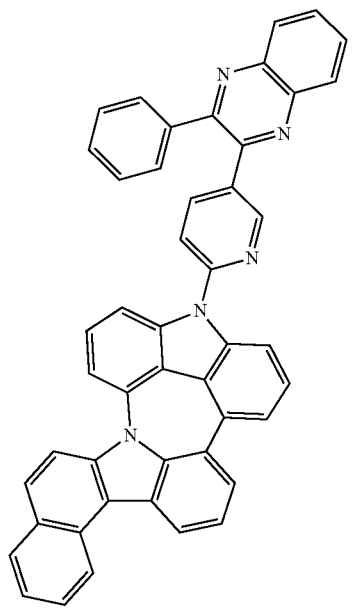
C-47
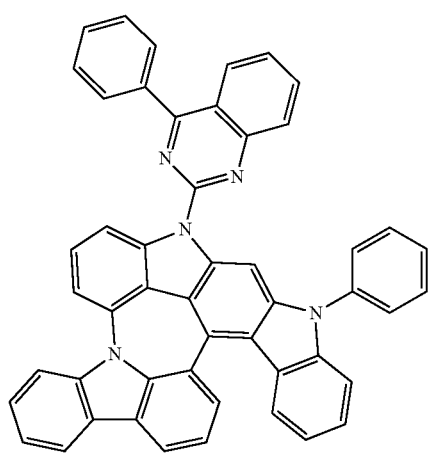
C-48
C-49
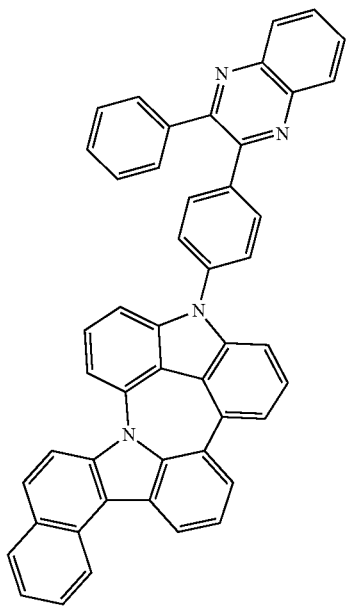
C-50
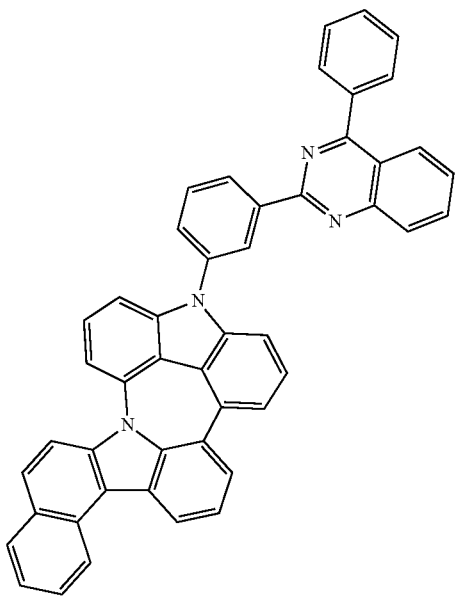
C-51

C-52
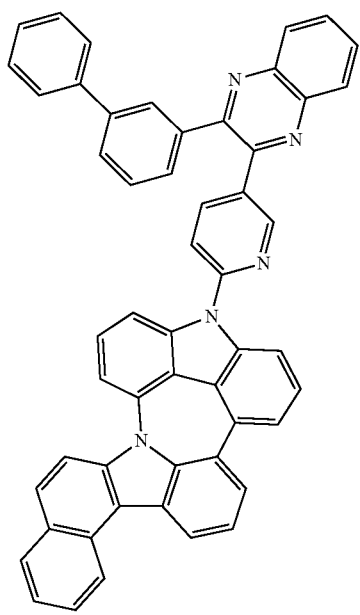
C-53
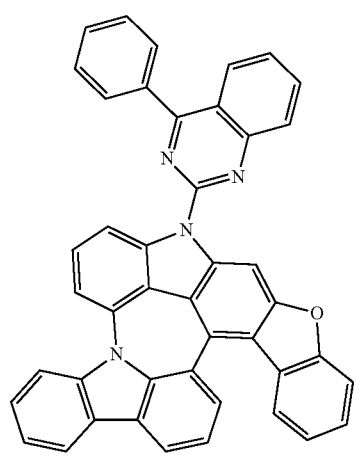
C-54
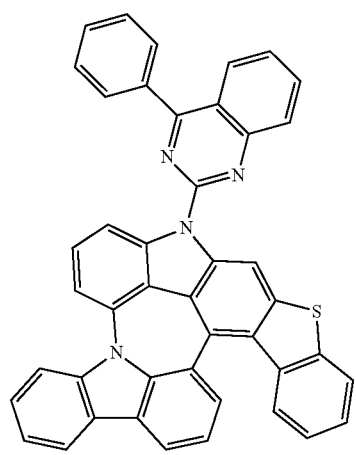
C-55
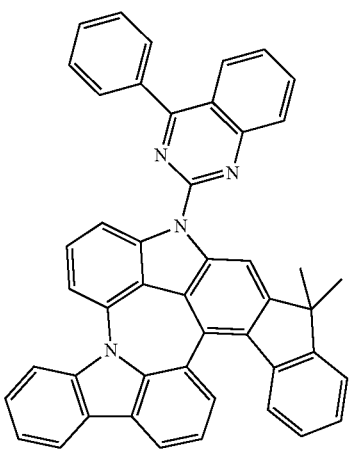
C-56
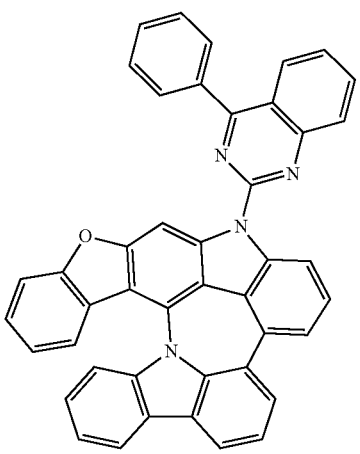
C-57
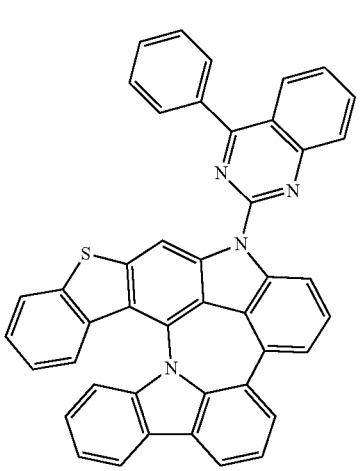

C-58
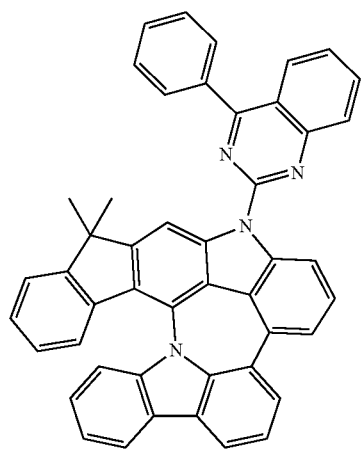
C-59
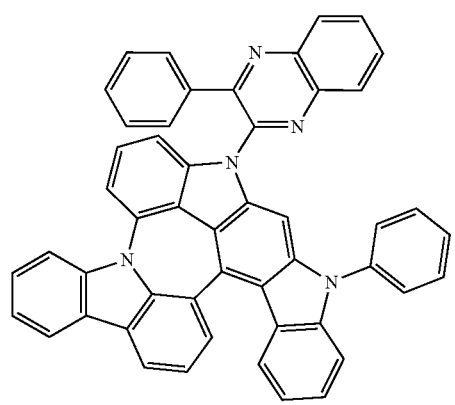
C-60
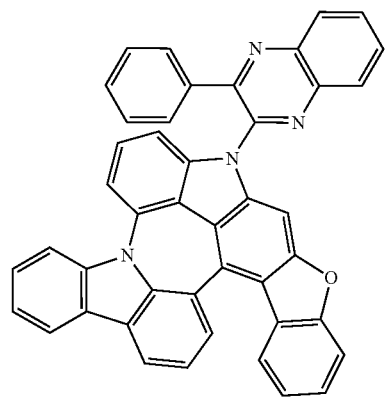
C-61
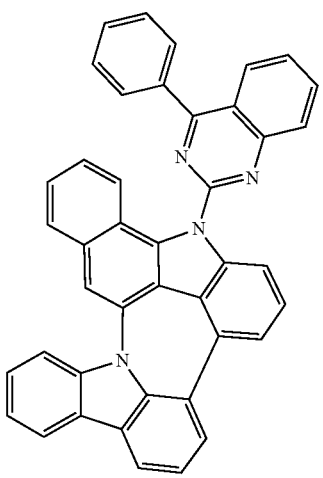
C-62
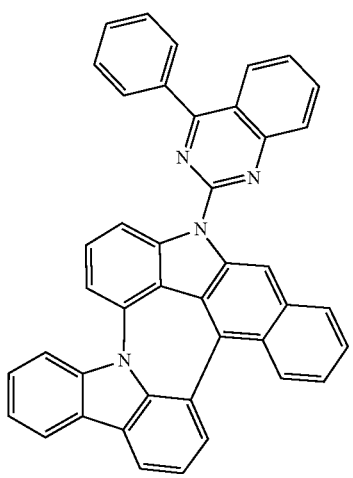
C-63
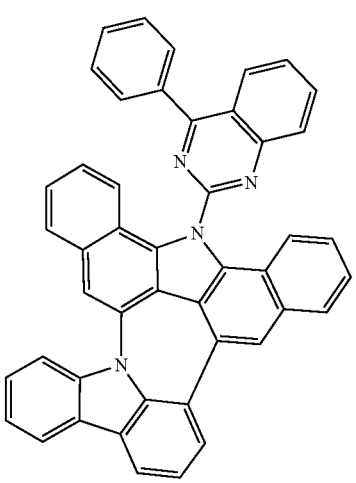

-continued

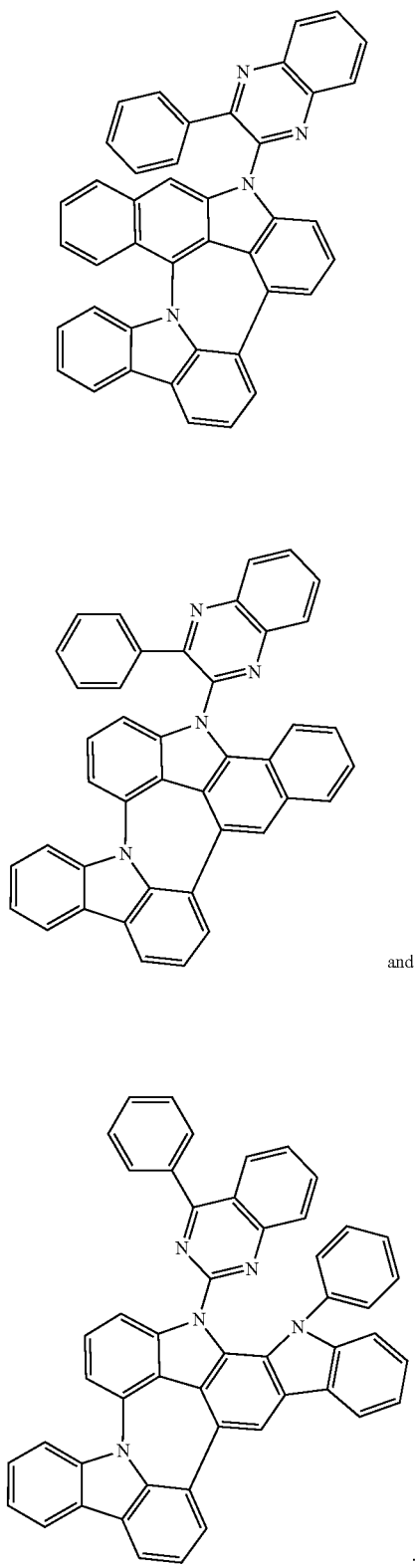

6. An organic electroluminescent device comprising the organic electroluminescent compound according to claim 1.

7. An organic electroluminescent compound, wherein the organic electroluminescent compound is represented by any of the following formulae 4 and 5:

$L_1$ represents a single bond, a substituted or unsubstituted (C6-C30)arylene, or a substituted or unsubstituted (3- to 30-membered) heteroarylene;

$R_1$, $R_2$, and $R_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or two or more $R_1$'s may be linked to an adjacent substituent(s) to form a substituted or unsubstituted (3 to 30-membered), mono- or polycyclic, alicyclic or aromatic ring, or a fused ring of the alicyclic ring and the aromatic ring, whose carbon atom(s) may be replaced with at least one heteroatom selected from the group consisting of nitrogen, oxygen, and sulfur; or two or more $R_2$'s may be linked to an adjacent substituent(s) to form a substituted or unsubstituted (3 to 30-membered), mono- or polycyclic, alicyclic or aromatic ring, or a fused ring of the alicyclic ring and the aromatic ring, whose carbon atom(s) may be replaced with at least one heteroatom selected from the group consisting of nitrogen, oxygen, and sulfur; or two or more $R_3$'s may be linked to an adjacent substituent(s) to form a substituted or unsubstituted (3 to 30-membered), mono- or polycyclic, alicyclic or aromatic ring, or a fused ring of the alicyclic ring and the aromatic ring, whose carbon atom(s) may be replaced with at least one heteroatom selected from the group consisting of nitrogen, oxygen, and sulfur;

$R_4$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

wherein the heteroaryl(ene) contains one or more heteroatoms selected from the group consisting of B, N, O, S, Si, and P;

a, b, and c, each independently, represent an integer of 1 to 3, and when a, b, or c is an integer of 2 or more, each of $R_1$, $R_2$ or $R_3$ may be the same or different.

8. The organic electroluminescent compound according to claim 7, wherein the compound represented by formula 4 or formula 5 is selected from the group consisting of:

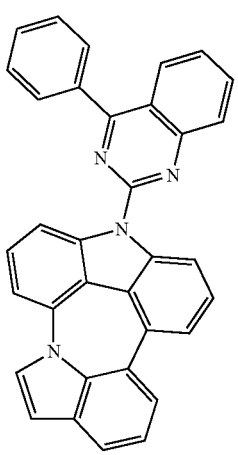

C-37

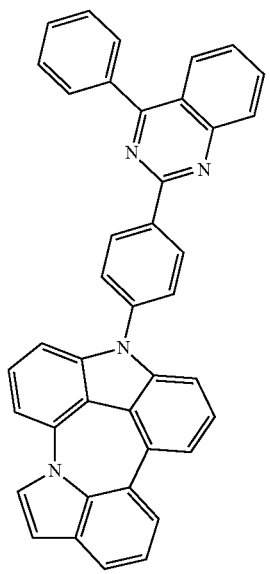

C-38

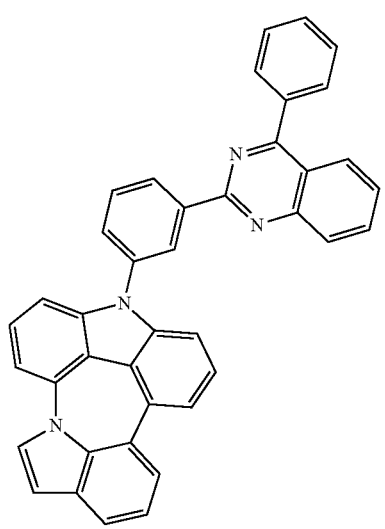

C-39

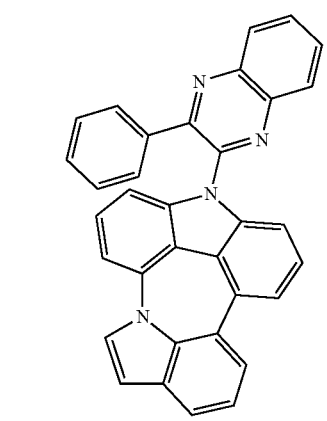

C-43

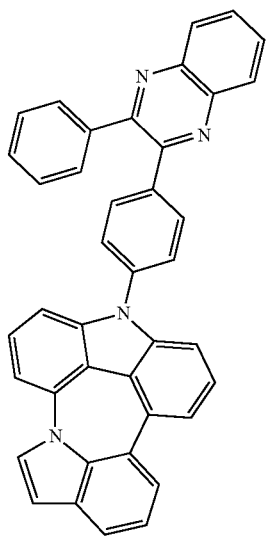
C-44
and
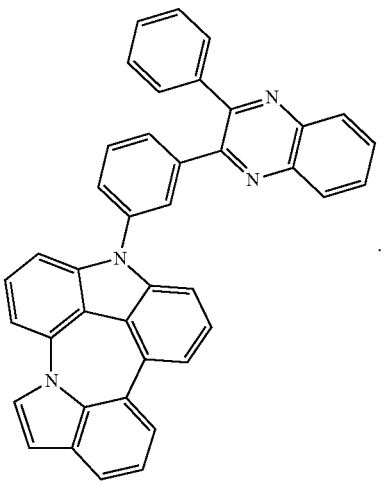
C-45
9. An organic electroluminescent device comprising the organic electroluminescent compound according to claim 7.
* * * * *